(12) United States Patent
Roninson et al.

(10) Patent No.: US 12,281,080 B2
(45) Date of Patent: *Apr. 22, 2025

(54) QUINOLINE-BASED COMPOUNDS AND METHODS OF INHIBITING CDK8/19

(71) Applicants: University of South Carolina, Columbia, SC (US); Senex Biotechnology, Inc., Columbia, SC (US)

(72) Inventors: Igor Roninson, Lexington, SC (US); Campbell McInnes, Irmo, SC (US); Mengqian Chen, Lexington, SC (US); Li Zhang, West Columbia, SC (US); Jing Li, Columbia, SC (US)

(73) Assignees: University of South Carolina, Columbia, SC (US); Senex Biotechnology, Inc., Columbia, SC (US)

( * ) Notice: Subject to any disclaimer, the term of this patent is extended or adjusted under 35 U.S.C. 154(b) by 752 days.

This patent is subject to a terminal disclaimer.

(21) Appl. No.: 17/330,279

(22) Filed: May 25, 2021

(65) Prior Publication Data
US 2021/0276956 A1    Sep. 9, 2021

Related U.S. Application Data

(63) Continuation-in-part of application No. 16/547,350, filed on Aug. 21, 2019, now Pat. No. 11,014,906.

(60) Provisional application No. 62/720,774, filed on Aug. 21, 2018.

(51) Int. Cl.
| | |
|---|---|
| C07D 215/48 | (2006.01) |
| A61P 35/00 | (2006.01) |
| A61P 35/02 | (2006.01) |
| C07D 215/18 | (2006.01) |
| C07D 215/233 | (2006.01) |
| C07D 215/42 | (2006.01) |
| C07D 215/44 | (2006.01) |

(52) U.S. Cl.
CPC ............ *C07D 215/48* (2013.01); *A61P 35/00* (2018.01); *A61P 35/02* (2018.01); *C07D 215/18* (2013.01); *C07D 215/233* (2013.01); *C07D 215/42* (2013.01); *C07D 215/44* (2013.01)

(58) Field of Classification Search
None
See application file for complete search history.

(56) References Cited

U.S. PATENT DOCUMENTS

| 6,964,956 B2 | 11/2005 | Cywin |
| 7,074,801 B1 | 7/2006 | Yoshida |
| 8,410,273 B2 | 4/2013 | Kanno |
| 8,598,344 B2 | 12/2013 | Porter |
| 9,321,737 B2 | 4/2016 | Roninson |
| 9,636,342 B2 | 5/2017 | Chen |
| 11,014,906 B2 | 5/2021 | Roninson |
| 2007/0219234 A1 | 9/2007 | Oizumi |
| 2014/0309224 A1 | 10/2014 | Porter |
| 2020/0062728 A1 | 2/2020 | Roninson |

FOREIGN PATENT DOCUMENTS

| JP | 2008260693 A | 10/2008 |
| RU | 2018107581 A | 9/2019 |
| WO | 2015164374 A1 | 10/2015 |
| WO | 2016100782 A1 | 6/2016 |
| WO | 2016114655 | 7/2016 |
| WO | 2017076968 A1 | 5/2017 |
| WO | 2019168446 A1 | 9/2019 |

OTHER PUBLICATIONS

Ferguson. Nature Reviews: Drug Discovery, 2018, 17, 353-376 (Year: 2018).*
Becherer. Journal of Medicinal Chemistry, 2015, 58, 7021-7056 (Year: 2015).*
"Hydrogen", https://periodic.lanl.gov/1.shtml, 2016, accessed Sep. 10, 2020.
"Prevention-prostate cancer foundation (PCF)" http://www.pcf.orf/site/c.leJRIROrEpH/b.5802029/k.31EA/Prevention.htm.
Chen, M.; et al. CDK8/19 Mediator kinases potentiate induction of transcription by NFkappaB. Proc Natl Acad Sci U S A 2017, 114, 10208-10213.
Hall, D. D.; et al. Ectopic expression of Cdk8 induces eccentric hypertrophy and heart failure. JCI Insight 2017, 2.
Han, X., et al. "Discovery of potent and selective CDK8 inhibitors through FBDD approach." Bioorganic & medicinal chemistry letters 27.18 (2017): 4488-4492.
Hatcher, J. M.; et al. Development of Highly Potent and Selective Steroidal Inhibitors and Degraders of CDK8. ACS Med Chem Lett 2018, 9, 540-545.
Johannessen, L.; et al. Small-molecule studies identify CDK8 as a regulator of IL-10 in myeloid cells. Nat Chem Biol 2017, 13, 1102-1108.
Nakamura, A.; et al. CDK8/19 inhibition induces premature G1/S transition and ATR-dependent cell death in prostate cancer cells. Oncotarget 2018, 9, 13474-13487.
Pawar, V. G.; et al. Synthesis and biological evaluation of 4-anilinoquinolines as potent inhibitors of epidermal growth factor receptor. J Med Chem 2010, 53, 2892-901.

(Continued)

*Primary Examiner* — Noble E Jarrell
(74) *Attorney, Agent, or Firm* — Quarles & Brady, LLP

(57) ABSTRACT

Disclosed herein are quinoline-based compounds and method for inhibiting CDK8 or CDK19 for the intervention in diseases, disorders, and conditions. The quinoline-based composition comprise substituents at quinoline ring positions 4 and 6, wherein the substituent at position 4 is selected from a substituted or unsubstituted arylalkylamine or a substituted or unsubstituted arylhetrocyclylamine. Pharmaceutical compositions comprising the substituted quinoline compositions, methods of inhibiting CDK8 or CDK19, and methods of treating CDK8/19-associated diseases, disorders, or conditions are also disclosed.

19 Claims, 18 Drawing Sheets

(56) References Cited

OTHER PUBLICATIONS

Philip, S.; et al. Cyclin-Dependent Kinase 8: A New Hope in Targeted Cancer Therapy? J Med Chem 2018, 61, 5073-5092.
Porter, D. C.; et al. Cyclin-dependent kinase 8 mediates chemotherapy-induced tumor-promoting paracrine activities. Proc Natl Acad Sci U S A 2012, 109, 13799-804.
Saito, K., et al. "Discovery and structure-activity relationship of thienopyridine derivatives as bone anabolic agents." Bioorganic & medicinal chemistry 21.7 (2013): 1628-1642.
Wagle, N, et al. "Dissecting therapeutic resistance to RAF inhibition in melanoma by tumor genomic profiling." Journal of clinical oncology 29.22 (2011): 3085.
Yang, D. et al. "Further studies on bis-charged tetraazacyclophanes as potent inhibitors of small conductance Ca2+-activated K+ channels" European Journal of Medicinal Chemistry (2013) 63:907-923.
Yap, M.C.H., et al. "4-Arylalkoxyquinazolines with Antifungal Activity" Synthesis and Chemistry of Agrochemicals V (1998) 258-272.
Office Action for U.S. Appl. No. 16/547,350 dated Jun. 23, 2020 (16 pages).
Office Action for U.S. Appl. No. 16/547,350 dated Oct. 19, 2020 (11 pages).

\* cited by examiner

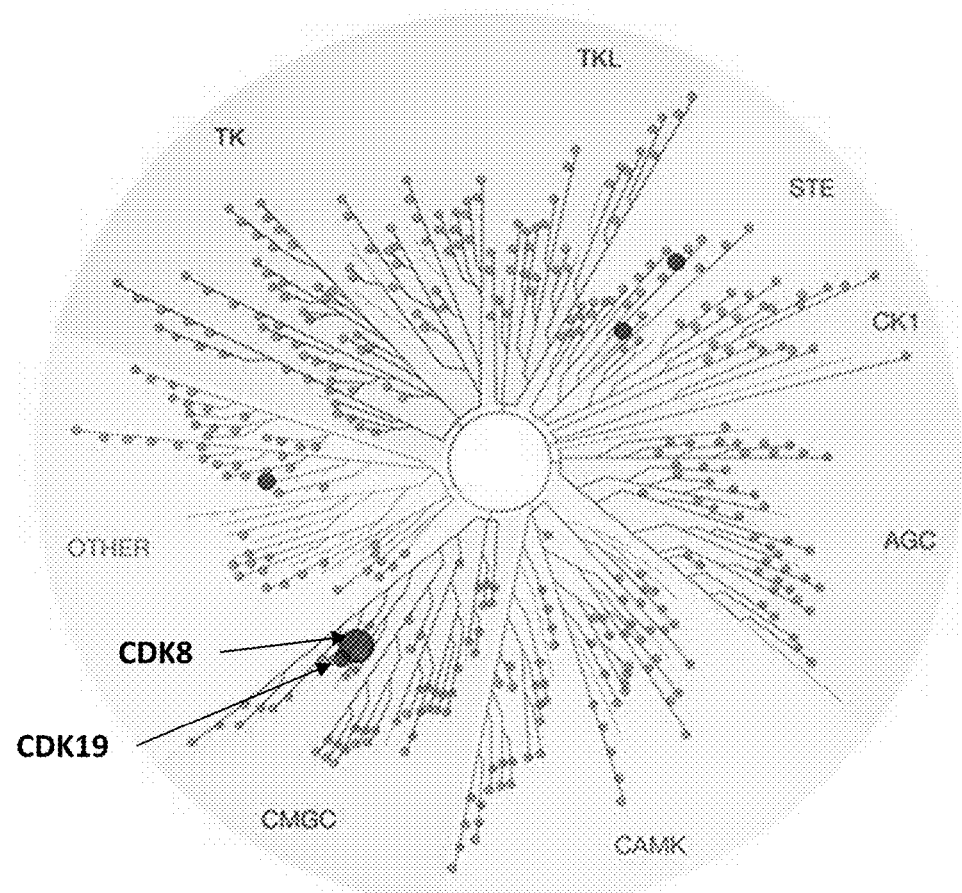
Figure 1
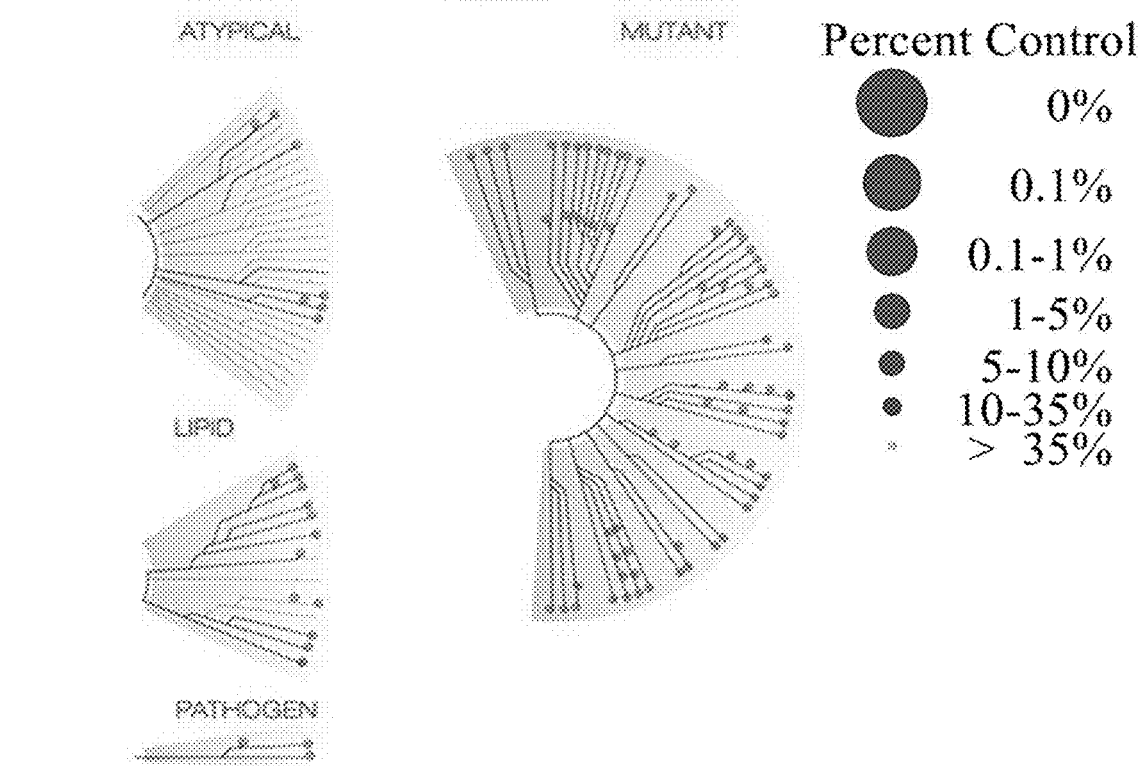

Senexin A
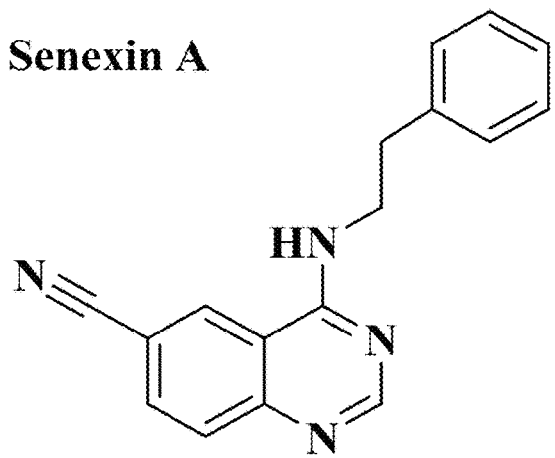
Figure 3A
6136 (GJ-2307)
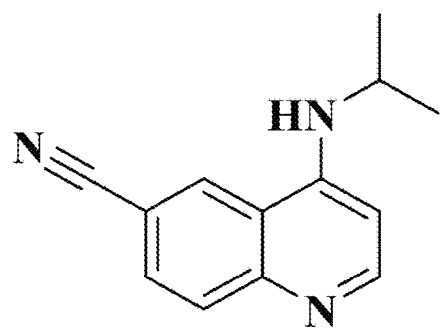
6138 (GJ-2305)
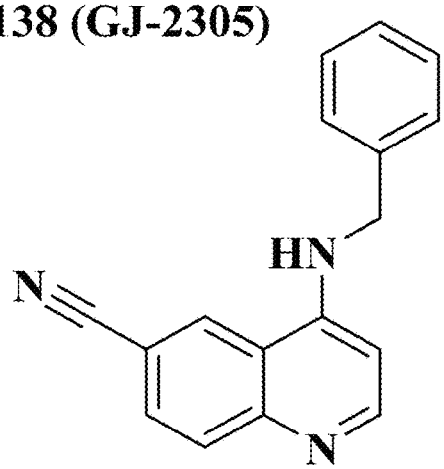
6134 (GJ-2304)
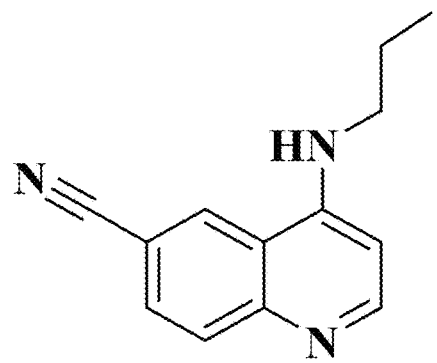
6135 (GJ-2306)
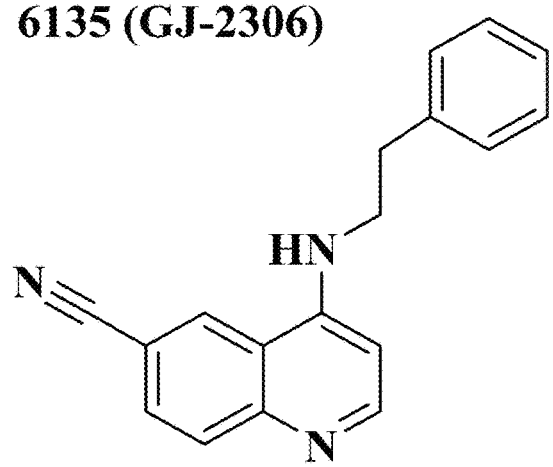

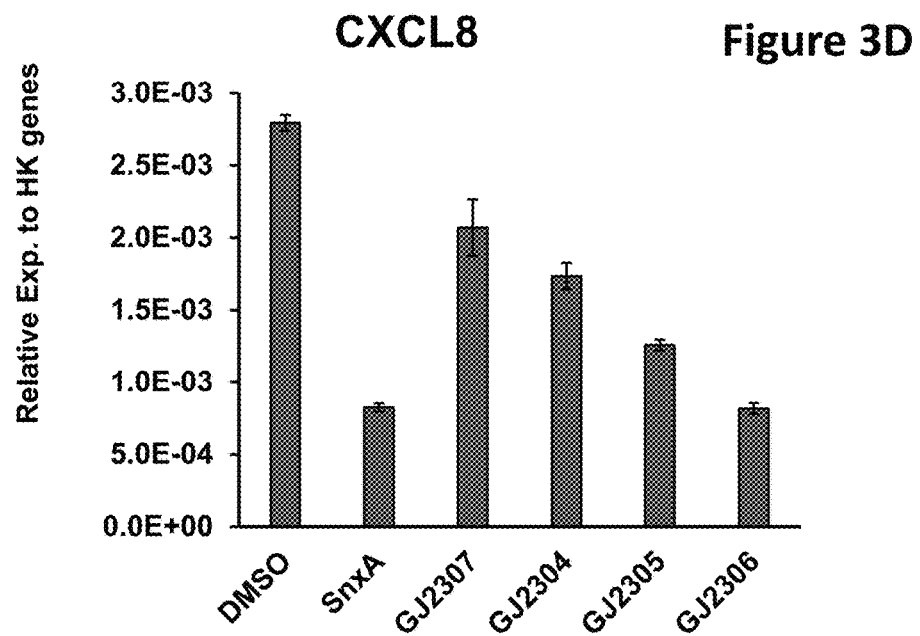
Figure 3D
Figure 4A
Senexin B
6148 (Senexin C)
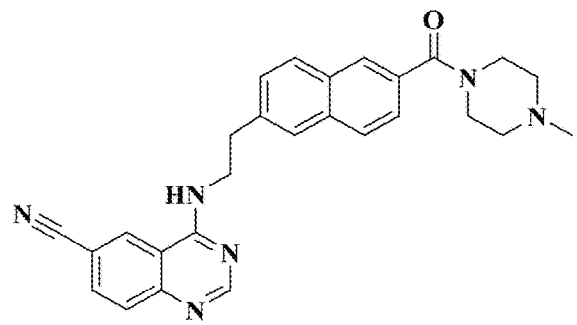
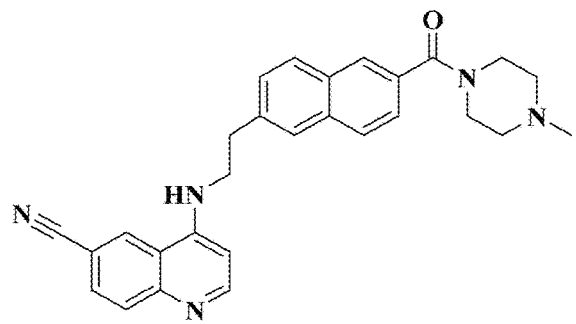

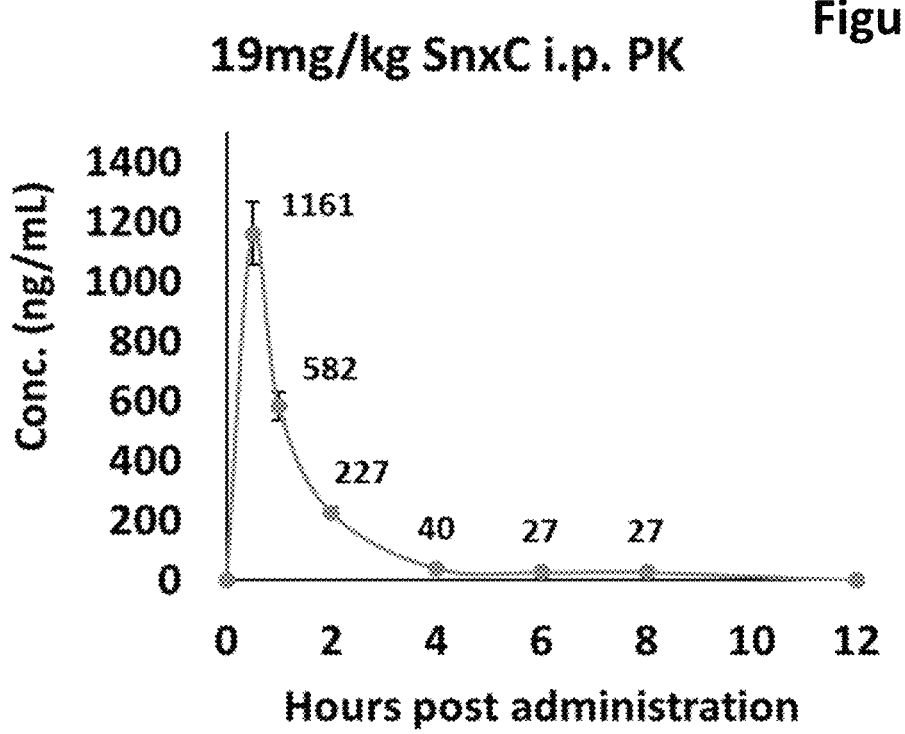
Figure 8Ai
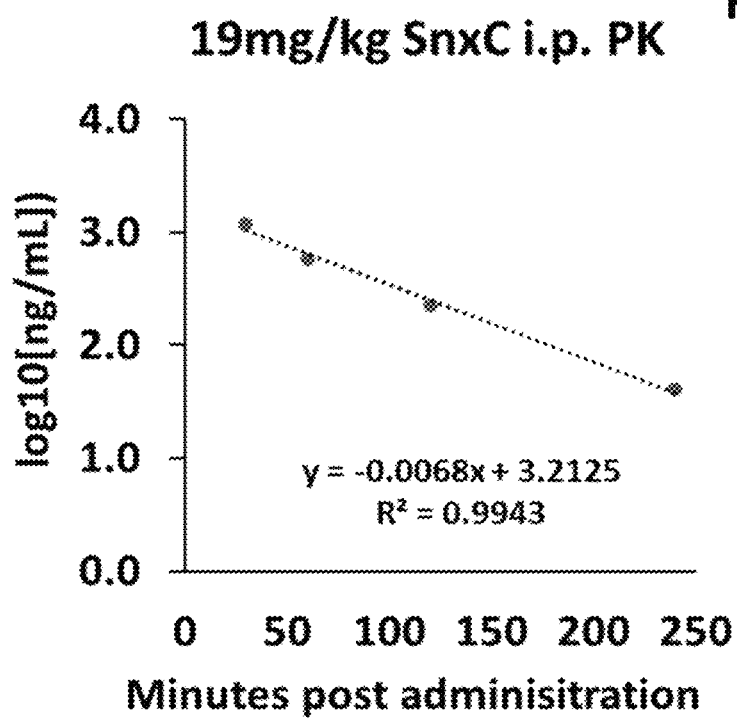
Figure 8Aii

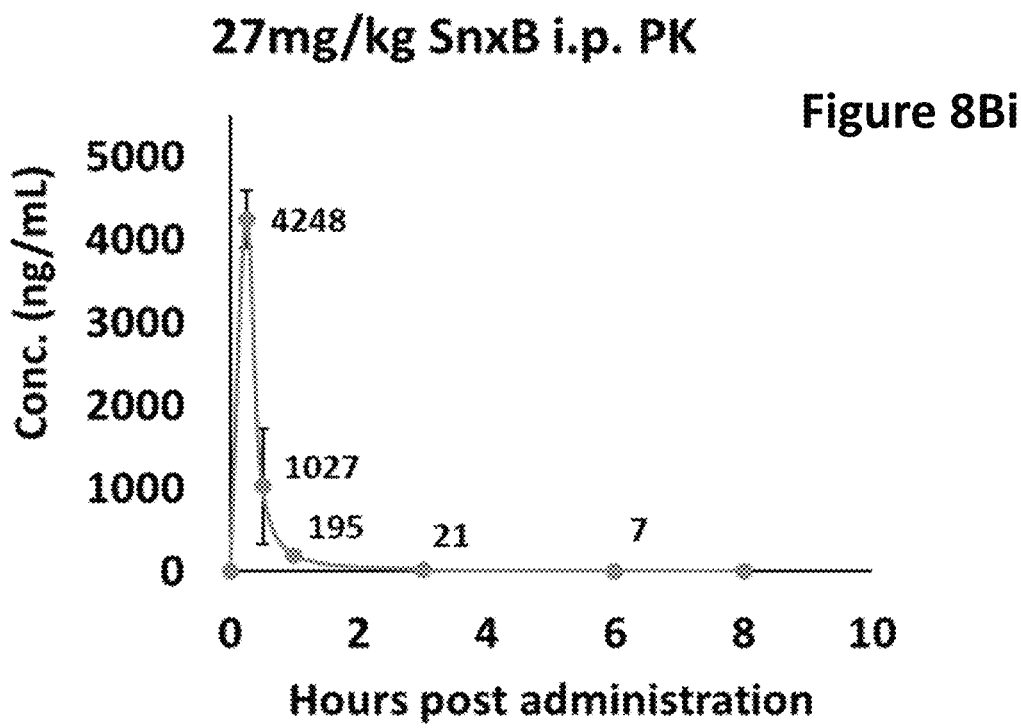
Figure 8Bi
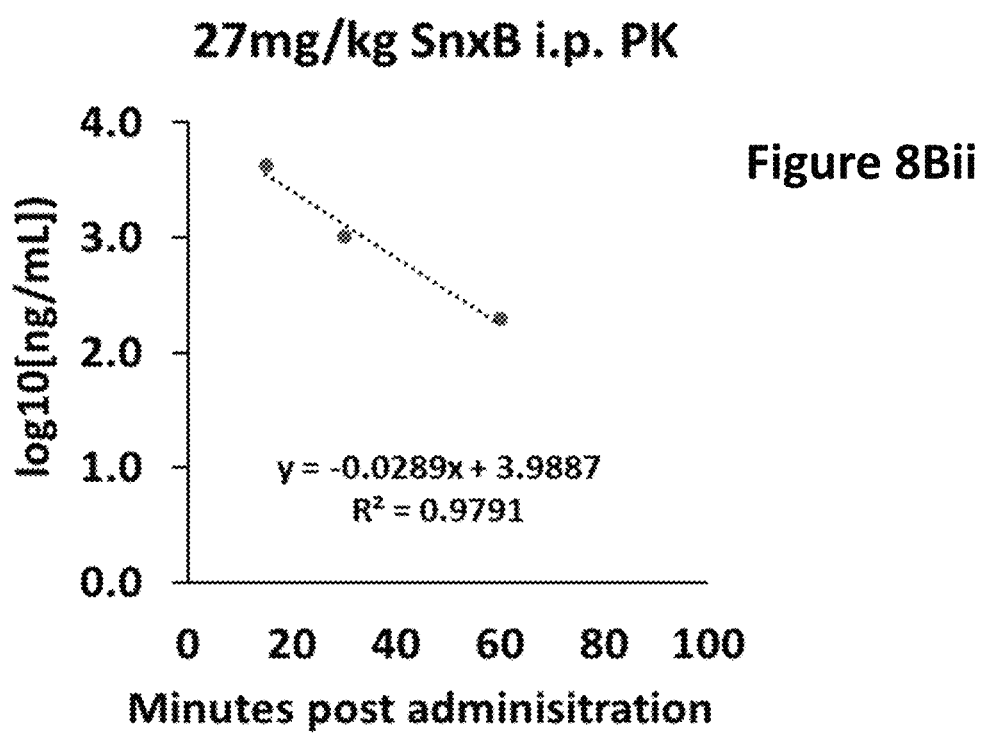
Figure 8Bii

SCCP-6216

SCCP-6283

SCCP-6219

QUINOLINE-BASED COMPOUNDS AND METHODS OF INHIBITING CDK8/19

CROSS-REFERENCE TO RELATED APPLICATIONS

This patent application is a continuation-in-part of U.S. patent application Ser. No. 16/547,350, filed Aug. 21, 2019 and issued as U.S. Pat. No. 11,014,906 on issued May 25, 2021, which claims the benefit of priority of U.S. Provisional Patent Application No. 62/720,774, filed Aug. 21, 2018, is the contents of each are incorporated herein by reference in their entirety.

FIELD OF INVENTION

The invention relates quinoline-based compounds and methods for inhibiting CDK8/19 for intervention in diseases, disorders, or conditions.

BACKGROUND

CDK8 and CDK19, two closely related transcription-regulating kinases, have become a burgeoning novel cancer drug target (Philip, S. et al., *J Med Chem* 2018, 61, 5073-5092). Aside from cancer, CDK8/19 inhibitors show promise in inflammation-associated diseases (US Patent Pub. No. 2014/0309224 to Porter, D. C.; Johnannessen, L., et al., *Nat Chem Biol* 2017, 13, 1102-1108); cardiovascular diseases (Hall, D., et al., *JCI Insight* 2017, 2; International Patent Pub. No. WO 2016/100782 to Roninson, I. B.); ribosomopathies; conditions characterized by reduced number of hematopoietic stem cells and/or progenitor cells; and bone anabolic disorders (International Patent Pub. No. WO 2017/076968 to Flygare, A.).

Compounds can be readily identified as CDK8/19 inhibitors through a variety of cell-free and cell-based assays (Philip 2018). A number of CDK8/19 inhibitors have been reported (Philip 2018). These include certain quinazoline-based compounds developed by some of the instant inventors that are highly selective for CDK8/19, such as SNX2-1-53 (a.k.a. Senexin A) (Porter, D. C., et al., *Proc Natl Acad Sci USA* 2012, 109, 13799-804; U.S. Pat. No. 8,598,344 to Porter, D. C.) and SNX2-1-165 (a.k.a. Senexin B) (U.S. Pat. No. 9,321,737 to Roninson, I. B.). Other CDK8/19 inhibitors have been reported more recently (Hatcher, J. M. et al., ACS Med Chem Lett 2018, 9, 540-545; Nakamura, A. et al., Oncotarget 2018, 9, 13474-13487; Han, X., et al., Bioorg Med Chem Lett 2017, 27, 4488-4492). Notably, at least some of a series of thienopyridine derivatives described as bone anabolic agents (Saito, K. et al., *Bioorg Med Chem* 2013, 21, 1628-42) were found to be CDK8/19 inhibitors (WO 2017/076968). None of the CDK8/19 inhibitors have yet been approved for clinical use and there is a need for novel CDK8/19 inhibitors that would be improved in regard to potency, target selectivity, and pharmacokinetic properties.

BRIEF SUMMARY OF THE INVENTION

Disclosed herein are quinoline-based compounds and methods for inhibiting CDK8/19 for the intervention in diseases, disorders, and conditions. The quinoline-based compositions comprise substituents at quinoline ring positions 4 and 6, wherein the substituent at position 4 is selected from a substituted or unsubstituted arylalkylamine or a substituted or unsubstituted arylhetrocyclylamine. Pharmaceutical compositions comprising the substituted quinoline compositions, methods of inhibiting CDK8 or CDK19, and methods of treating CDK8/19-associated diseases, disorders, or conditions are provided herein.

The present disclosure provides for compositions comprising a compound of Formula I

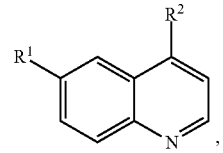

(Formula I)

wherein $R^1$ is selected from a halogen; —CN, —NO$_2$, —R, —OR, —SR, —NRR', —S(O)$_2$R, —S(O)$_2$NRR', —S(O)R, —C(O)R, —C(O)OR, —C(O)NRR', —C(O)N(R)OR', —N(R)C(O)OR', —N(R)C(O)NR'R", or —N(R)S(O)$_2$R', where each R, R', and R" may be independently selected from hydrogen, a substituted or unsubstituted alkyl, a substituted or unsubstituted cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur, or two R, R', or R" groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur; and wherein $R^2$ is selected from a substituted or unsubstituted arylalkylamine or a substituted or unsubstituted arylhetrocyclylamine.

In some embodiments, of the invention $R^2$ is selected from a substituted or unsubstituted arylalkylamine. The substituted or unsubstituted arylalkylamine may comprise a phenyl moiety or a naphthyl moiety.

In some embodiments, the compound is represented by Formula IA

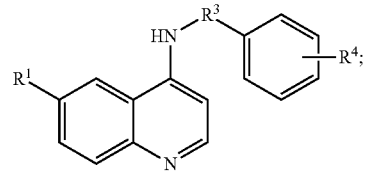

(Formula IA)

wherein $R^3$ comprises a substituted or unsubstituted, branched or unbranched C1-C6 alkylene; and wherein $R^4$ is selected from selected from a halogen; —CN, —NO$_2$, —R, —OR, —SR, —RNR'R", —S(O)$_2$R, —S(O)$_2$NRR', —S(O)R, —C(O)R, —RC(O)R', —C(O)OR, —C(O)NRR', —C(O)N(R)OR', —N(R)C(O)OR', —N(R)C(O)NR'R", or —N(R)S(O)$_2$R', where each R, R', and R" may be independently selected from hydrogen, a substituted or unsubstituted alkyl, a substituted or unsubstituted cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur, or two R, R', or R" groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur. In certain embodiments, the compound is represented by Formula IAi

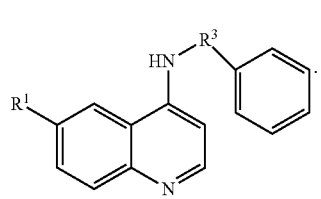

(Formula IAi)

For either of the compounds represented by Formula IA or IAi, $R^3$ may be selected from —$CH_2$—, —$CH_2CH_2$—, or —$CH_2CH_2CH_2$— and/or $R^1$ may be selected from hydrogen, cyano, chloro, bromo, iodo, nitro, amino, or trifluoromethyl.

In some embodiments, the compound is represented by Formula IB

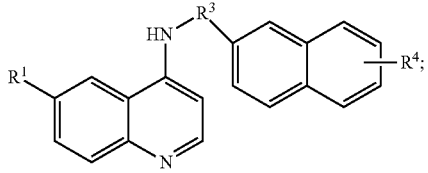

(Formula IB)

wherein $R^3$ comprises a substituted or unsubstituted, branched or unbranched C1-C6 alkylene; and wherein $R^4$ is selected from a halogen; —CN, —$NO_2$, —R, —OR, —SR, —RNR'R", —$S(O)_2R$, —$S(O)_2NRR'$, —S(O)R, —C(O)R, —RC(O)R', —C(O)OR, —C(O)NRR', —C(O)N(R)OR', —N(R)C(O)OR', —N(R)C(O)NR'R", or —N(R)S(O)$_2$R' where each R, R', and R" may be independently selected from hydrogen, a substituted or unsubstituted alkyl, a substituted or unsubstituted cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur, or two R, R', or R" groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur.

In some embodiments, wherein $R^4$ comprises —C(O)NRR'. In particular embodiments, the R and R' groups on the same nitrogen are taken together with their intervening atoms to form a substituted or unsubstituted 4-7 membered saturated, partially unsaturated, or heteroaryl ring having 0-3 heteroatoms, in addition to the nitrogen, independently selected from nitrogen, oxygen, or sulfur. In other embodiments, R and R are independently selected from hydrogen, a substituted or unsubstituted alkyl, a substituted or unsubstituted cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur. In some embodiments, when $R^4$ comprises —C(O)NRR', $R^1$ is —CN, $NO_2$, a halogen, an amino, or a halo-substituted alkyl.

In some embodiments, $R^4$ comprises

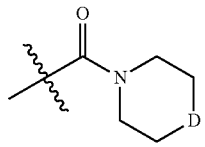

and D is —$N(R^C)$— and $R^C$ is a substituted, branched or unbranched C1-C6 alkyl or D is —S(=O)(=$NR^D$)— and $R^D$ is hydrogen or a substituted or unsubstituted, branched or unbranched C1-C6 alkyl, —S—, or —S(O)—.

In certain embodiments, D is —$N(R^C)$— and $R^C$ is an oxo substituted C1-C6 alkyl. Suitably, $R^C$ may be —$C(O)CH_3$ or —$C(O)OC(CH_3)_3$.

In certain embodiments, D is —$N(R^C)$— and $R^C$ is a hydroxyl substituted C1-C6 alkyl.

Suitably, $R^C$ may be —$(CH_2)_3OH$.

In certain embodiments, D is —$N(R^C)$— and $R^C$ is an amino substituted C1-C6 alkyl. Suitably, $R^C$ may be —$(CH_2)_3NH_2$.

In certain embodiments, D is —S(=O)(=$NR^D$)— and $R^D$ is hydrogen or the substituted or unsubstituted, branched or unbranched C1-C6 alkyl, —S—, or —S(O)—. Suitably, D may be —S(=O)(=$NR^D$)— and $R^D$ is hydrogen.

In certain embodiments, the compound is represented by Formula IBi

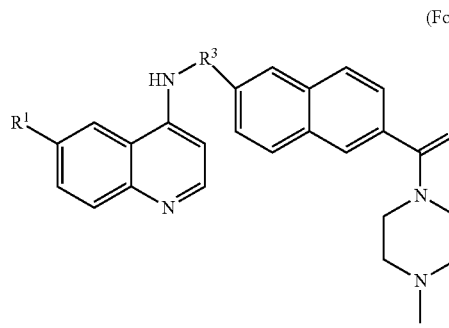

(Formula IBi)

For either of the compounds represented by Formula IB or IBi, $R^3$ may be selected from —$CH_2$—, —$CH_2CH_2$—, or —$CH_2CH_2CH_2$— and/or $R^1$ may be selected from hydrogen, cyano, chloro, bromo, iodo, nitro, amino, or trifluoromethyl.

In certain embodiments when $R^4$ comprises —C(O)NRR', at least one of R and R' is the substituted or unsubstituted alkyl. Suitably, at least one of R and R' is —$CH_3$, an amino substituted C1-C6 alkyl, of a —$NHC(O)OC(CH_3)_3$ substituted alkyl. In particular embodiments, at least one of R and R' is —$CH_3$, an amino substituted C1-C6 alkyl, or a —NHC(O)OC(CH$_3$)$_3$ substituted alkyl. In particular embodiments, each of R and R' is the substituted or unsubstituted alkyl.

In some embodiments, $R^2$ may be selected from a substituted or unsubstituted arylhetrocyclylamine. In some embodiments, the compound is represented by Formula IC

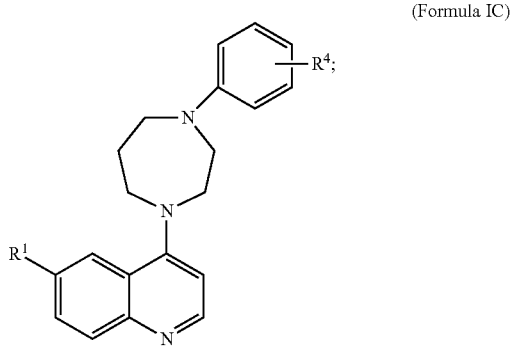

(Formula IC)

wherein R⁴ is selected from a halogen; —CN, —NO₂, —R, —OR, —SR, —RNR'R'', —S(O)₂R, —S(O)₂NRR', —S(O)R, —C(O)R, —R$^C$(O)R', —C(O)OR, —C(O)NRR', —C(O)N(R)OR', —N(R)C(O)OR', —N(R)C(O)NR'R'', or —N(R)S(O)₂R' where each R, R', and R'' may be independently selected from hydrogen, a substituted or unsubstituted alkyl, a substituted or unsubstituted cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur, or two R, R', or R'' groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur. In certain embodiments, the compound is represented by Formula ICi

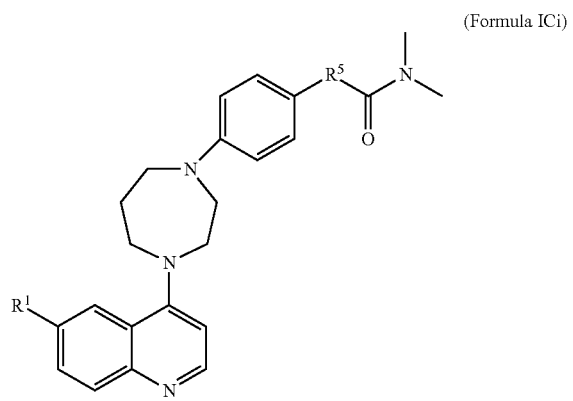

(Formula ICi)

wherein R⁵ comprises a substituted or unsubstituted, branched or unbranched C1-C6 alkylene. For either of the compounds represented by Formula IC or ICi, R⁵ may be selected from —CH₂—, —CH₂CH₂—, or —CH₂CH₂CH₂— and/or R¹ may be selected from hydrogen, cyano, chloro, bromo, iodo, nitro, amino, or trifluoromethyl.

In another aspect of the invention, the present disclosure provides for pharmaceutical compositions comprising a therapeutically effective amount of any of the compounds or compositions disclosed herein. The pharmaceutical composition may further comprise a pharmaceutically acceptable carrier, excipient, or diluent.

In another aspect of the invention, the present disclosure provides for methods of treating a subject having a CDK8-associated disease, disorder, or condition or a CDK19-associated disease, disorder, or condition. The method may comprise administering a therapeutically effective amount of any of the compounds or compositions disclosed herein. In some embodiments, the CDK8-associated disease, disorder, or condition or CDK19-associated disease, disorder, or condition is a cancer, an inflammation-associated disease, a cardiovascular disease, a ribosomopathy, a conditions characterized by reduced number of hematopoietic stem cells and/or progenitor cells, or a bone anabolic disorder.

In another aspect of the invention, the present disclosure provides for methods of inhibiting CDK8 or CDK19. The methods may comprise contacting CDK8 or CDK19 with an effective amount of any of the compounds or compositions disclosed herein. In some embodiments, the extent of inhibition of CDK8 is at least 2-fold more than the extent of inhibition of CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5 contacted with the effective amount of the compound. In particular embodiments the extent of inhibition of CDK8 is at least 2-fold more than the extent of inhibition of at least two, three, or more of CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5 contacted with the effective amount of the compound. In some embodiments, the extent of inhibition of CDK19 is at least 2-fold more than the extent of inhibition of CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5 contacted with the effective amount of the compound. In particular embodiments the extent of inhibition of CDK19 is at least 2-fold more than the extent of inhibition of at least two, three, or more of CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5 contacted with the effective amount of the compound.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 1 shows the results of kinome profiling of Senexin C, carried out by DiscoverX (now Eurofins) using the KINOMEscan™.

FIG. 3A shows several exemplary compounds of the invention.

FIGS. 3B-3D show the effects of different compounds on MYC (FIG. 3B), CXCL1 (FIG. 3C), and CXCL8 (IL8) (FIG. 3D) gene expression in TNFα-treated 293 cells (QPCR analysis).

FIG. 4A illustrates Senexin B and Senexin C.

FIGS. 8Ai-8Aii and 8Bi-8Bii show pharmacokinetics of Senexin C (FIG. 8Ai-8Aii) and Senexin B (FIG. 8Bi-8Bii) in mice following intraperitoneal injection.

(FIG. 10B) administration.

FIG. 12A shows the tumor size before removal. FIG. 12B shows the increased mouse survival following administration of Senexin C.

DETAILED DESCRIPTION OF THE INVENTION

Figure 2A:
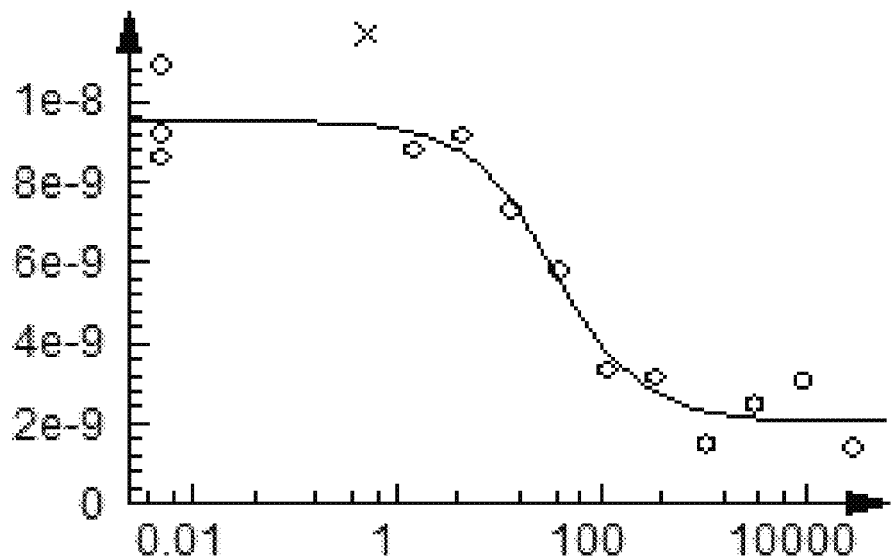
FIGS. 2A-2D show the results of Kd assays for CDK8 (FIGS. 2A and 2B) and CDK19 (FIGS. 2C and 2D) carried out in duplicate in the DiscoverX assay.
Figure 2B:
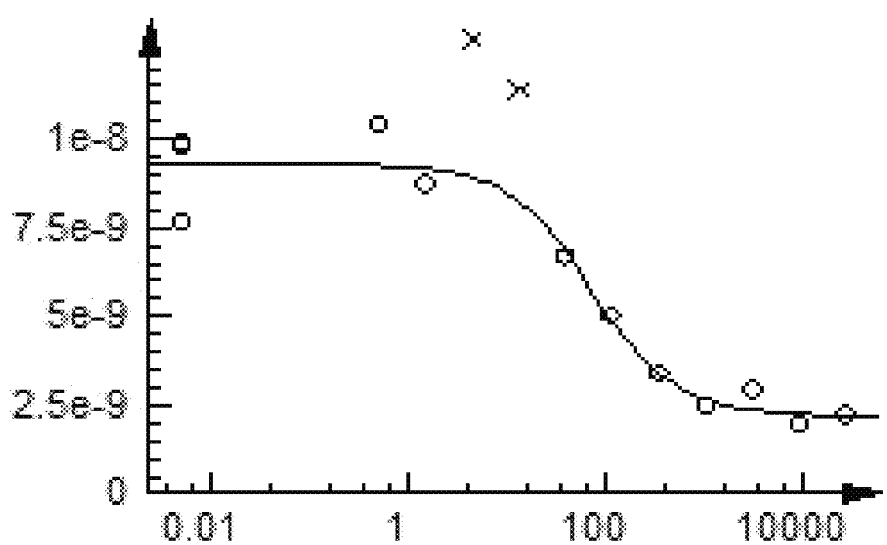
Figure 2C:
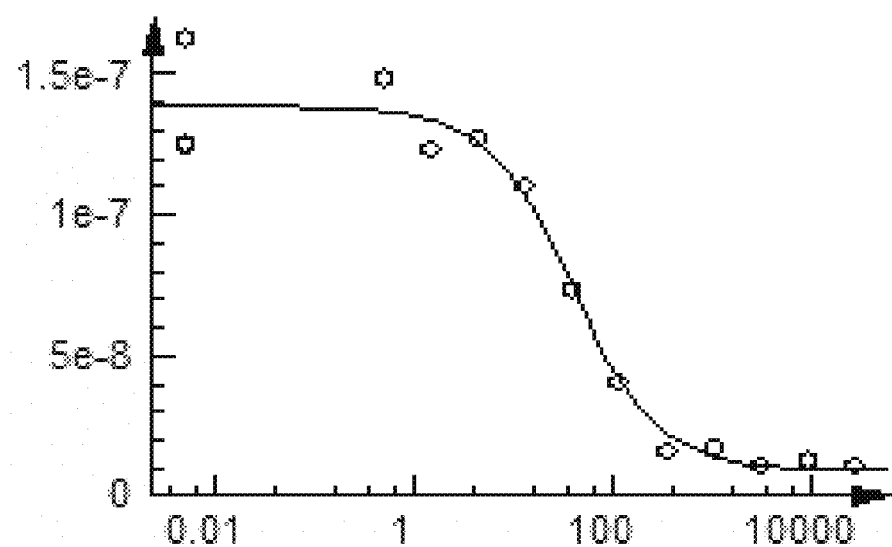
Figure 2D:
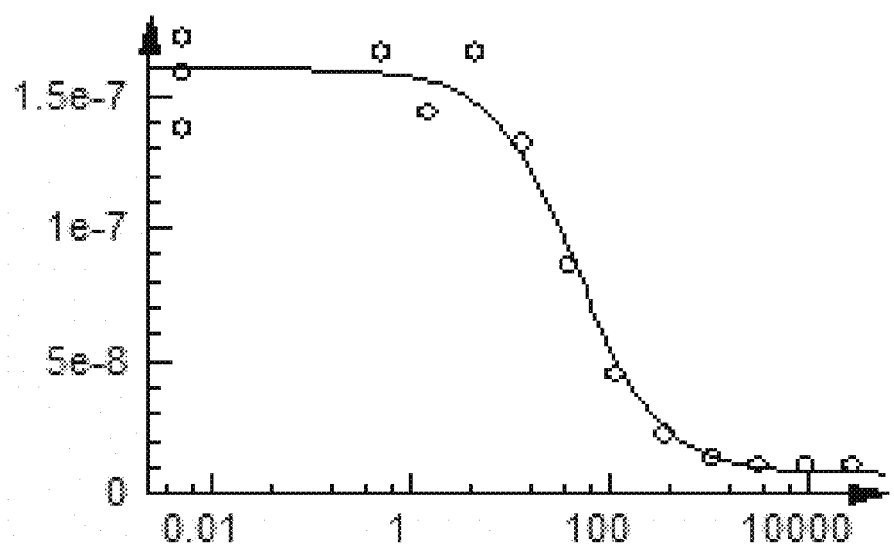

The invention provides compounds, pharmaceutical formulations and methods for inhibiting CDK8 or CDK19 and for treating diseases associated with CDK8 or CDK19 activity, such as cancer, inflammation-associated diseases, cardiovascular diseases, ribosomopathies, conditions characterized by reduced number of hematopoietic stem cells and/or progenitor cells, and bone anabolic disorders. The present invention describes a series of novel quinoline-based compounds that act as CDK8/19 inhibitors. The examples herein demonstrate that quinoline-based CDK8/19 inhibitors retain the target selectivity and potency of previously described analogous quinazoline-based SNX2-class compounds (U.S. Pat. Nos. 8,598,344 and 9,321,737) and show improved potency in cell-based assays, longer duration of target inhibition, increased metabolic stability, and improved pharmacokinetic properties relative to their quinazoline analogs.

Compositions that Inhibit CDK8/19

In a first aspect of the invention, the invention provides for compounds that inhibit CDK8/19. In some embodiments, the compounds are represented by Formula I

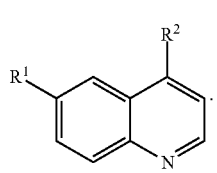

(Formula I)

The radical $R^1$ may be selected from a halogen; —CN, —NO$_2$, —R, —OR, —SR, —NRR', —S(O)$_2$R, —S(O)$_2$NRR', —S(O)R, —C(O)R, —C(O)OR, —C(O)NRR', —C(O)N(R)OR', —N(R)C(O)OR', —N(R)C(O)NR'R", or —N(R)S(O)$_2$R', where each R, R', and R" may be independently selected from hydrogen, a substituted or unsubstituted alkyl, a substituted or unsubstituted alkyl cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur, or two R, R', or R" groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur. In particular embodiments of the invention, $R^1$ may be selected from hydrogen, cyano, chloro, bromo, iodo, nitro, amino, or trifluoromethyl.

The radical $R^2$ is a substituted or unsubstituted arylalkylamine or a substituted or unsubstituted arylhetrocyclylamine. The aryl moiety of the arylalkylamine or the arylhetrocycylamine comprises a phenyl or naphthyl aromatic system. The aryl moiety may be optionally substituted at one or more ring positions. In certain embodiments, the aryl moiety is substituted at the C-4 phenyl position or the C-6 naphthyl position. The alkylene moiety of the arylalkylamine may comprise a substituted or unsubstituted, branched or unbranched C1-C6 alkylene. In certain embodiments, one or two carbons of the alkylene are optionally replaced with a heteroatom (e.g., an O, N, or S atom). In particular embodiments of the invention, the alkylene moiety is a —CH$_2$—, —CH$_2$CH$_2$—, or —CH$_2$CH$_2$CH$_2$—. The heterocyclyl moiety of the arylhetrocyclylamine may comprise a substituted or unsubstituted saturated, partially unsaturated, or aromatic 3- to 10-membered ring structures including nitrogen and, optionally, including zero to three additional heteroatoms, such as nitrogen, oxygen, and sulfur. In particular embodiments, the heterocyclyl moiety is a 6-membered or 7-membered ring comprising 2 nitrogen atoms.

In some embodiments, the aryl moiety is substituted. Aryl substituents may be selected from a halogen; —CN, —NO$_2$, —R, —OR, —SR, —RNR'R", —S(O)$_2$R, —S(O)$_2$NRR', —S(O)R, —C(O)R, —R$^C$(O)R', —C(O)OR, —C(O)NRR', —C(O)N(R)OR', —N(R)C(O)OR', —N(R)C(O)NR'R", or —N(R)S(O)$_2$R' where each R, R', and R" may be independently selected from hydrogen, a substituted or unsubstituted alkyl, a substituted or unsubstituted cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur, or two R, R', or R" groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, or sulfur.

In some embodiments of the invention, $R^4$ comprises

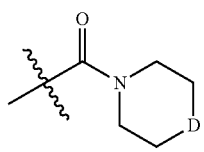

and D is $-N(R^C)-$ and $R^C$ is a substituted, branched or unbranched C1-C6 alkyl or D is $-S(=O)(=NR^D)-$ and $R^D$ is hydrogen or a substituted or unsubstituted, branched or unbranched C1-C6 alkyl, $-S-$, or $-S(O)-$.

In certain embodiments, D is $-N(R^C)-$ and $R^C$ is an oxo substituted C1-C6 alkyl. Suitably, $R^C$ may be $-C(O)CH_3$ or $-C(O)OC(CH_3)_3$.

In certain embodiments, D is $-N(R^C)-$ and $R^C$ is a hydroxyl substituted C1-C6 alkyl. Suitably, $R^C$ may be $-(CH_2)_3OH$.

In certain embodiments, D is $-N(R^C)-$ and $R^C$ is an amino substituted C1-C6 alkyl. Suitably, $R^C$ may be $-(CH_2)_3NH_2$.

In certain embodiments, D is $-S(=O)(=NR^D)-$ and $R^D$ is hydrogen or the substituted or unsubstituted, branched or unbranched C1-C6 alkyl, $-S-$, or $-S(O)-$. Suitably, D may be $-S(=O)(=NR^D)-$ and $R^D$ is hydrogen.

In particular embodiments of the invention, the substituent is selected from hydrogen, dimethylformamide, dimethylacetamide, 4-methyl-piperazine-1-carbonyl, piperazine-1-carbonyl, 4-(3-hydroxypropl)-piperazine-1-carbonyl, or 1-imino-1-oxo-1,4-thiazinane-4-carbonyl.

In some embodiments of the invention when $R^4$ comprises $-C(O)NRR'$, at least one of R and R' is the substituted or unsubstituted alkyl. Suitably, at least one of R and R' is $-CH_3$, an amino substituted C1-C6 alkyl, of a $-NHC(O)OC(CH_3)_3$ substituted alkyl. In particular embodiments, at least one of R and R' is $-CH_3$, an amino substituted C1-C6 alkyl, or a $-NHC(O)OC(CH_3)_3$ substituted alkyl. In particular embodiments, each of R and R' is the substituted or unsubstituted alkyl.

In a certain embodiment, the compounds are represented by Formula IA

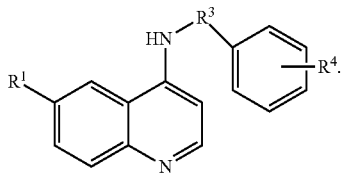

(Formula IA)

$R^1$ may be any of the radicals described above. In exemplary embodiments of the invention, $R^1$ may be selected from hydrogen, cyano, chloro, bromo, iodo, nitro, amino, or trifluoromethyl. $R^3$ may be an alkylene moiety comprising a substituted or unsubstituted, branched or unbranched C1-C6 alkylene. In exemplary embodiments of the invention, the alkylene moiety is a $-CH_2-$, $-CH_2CH_2-$, or $-CH_2CH_2CH_2-$. $R^4$ may be any of the aryl substituents described above. In exemplary embodiments, $R^4$ is hydrogen. In particular embodiments of the invention, the substituent is selected from hydrogen, dimethylformamide, dimethylacetamide, 4-methyl-piperazine-1-carbonyl, piperazine-1-carbonyl, 4-(3-hydroxypropl)-piperazine-1-carbonyl, or 1-imino-1-oxo-1,4-thiazinane-4-carbonyl.

In particular embodiments, the compounds are represented by Formula IAi

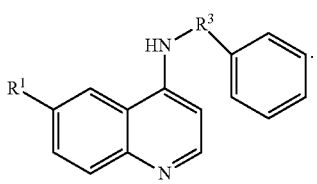

(Formula IAi)

$R^1$ may be any of the radicals described above. In exemplary embodiments of the invention, $R^1$ may be selected from hydrogen, cyano, chloro, bromo, iodo, nitro, amino, or trifluoromethyl. $R^3$ may be an alkylene moiety comprising a substituted or unsubstituted, branched or unbranched C1-C6 alkylene. In exemplary embodiments of the invention, the alkylene moiety is a $-CH_2-$, $-CH_2CH_2-$, or $-CH_2CH_2CH_2-$.

In a certain embodiment, the compounds are represented by Formula IB

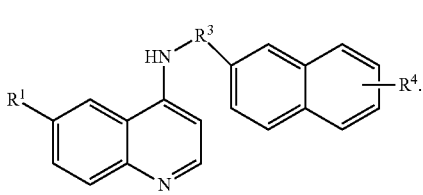

(Formula IB)

$R^1$ may be any of the radicals described above. In exemplary embodiments of the invention, $R^1$ may be selected from hydrogen, cyano, chloro, bromo, iodo, nitro, amino, or trifluoromethyl. $R^3$ may be an alkylene moiety comprising a substituted or unsubstituted, branched or unbranched C1-C6 alkylene. In exemplary embodiments of the invention, the alkylene moiety is a $-CH_2-$, $-CH_2CH_2-$, or $-CH_2CH_2CH_2-$. $R^4$ may be any of the aryl substituents described above. In exemplary embodiments, $R^4$ is hydrogen. In particular embodiments of the invention, the substituent is selected from hydrogen, dimethylformamide, dimethylacetamide, 4-methyl-piperazine-1-carbonyl, piperazine-1-carbonyl, 4-(3-hydroxypropl)-piperazine-1-carbonyl, or 1-imino-1-oxo-1,4-thiazinane-4-carbonyl.

In particular embodiments, the compounds are represented by Formula IBi

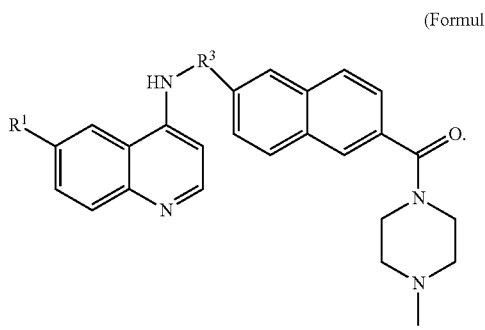

(Formula IBi)

$R^1$ may be any of the radicals described above. In exemplary embodiments of the invention, $R^1$ may be selected from hydrogen, cyano, chloro, bromo, iodo, nitro, amino, or trifluoromethyl. $R^3$ may be an alkylene moiety comprising a substituted or unsubstituted, branched or unbranched C1-C6 alkylene. In exemplary embodiments of the invention, the alkylene moiety is a —CH$_2$—, —CH$_2$CH$_2$—, or —CH$_2$CH$_2$CH$_2$—.

In a certain embodiment, the compounds are represented by Formula IC

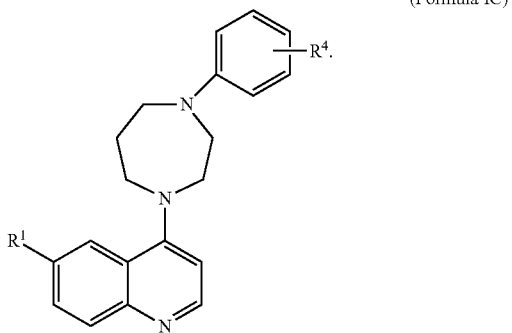

(Formula IC)

$R^1$ may be any of the radicals described above. In exemplary embodiments of the invention, $R^1$ may be selected from hydrogen, cyano, chloro, bromo, iodo, nitro, amino, or trifluoromethyl. $R^4$ may be any of the aryl substituents described above. In exemplary embodiments, $R^4$ is hydrogen. In particular embodiments of the invention, the substituent is selected from hydrogen, dimethylformamide, dimethylacetamide, 4-methyl-piperazine-1-carbonyl, piperazine-1-carbonyl, 4-(3-hydroxypropl)-piperazine-1-carbonyl, or 1-imino-1-oxo-1,4-thiazinane-4-carbonyl.

In a certain embodiment, the compounds are represented by Formula ICi

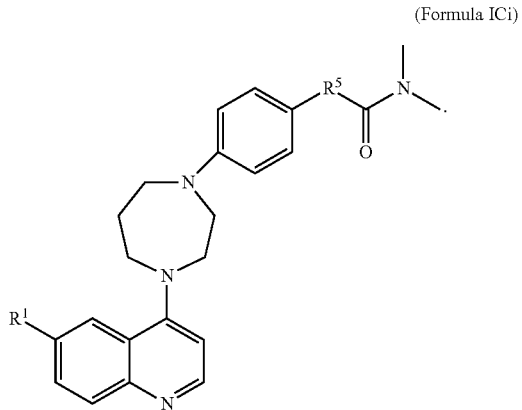

(Formula ICi)

$R^1$ may be any of the radicals described above. In exemplary embodiments of the invention, $R^1$ may be selected from hydrogen, cyano, chloro, bromo, iodo, nitro, amino, or trifluoromethyl. $R^5$ may be an alkylene moiety comprising a substituted or unsubstituted, branched or unbranched C1-C6 alkylene. In exemplary embodiments of the invention, the alkylene moiety is a —CH$_2$—, —CH$_2$CH$_2$—, or —CH$_2$CH$_2$CH$_2$—.

As used herein, an asterisk "*" or a plus sign "+" may be used to designate the point of attachment for any radical group or a substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like The term "heteroalkyl" as used herein refers to an "alkyl" group in which at least one carbon atom has been replaced with a heteroatom (e.g., an O, N, or S atom). Suitably, the heteroalkyl group may be an "alkoxyl" group, an "amino" group, or a "sulfanyl".

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom. The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —R$^1$C(O)N(R$^2$)—, —R$^1$C(O)N(R$^2$) R$^3$—, —C(O)NR$^2$R$^3$, or —C(O)NH$_2$, wherein R$^1$, R$^2$ and R$^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.)

Pharmaceutical Compositions

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 μM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches;

examples of binding agents are various celluloses and crosslinked polyvinylpyrrolidone, microcrystalline cellulose, such as Avicel® PH101 and Avicel® PH102, microcrystalline cellulose, and silicified microcrystalline cellulose (Pro-Solv SMCC™) Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists, which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions, which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form, which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that treats cancer activity may be administered as a single compound or in combination with another compound that treats cancer or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds, which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

Methods of Treatment

The compositions described are useful for treating a subject. As used herein, the terms "treating" or "to treat" each mean to alleviate symptoms, eliminate the causation of resultant symptoms either on a temporary or permanent basis, and/or to prevent or slow the appearance, or to reverse the progression or severity of resultant symptoms of the named disease or disorder. As such, the methods disclosed herein encompass both therapeutic and prophylactic administration.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the quinoline compounds disclosed herein. For example, a "subject in need of treatment" may include a subject having a CDK8-associated disease, disorder, or condition or a CDK19 associated disease, disorder, or condition such as cancer (such as prostate cancer, breast cancer, leukemia, or kidney cancer), inflammation-associated diseases, cardiovascular diseases, ribosomopathies, conditions characterized by reduced number of hematopoietic stem cells and/or progenitor cells, and bone anabolic disorders. CDK8/19-associated disease, disorder, or condition includes any disease, disorder, or condition the subject may be treated by the inhibition of CDK8 or CDK19.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a CDK8/19-associated disease.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Methods of Inhibiting CDK8 or CDK19

The compositions described are useful for inhibiting CDK8 and/or CDK19. As used herein, "inhibiting CDK8" or "inhibiting CDK19" means to inhibit the activity of CDK8 or CDK18, respectively, by any suitable mechanism, including competitive binding. The method of inhibiting CDK8 and/or CDK19 may comprise contacting any of the compounds or compositions described herein with CDK8 or CDK19. The extent of inhibition may be measured by the assays taught in the Examples in this Specification, including assay conditions employed by the service providers utilized herein. Results of these assays are commonly expressed herein as percent of control (POC), with the control being no compound being present. Alternatively, the results may be expressed as IC50. In some embodiments, the POC is less than 35%, suitably less than 30%, 25%, 20%, 15%, 10%, 5%, or 1% for an effective amount of any of the compounds of compositions described herein. In some embodiments, the IC50 is less than 2000 nM, 1500 nM, 1000 nM, 750 nM, 500 nM, 250 nM, 200 nM 150 nM, 100 nM, 75 nM, 50 nM, 40 nM, 30 nM, or 25 nM.

In some embodiments, the compounds and compositions disclosed herein specifically inhibit CDK8 or CDK19. As used herein, a compound or composition that "specifically inhibits CDK8" or "specifically inhibits CDK8" is a compound or composition that inhibits one or both CDK8 or CDK19, respectively, to a greater extent than it inhibits certain other CDKs. In some embodiments, such compounds further inhibit CDK8 and/or CDK19 to a greater extent than CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5. In preferred embodiments, such greater extent is at least 2-fold more, or at least 3-fold more, than CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Materials and Methods

All reagents were purchased from commercial sources and used without further purification unless otherwise noted. $^1$H, $^{13}$C NMR spectra were recorded on a Bruker spectrometer (300 MHz). Mass spectra was given with electric, electrospray (EI, ESI) produced by Agilent LC-MS spectrometer. Flash column chromatography: Biotage SNAP.

Scheme 1 General Synthesis of 6-$R_1$—N—$R_2$-quinolin-4-amine

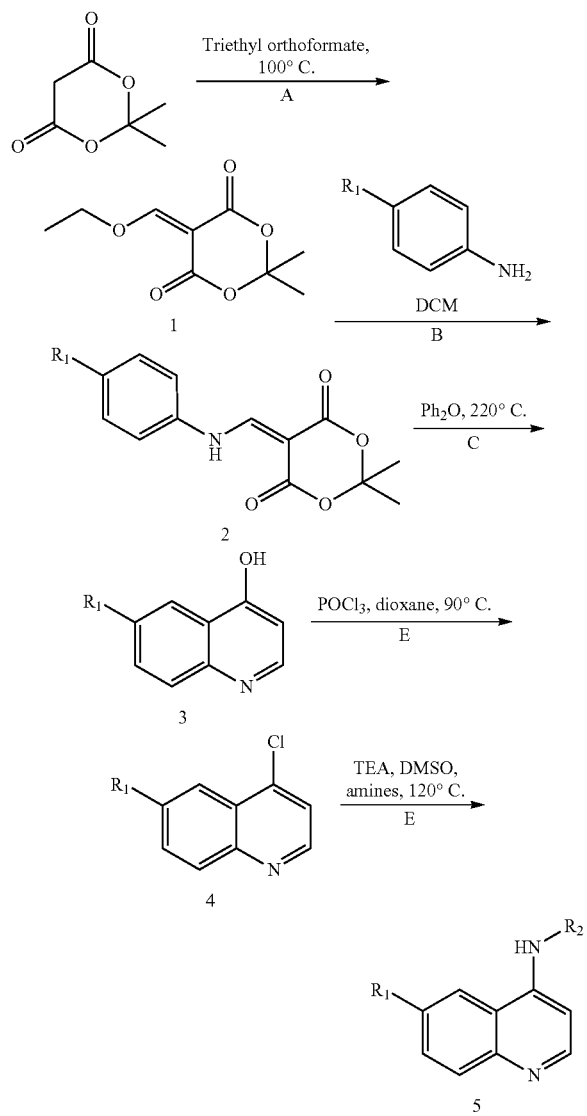

Synthesis of 5-(ethoxymethylene)-2,2-dimethyl-1,3-dioxane-4,6-dione (1)

The solution of 2,2-dimethyl-1,3-dioxane-4,6-dione (5 g, 34.7 mmol) in triethyl orthoformate (20.6 g, 139 mmol) was stirred at 100° C. for 1.5 h. Upon completion, the solvent was removed under reduced pressure to afford crude compound as yellow oil (7 g). The crude product was used for the next step directly without further purification.

Synthesis of 5-(((4-R-phenyl)amino)methylene)-2,2-dimethyl-1,3-dioxane-4,6-dione (2)

The solution of 4-R-benzonitrile (1 eq) and 5-(ethoxymethylene)-2,2-dimethyl-1,3-dioxane-4,6-dione (1) (2 eq) in dichloromethane. The mixture was stirred for 30 min at room temperature. Upon completion of the reaction, the resulting solid was filtered off and washed with hexane to provide the target compounds. The compounds were used without further purification.

Synthesis of 6-R-quinolin-4-ol (3)

A solution of compound 2 in phenoxybenzene was prepared. The mixture was stirred for 40 min at 220° C. The mixture was cooled to room temperature and hexane was added. The solids were collected by filtration and washed with hexane to provide the target compound. The compound was used without further purification.

4-hydroxyquinoline-6-carbonitrile (3a)

3a was prepared by the methods described above from 5-(((4-R-phenyl)amino)methylene)-2,2-dimethyl-1,3-dioxane-4,6-dione (2), where R is carbonitrile, to prepare a white solid (yield 65%). ESI-MS m/z: 171 ([M+H]$^+$).

6-bromoquinolin-4-ol (3b)

3b was prepared by the methods described above from 5-(((4-R-phenyl)amino)methylene)-2,2-dimethyl-1,3-dioxane-4,6-dione (2), where R is bromo, to prepare a white solid (yield 70%). ESI-MS m/z: 225 ([M+H]$^+$).

6-iodoquinolin-4-ol (3c)

3c was prepared by the methods described above from 5-(((4-R-phenyl)amino)methylene)-2,2-dimethyl-1,3-dioxane-4,6-dione (2), where R is iodo, to prepare a white solid (yield 73%). ESI-MS m/z: 272 ([M+H]$^+$).

6-chloroquinolin-4-ol (3d)

3d was prepared by the methods described above from 5-(((4-R-phenyl)amino)methylene)-2,2-dimethyl-1,3-dioxane-4,6-dione (2), where R is chloro, to prepare a brown solid (crude compound without further purification). ESI-MS m/z: 180 ([M+H]$^+$).

6-(trifluoromethyl)quinolin-4-ol (3e)

3e was prepared by the methods described above from 5-(((4-R-phenyl)amino)methylene)-2,2-dimethyl-1,3-dioxane-4,6-dione (2), where R is trifluoromethyl, to prepare a brown solid (yield 30%). ESI-MS m/z: 214 ([M+H]$^+$).

6-nitroquinolin-4-ol (3g)

3g was prepared by the methods described above from 5-(((4-R-phenyl)amino)methylene)-2,2-dimethyl-1,3-dioxane-4,6-dione (2), where R is nitro, to prepare a yellow solid (yield 65%). ESI-MS m/z: 191 ([M+H]$^+$).

General Synthesis of 6-R-4-chloroquinoline (4)

The solution of compound 3 (1 eq) in dioxane was added with phosphoryl chloride (5 eq). The mixture was stirred for 1.5 h at 90° C. The mixture was cooled to room temperature and condensed. Then the residue was diluted with water and the pH adjusted to 8 with saturated sodium carbonate solution. The mixture was extracted with ethyl acetate for three times, the organic layer was combined and dried over anhydrous sodium sulfate and concentrated under vacuum. The residue was purified by flash column chromatography.

4-chloroquinoline-6-carbonitrile (4a)

4a was prepared by the methods described above from 3a to prepare a white solid (yield 44%). $^1$H NMR (300 MHz, CDOD) δ: 8.94 (d, J=4.8 Hz, 1H), 8.76 (d, J=1.5 Hz, 1H), 8.24 (d, J=8.8 Hz, 2H), 8.07 (dd, J=1.8, 8.9 Hz, 1H), 7.82 (d, J=5.0 Hz, 1H); 13C NMR (125 MHz, CDOD) δ: 153.7, 149.4, 141.8, 131.6, 131.1, 130.5, 125.3, 123.2, 118.2, 110.8; ESI-MS m/z: 189 ([M+H]$^+$).

6-bromo-4-chloroquinoline (4b)

4b was prepared by the methods described above from 3b to prepare a yellow solid (yield 27%). ESI-MS m/z: 243 ([M+H]$^+$).

4-chloro-6-iodoquinoline (4c)

4c was prepared by the methods described above from 3c to prepare a yellow solid (yield 42%). ESI-MS m/z: 290 ([M+H]$^+$).

4,6-dichloroquinoline (4d)

4d was prepared by the methods described above from 3d to prepare a yellow solid (yield 47%). ESI-MS m/z: 199 ([M+H]$^+$).

4-chloro-6-(trifluoromethyl)quinoline (4e)

4e was prepared by the methods described above from 3e to prepare a brown solid (yield 31%). ESI-MS m/z: 232 ([M+H]$^+$).

4-chloroquinoline (4f)

4f was prepared by the methods described above from 3f to prepare a white solid (yield 86%). ESI-MS m/z: 164 ([M+H]$^+$).

4-chloro-6-nitroquinoline (4g)

4g was prepared by the methods described above from 3g to prepare a yellow solid (crude compound without further purification). ESI-MS m/z: 209 ([M+H]$^+$).

General Synthesis of 6-R$^1$—N—R$^2$-quinolin-4-amine (5)

The solution of compound 4 (1 eq), amine (1.5 eq), triethyl amine (3 eq) in DMSO was stirred overnight at 110° C. The mixture was cooled to room temperature and diluted with water. Then the mixture was extracted with ethyl acetate for three times, the organic layer was combined and dried over anhydrous sodium sulfate and concentrated in vacuum. The residue was purified by flash column chromatography.

4-(propylamino)quinoline-6-carbonitrile (5a-1) (SCCP ID: 6134)

5a-1 was prepared by the methods described above from 4a and propylamine to prepare a white solid (yield 12%). $^1$H-NMR (300 MHz, CD3OD): δ 8.68 (d, J=1.4 Hz, 1H), 8.44 (d, J=5.6 Hz, 1H), 7.85 (qd, J=1.4, 8.8 Hz, 2H), 6.60 (d, J=5.6 Hz, 1H), 3.35 (t, J=7.7 Hz, 2H), 1.79 (m, 2H), 1.06 (t, J=7.7 Hz, 3H). ESI-MS m/z: 212 ([M+H]$^+$).

4-(isopropylamino)quinoline-6-carbonitrile (5a-2) (SCCP ID: 6136)

5a-2 was prepared by the methods described above from 4a and isopropylamine to prepare a white solid (yield 23%). $^1$H-NMR (300 MHz, CD3OD): δ 8.76 (d, J=1.3 Hz, 1H), 8.44 (d, J=5.4 Hz, 1H), 7.84 (qd, J=1.6, 8.8 Hz, 2H), 6.64 (d, J=5.6 Hz, 1H), 3.96 (m, 1H), 1.36 (d, J=6.4 Hz, 6H). ESI-MS m/z: 212 ([M+H]$^+$).

4-(benzylamino)quinoline-6-carbonitrile (5a-3) (SCCP ID: 6138)

5a-3 was prepared by the methods described above from 4a and benzylamine to prepare a white solid (yield 37%). $^1$H-NMR (300 MHz, CD3OD): δ 8.74 (d, J=1.5 Hz, 1H), 8.36 (d, J=5.6 Hz, 1H), 7.87 (qd, J=1.6, 8.6 Hz, 2H), 7.30 (m, 5H), 6.51 (d, J=5.6 Hz, 1H), 4.64 (s, 2H). ESI-MS m/z: 260 ([M+H]$^+$).

4-(phenethylamino)quinoline-6-carbonitrile (5a-4) (SCCP ID: 6135)

5a-4 was prepared by the methods described above from 4a and phenylethylamine to prepare a white solid (yield 17%). $^1$H-NMR (300 MHz, CD3OD): δ 8.58 (d, J=1.4 Hz, 1H), 8.43 (d, J=5.8 Hz, 1H), 7.83 (qd, J=1.6, 9.0 Hz, 2H), 7.24 (m, 5H), 6.6 (d, J=5.9 Hz, 1H), 3.62 (d, J=7.2 Hz, 2H), 3.03 (d, J=7.2 Hz, 2H). ESI-MS m/z: 274 ([M+H]$^+$).

6-bromo-N-phenethylquinolin-4-amine (5b) (SCCP ID: 6146)

5b was prepared by the methods described above from 4b and phenylethylamine to prepare a yellow solid (yield 21%). $^1$H NMR (300 MHz, CDCl$_3$): 8.55 (d, J=5.3 Hz, 1H), 7.84 (d, J=9.0 Hz, 1H), 7.7 (d, J=2.0 Hz, 1H), 7.67 (dd, J=9.0, 2.0 Hz, 1H), 7.39-7.12 (m, 5H), 6.49 (d, J=5.3 Hz, 1H), 3.59 (q, J=5.5 Hz, 2H), 3.06 (t, J=6.8 Hz, 2H). ESI-MS m/z: 328 ([M+H]$^+$).

6-iodo-N-phenethylquinolin-4-amine (5c) (SCCP ID: 6147)

5c was prepared by the methods described above from 4c and phenylethylamine to prepare a light yellow solid (yield 13%). $^1$H NMR (300 MHz, CDCl$_3$): 8.53 (d, J=5.9 Hz, 1H), 7.99 (d, J=2.0 Hz, 1H), 7.83 (dd, J=9.0, 2.0 Hz, 1H), 7.69 (d, J=9 Hz, 1H), 7.31 (m, 5H), 6.43 (d, J=5.9 Hz, 1H), 3.59 (q, J=5.4 Hz, 2H), 3.05 (t, J=7.1 Hz, 2H). ESI-MS m/z: 375 ([M+H]$^+$).

6-chloro-N-phenethylquinolin-4-amine (5d) (SCCP ID: 6145)

5d was prepared by the methods described above from 4d and phenylethylamine to prepare a white solid (yield 6%). $^1$H NMR (300 MHz, CDCl$_3$): 8.55 (d, J=5.2 Hz, 1H), 7.94 (d, J=9.0 Hz, 1H), 7.56 (dd, J=9.0, 2.0 Hz, 2H), 7.39-7.28 (m, 5H), 6.43 (d, J=5.2 Hz, 1H), 3.61 (q, J=5.7 Hz, 2H), 3.07 (t, J=6.9 Hz, 2H). ESI-MS m/z: 283 ([M+H]$^+$).

N-phenethyl-6-(trifluoromethyl)quinolin-4-amine (5e) (SCCP ID: 6150)

5e was prepared by the methods described above from 4e and phenylethylamine to prepare a brown solid (yield 32%). $^1$H NMR (300 MHz, CDCl$_3$): 8.63 (d, J=5.8 Hz, 1H), 8.06 (d, J=8.5 Hz, 1H), 7.90 (s, 1H), 7.78 (dd, J=8.5, 1.7 Hz, 1H), 7.39-7.28 (m, 5H), 6.55 (d, J=5.8 Hz, 1H), 5.21 (m, 1H), 3.63 (q, J=7.2 Hz, 2H), 3.08 (t, J=7.2 Hz, 2H). ESI-MS m/z: 317 ([M+H]$^+$).

N-phenethylquinolin-4-amine (5f) (SCCP ID: 6161)

5f was prepared by the methods described above from 4f and phenylethylamine to prepare a white solid (yield 23%). $^1$H NMR (300 MHz, CDCl$_3$): 8.57 (d, J=5.3 Hz, 1H), 7.98 (d, J=8.9 Hz, 1H), 7.63 (d, J=7.6 Hz, 1H), 7.59 (d, J=7.6 Hz, 1H), 7.42-7.28 (m, 6H), 6.49 (d, J=5.3 Hz, 1H), 5.10 (s, 1H), 3.62 (q, J=6.7 Hz, 2H), 3.07 (t, J=6.7 Hz, 2H). ESI-MS m/z: 249 ([M+H$^+$]).

Scheme 2 Synthesis of 5g and 5h

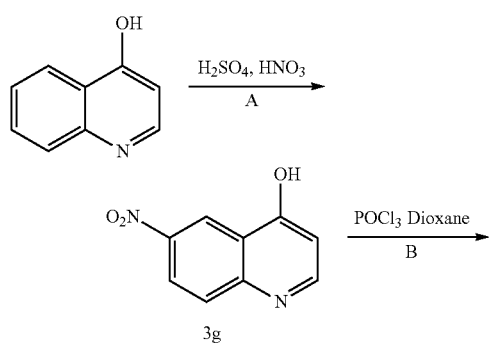

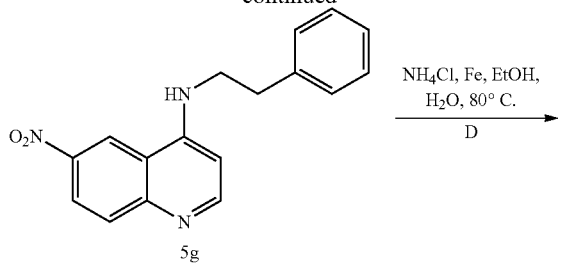

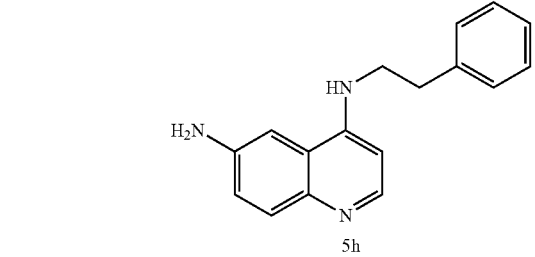

6-nitro-N-phenethylquinolin-4-amine (5g) (SCCP ID: 6149)

5g was prepared by the methods described above from 4g and phenylethylamine to prepare a yellow solid (yield 82%). $^1$H NMR (300 MHz, CDCl$_3$): 8.67 (d, J=5.6 Hz, 1H), 8.65 (d, J=2.5 Hz, 1H), 8.37 (d, J=9.3, 2.5 Hz, 1H), 8.04 (d, J=9.3 Hz, 1H), 7.41-7.29 (m, 5H), 6.58 (d, J=5.6 Hz, 1H), 3.66 (q, J=7.0 Hz, 2H), 3.06 (t, J=7.0 Hz, 2H). ESI-MS m/z: 294 ([M+H]$^+$).

N4-phenethylquinoline-4,6-diamine (5h) (SCCP ID: 6164)

5h was prepared by the methods described above from 5g as shown in scheme 2 to prepare a white solid (yield 84%). $^1$H NMR (300 MHz, CDCl$_3$): 8.37 (d, J=5.3 Hz, 1H), 7.80 (d, J=8.9 Hz, 1H), 7.38-7.24 (m, 5H), 7.06 (dd, J=8.9, 2.4 Hz, 1H), 6.68 (d, J=2.4 Hz, 1H), 6.41 (d, J=5.3 Hz, 1H), 4.74 (s, 1H), 3.86 (s, 2H), 3.58 (q, J=6.9 Hz, 2H), 3.04 (t=7.4 Hz, 2H). ESI-MS m/z: 264 ([M+H]$^+$).

Scheme 3 Synthesis pf 6-(cyanomethyl)-2-naphthoic acid

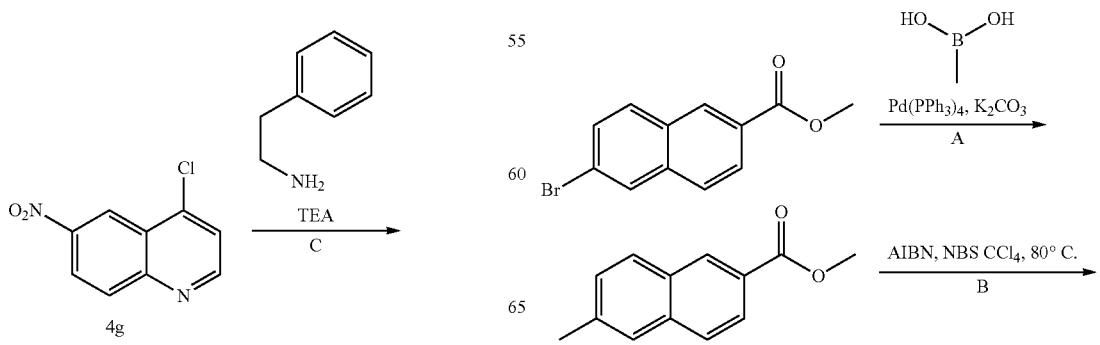

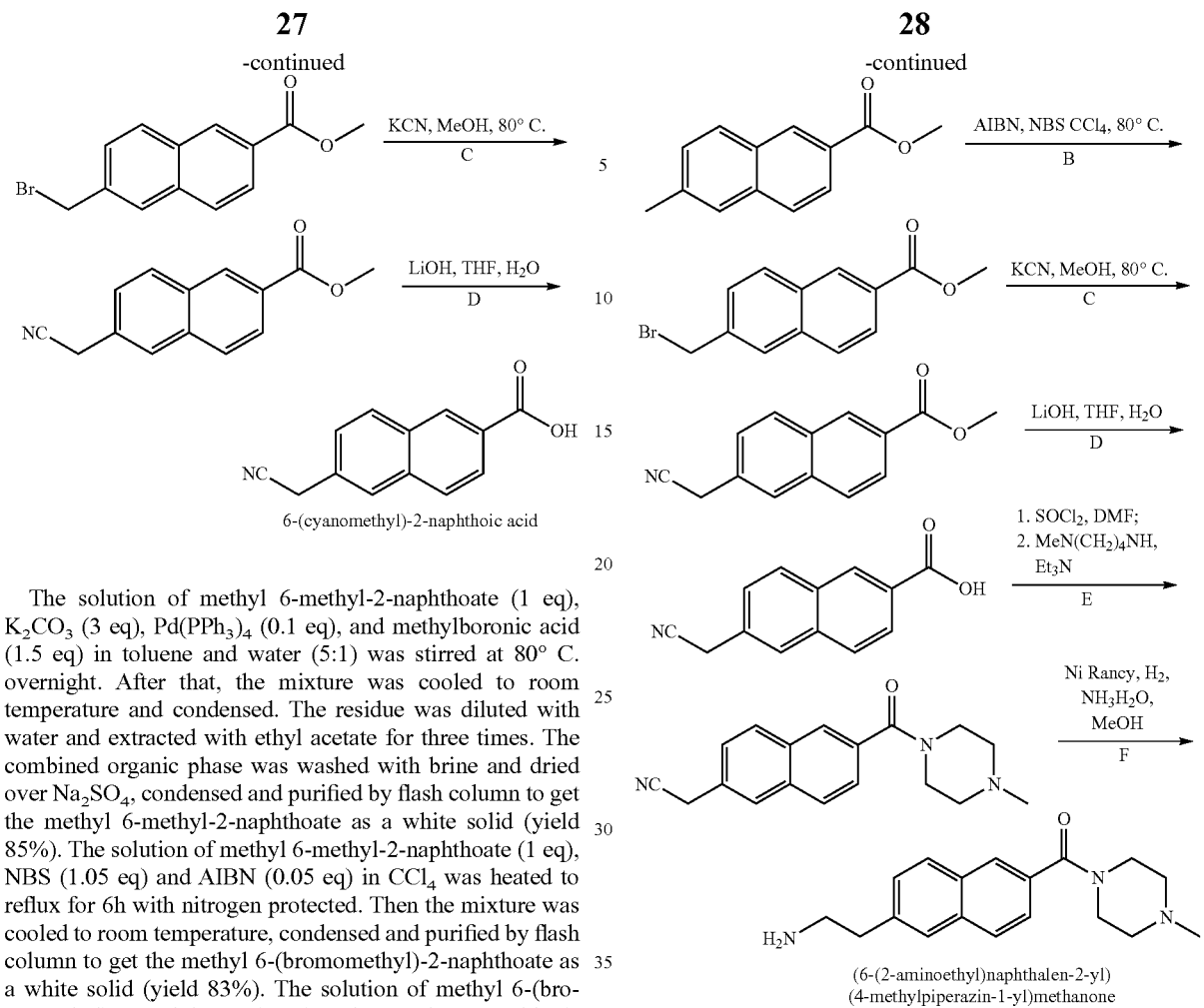

6-(cyanomethyl)-2-naphthoic acid

The solution of methyl 6-methyl-2-naphthoate (1 eq), $K_2CO_3$ (3 eq), Pd(PPh$_3$)$_4$ (0.1 eq), and methylboronic acid (1.5 eq) in toluene and water (5:1) was stirred at 80° C. overnight. After that, the mixture was cooled to room temperature and condensed. The residue was diluted with water and extracted with ethyl acetate for three times. The combined organic phase was washed with brine and dried over $Na_2SO_4$, condensed and purified by flash column to get the methyl 6-methyl-2-naphthoate as a white solid (yield 85%). The solution of methyl 6-methyl-2-naphthoate (1 eq), NBS (1.05 eq) and AIBN (0.05 eq) in $CCl_4$ was heated to reflux for 6h with nitrogen protected. Then the mixture was cooled to room temperature, condensed and purified by flash column to get the methyl 6-(bromomethyl)-2-naphthoate as a white solid (yield 83%). The solution of methyl 6-(bromomethyl)-2-naphthoate (1 eq) and potassium cyanide (3 eq) in methanol was heated to reflux until the starting material gone. The mixture was cooled to room temperature and condensed. Water was added and extracted with DCM for three times. The organic layer was dried with $Na_2SO_4$, condensed and purified by flash column to get the methyl 6-(cyanomethyl)-2-naphthoate as a white solid (yield 40%). The solution of methyl 6-(cyanomethyl)-2-naphthoate (1 eq), lithium hydroxide monohydrate (1.1 eq) in THF and water (1:1) was stirred at room temperature for 4h, condensed and dissolved in water. The solution was acidified with 1M HCl to pH=2. The solution was filtered and the filter cake was collected and washed with water until the pH to 7. The filter cake was dried to get the 6-(cyanomethyl)-2-naphthoic acid as a brown solid (yield 94%) and used without further purification;

Scheme 4 Synthesis of (6-(2-aminoethyl)naphthalen-2-yl)(4-methylpiperazin-1-yl)methanone

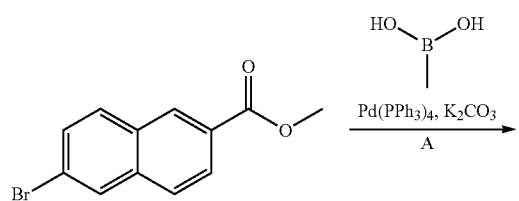

(6-(2-aminoethyl)naphthalen-2-yl)(4-methylpiperazin-1-yl)methanone

The solution of methyl 6-methyl-2-naphthoate (1 eq), $K_2CO_3$ (3 eq), Pd(PPh$_3$)$_4$ (0.1 eq), and methylboronic acid (1.5 eq) in toluene and water (5:1) was stirred at 80° C. overnight. After that, the mixture was cooled to room temperature and condensed. The residue was diluted with water and extracted with ethyl acetate for three times. The combined organic phase was washed with brine and dried over $Na_2SO_4$, condensed and purified by flash column to get the methyl 6-methyl-2-naphthoate as a white solid (yield 85%). The solution of methyl 6-methyl-2-naphthoate (1 eq), NBS (1.05 eq) and AIBN (0.05 eq) in $CCl_4$ was heated to reflux for 6h with nitrogen protected. Then the mixture was cooled to room temperature and condensed and purified by flash column to get the methyl 6-(bromomethyl)-2-naphthoate as a white solid (yield 83%). The solution of methyl 6-(bromomethyl)-2-naphthoate (1 eq) and potassium cyanide (3 eq) in methanol was heated to reflux until the starting material gone. The mixture was cooled to room temperature and condensed. Water was added and extracted with DCM for three times. The organic layer was dried with $Na_2SO_4$, condensed, and purified by flash column to get the methyl 6-(cyanomethyl)-2-naphthoate as a white solid (yield 40%). The solution of methyl 6-(cyanomethyl)-2-naphthoate (1 eq), lithium hydroxide monohydrate (1.1 eq) in THF and water (1:1) was stirred at room temperature for 4h, condensed and dissolved in water. The solution was acidified with 1M HCl to pH=2. The solution was filtered, and the filter cake was collected, washed with water until the pH to 7, and dried to get the 6-(cyanomethyl)-2-naphthoic acid as a brown solid (yield 94%) and used without further purification. The solution of 6-(cyanomethyl)-2-naphthoic acid (1 eq), SOCl₂ (3 eq), DMF (0.015 eq) in DCM was heated to reflux for 4 h with nitrogen protected. The mixture was cooled to room temperature and condensed. Toluene was added and condensed again to get the 6-(cyanomethyl)-2-naphthoyl chloride and used without further purification. The solution of 6-(cyanomethyl)-2-naphthoyl chloride (1 eq), 1-methylpiperazine (1.2 eq), TEA (3 eq) in DCM was stirred at room temperature for 1h, condensed, diluted with water, extracted with ethyl acetate, dried by Na₂SO₄, and purified by flash column to get the 2-(6-(4-methylpiperazine-1-carbonyl)naphthalen-2-yl)acetonitrile as light yellow oil (yield 91%). The solution of 2-(6-(4-methylpiperazine-1-carbonyl)naphthalen-2-yl)acetonitrile (1 eq), raney Ni (0.15 eq) in methanol, the same volume of 25% NH4OH (31 eq) aqueous solution was added. The mixture was degassed and then exchanged with hydrogen; the mixture was stirred at r.t. for 3 h. After that, the mixture was filtered to remove the catalyst, washed with ethanol, condensed, and water was added. The aqueous was extracted with DCM and then dried by Na₂SO₄ and purified by flash column to get the (6-(2-aminoethyl)naphthalen-2-yl)(4-methylpiperazin-1-yl)methanone (yield 95%). ESI-MS m/z: 298 ([M+H]⁺).

Synthesis of 4-((2-(6-(4-methylpiperazine-1-carbonyl)naphthalen-2-yl)ethyl)amino)quinoline-6-carbonitrile (5i) (SCCP ID: 6148)

The solution of (6-(2-aminoethyl)naphthalen-2-yl)(4-methylpiperazin-1-yl)methanone (1 eq), 4-chloroquinoline-6-carbonitrile (1 eq), triethyl amine (3 eq) in DMSO was stirred overnight at 110° C. The mixture was cooled to room temperature and diluted with water. Then the mixture was extracted with DCM for three times, the organic layer was combined and dried over anhydrous sodium sulfate and concentrated in vacuum. The residue was purified by flash column chromatography. A light yellow solid (yield 63%). ¹H NMR (300 MHz, CDCl₃): 8.36 (d, J=5.6 Hz, 1H), 8.11 (s, 1H), 8.03 (d, J=8.4 Hz, 1H), 7.90 (s, 1H), 7.85 (d, J=8.7 Hz, 1H), 7.81 (d, J=8.7 Hz, 1H), 7.75 (dd, J=8.4, 1.9 Hz, 1H), 7.66 (s, 1H), 7.51 (dd, J=8.4, 1.5 Hz, 1H), 7.40 (dd, J=8.4, 1.5 Hz, 1H), 6.59 (d, J=5.6 Hz, 1H), 3.88 (s, 2H), 3.68 (m, 2H), 3.53 (s, 2H), 3.21 (t, J=6.9 Hz, 2H), 2.54 (s, 2H), 2.41 (s, 2H), 2.35 (s, 3H). ESI-MS m/z: 450 ([M+H]⁺).

Scheme 5 Synthesis of 4-((2-(6-(4-(3-hydroxypropyl)piperazine-1-carbonyl)naphthalen-2-yl)ethyl)amino)quinoline-6-carbonitrile (SCCP ID: 6216)

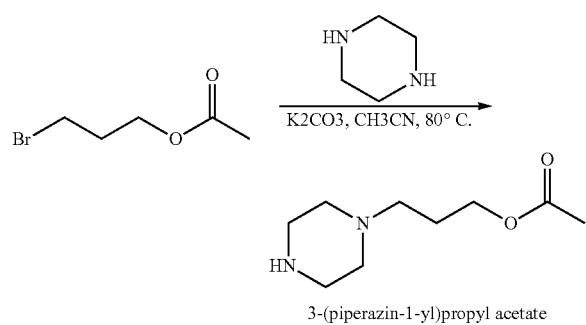

3-(piperazin-1-yl)propyl acetate

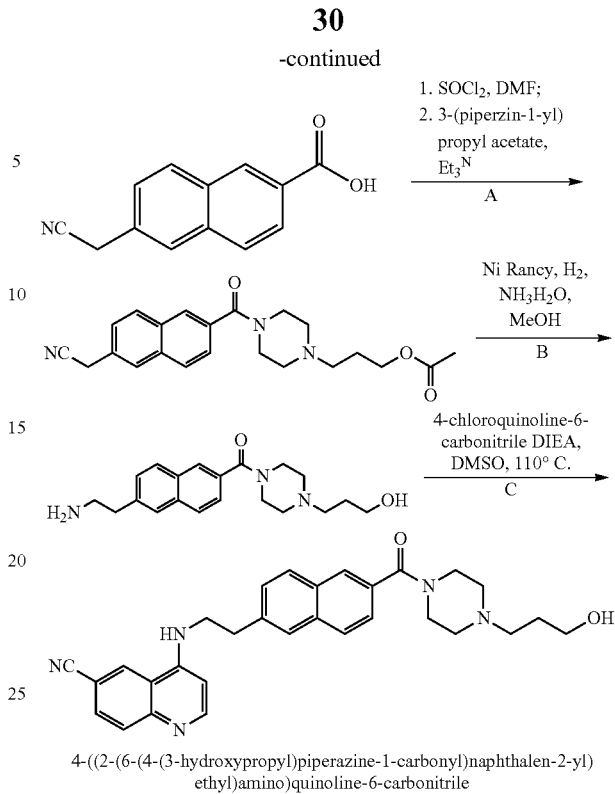

4-((2-(6-(4-(3-hydroxypropyl)piperazine-1-carbonyl)naphthalen-2-yl)ethyl)amino)quinoline-6-carbonitrile The solution of 3-bromopropyl acetate (1 eq), piperazine (3 eq), K₂CO₃ (3 eq) in CH₃CN was stirred at 80° C. for overnight. After that the mixture was cooled to room temperature and condensed. Then water was added, and the mixture was extracted with DCM for three times. The organic layers were combined and washed with sat NaCl aq, dried by Na₂SO₄, condensed, and purified by flash column to afford 3-piperazin-1-ylpropyl acetate (yield 32%). The solution of 6-(cyanomethyl)-2-naphthoic acid (1 eq), SOCl₂ (3 eq), DMF (0.015 eq) in DCM was heated to reflux for 4 h with nitrogen protected. After that the mixture was cooled to room temperature and condensed. Then toluene was added and condensed again to get the 6-(cyanomethyl)-2-naphthoyl chloride and used without further purification. The solution of 6-(cyanomethyl)-2-naphthoyl chloride (1 eq), 3-piperazin-1-ylpropyl acetate (1 eq), TEA (3 eq) in DCM was stirred at room temperature for 1h, condensed, diluted with water, extracted with ethyl acetate, dried by Na₂SO₄, and purified by flash column to get the 3-(4-(6-(cyanomethyl)-2-naphthoyl)piperazin-1-yl)propyl acetate (yield 45%). To a solution of 3-(4-(6-(cyanomethyl)-2-naphthoyl)piperazin-1-yl)propyl acetate (1 eq) and raney Ni (0.15 eq) in methanol, the same volume of 25% NH₄OH (31 eq) aqueous solution was added. The mixture was degassed and then exchanged with hydrogen; the mixture was stirred at r.t. for overnight. After that, the mixture was filtered to remove the catalyst, and then washed with the filter with ethanol, condense the mixture, dried to get the (6-(2-aminoethyl)naphthalen-2-yl)(4-(3-hydroxypropyl)piperazin-1-yl)methanone and used for the next step without further purification (yield 79%). The solution of (6-(2-aminoethyl)naphthalen-2-yl)(4-(3-hydroxypropyl)piperazin-1-yl)methanone (1 eq), 4-chloroquinoline-6-carbonitrile (1 eq), DIEA (3 eq) in DMSO was stirred overnight at 110° C. The mixture was cooled to room temperature and diluted with water. Then the mixture was extracted with DCM three times. The organic layer was combined and dried over anhydrous sodium sulfate and concentrated in vacuum. The residue was purified by flash column chromatography to get the 4-((2-(6-(4-(3-hydroxypropyl)piperazine-1-carbonyl) naphthalen-2-yl)ethyl)amino)quinoline-6-carbonitrile (yield 20%). ESI-MS m/z: 494 ([M+H]$^+$). $^1$H NMR, CDCl$_3$, 8.61 (d, J=5.4 Hz, 1H), 8.20 (s, 1H), 8.01 (d, J=8.8 Hz, 2H), 7.88 (s, 1H), 7.81 (t, J=9.3 Hz, 2H), 7.73 (d, J=8.3 Hz, 1H), 7.63 (s, 1H), 7.49 (d, J=8.3 Hz, 1H), 7.38 (d, J=8.8 Hz, 1H), 6.57 (d, J=5.4 Hz, 1H), 3.85 (m, 2H), 3.81 (t, J=4.9 Hz, 2H), 3.68 (m, 2H), 3.67 (q, J=6.0 Hz, 2H),), 3.19 (t, J=6.5 Hz, 2H), 2.66 (t, J=5.4 Hz, 2H), 2.50 (m, 4H), 1.75 (m, 2H).

Scheme 6 Synthesis of 4-((2-(6-(piperazine-1-carbonyl)naphthalen-2-yl)ethyl)amino)quinoline-6-carbonitrile (SCCP ID: 6283)

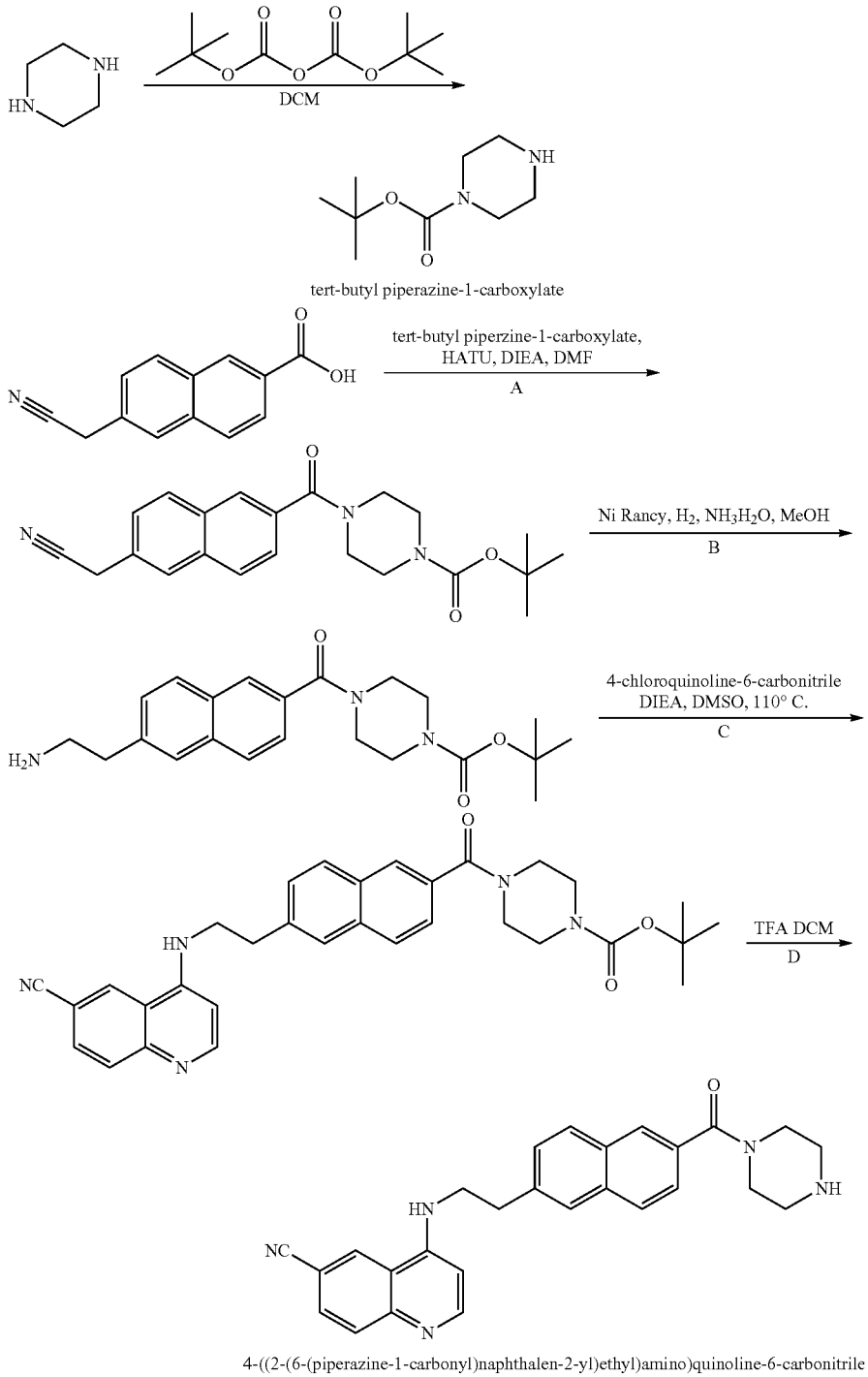

4-((2-(6-(piperazine-1-carbonyl)naphthalen-2-yl)ethyl)amino)quinoline-6-carbonitrile The solution of piperazine (1 eq) in DCM was cooled to 0° C. and then tert-butoxycarbonyl tert-butyl carbonate (0.5 eq) in DCM was added dropwise. The mixture was stirred at 0° C. for 30 min, then allowed to stir at r.t. for overnight. After that, the mixture was filtered and the solution was condensed and water was added. The mixture was filtered again to remove the solid. After that, K$_2$CO$_3$ was added to the water phase and extracted with ether three times. The organic layers were combined and dried by Na$_2$SO$_4$ and condensed to get the tert-butyl piperazine-1-carboxylate (yield 39%), which was used without further purification. The solution of 6-(cyanomethyl)-2-naphthoic acid (1 eq), HATU (1.5 eq), DIEA (2 eq) in DMF was stirred at r.t. for 15 min, then tert-butyl piperazine-1-carboxylate was added and the mixture and stirred at r.t. for 4h. After that, water was added and extracted with DCM. The organic layers were combined and washed with sat NaHCO$_3$ aq and brine and dried by Na$_2$SO$_4$, then condensed and purified by flash column to get the tert-butyl 4-(6-(cyanomethyl)-2-naphthoyl)piperazine-1-carboxylate (yield 61%). To a solution of tert-butyl 4-(6-(cyanomethyl)-2-naphthoyl)piperazine-1-carboxylate (1 eq), raney Ni (0.15 eq) in methanol, the same volume of 25% NH$_4$OH (31 eq) aqueous solution was added. The mixture was degassed and then exchanged with hydrogen. The mixture was stirred at r.t. for overnight. After that, the mixture was filtered to remove the catalyst and then washed with the filter with ethanol, condense the mixture, dried to get the tert-butyl 4-(6-(2-aminoethyl)-2-naphthoyl)piperazine-1-carboxylate and used for the next step without further purification. The solution of tert-butyl 4-(6-(2-aminoethyl)-2-naphthoyl)piperazine-1-carboxylate (1 eq), 4-chloroquinoline-6-carbonitrile (1 eq), DIEA (3 eq) in DMSO was stirred overnight at 110° C. The mixture was cooled to room temperature and diluted with water. Then the mixture was extracted with DCM three times. The organic layer was combined and dried over anhydrous sodium sulfate and concentrated in vacuum. The residue was purified by flash column chromatography to get the tert-butyl 4-(6-(2-((6-cyanoquinolin-4-yl)amino)ethyl)-2-naphthoyl)piperazine-1-carboxylate (yield 43%). The solution of tert-butyl 4-(6-(2-((6-cyanoquinolin-4-yl)amino)ethyl)-2-naphthoyl)piperazine-1-carboxylate (1 eq) in DCM was mixed with TFA (10 eq) and stirred at r.t. for 2h. After that, the mixture was condensed and purified by flash column to get the 4-((2-(6-(piperazine-1-carbonyl)naphthalen-2-yl)ethyl)amino)quinoline-6-carbonitrile (yield 62%). ESI-MS m/z: 436 ([M+H]$^+$). $^1$H NMR, DMSO-d6, 9.62 (s, 1H), 8.62 (d, J=7.3 Hz, 1H), 8.27 (dd, J=8.7, 1.3 Hz, 1H), 8.04-7.90 (m, 5H), 7.61 (dd, J=8.4, 1.3 Hz), 7.55 (dd, J=8.4, 1.3 Hz, 1H), 7.09 (d, J=7.3 Hz, 1H), 3.94 (q, J=6.6 Hz, 2H), 3.73 (m, 4H), 3.21 (m, 6H).

Scheme 7 Synthesis of 6-(2-aminoethyl)-N,N-dimethyl-2-naphthamide

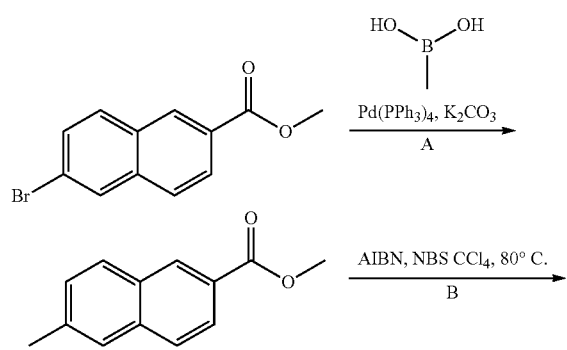

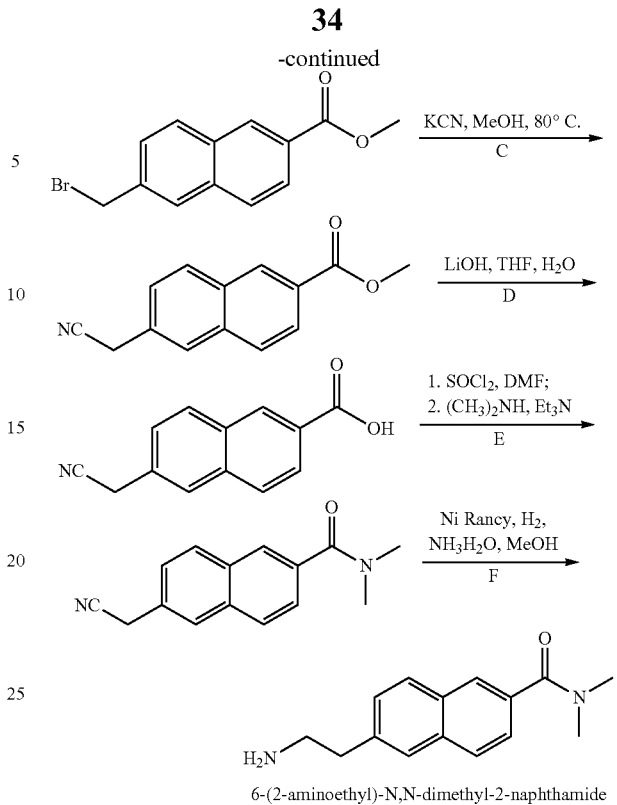

6-(2-aminoethyl)-N,N-dimethyl-2-naphthamide

The solution of methyl 6-methyl-2-naphthoate (1 eq), K$_2$CO$_3$ (3 eq), Pd(PPh$_3$)$_4$ (0.1 eq), and methylboronic acid (1.5 eq) in toluene and water (5:1) was stirred at 80° C. overnight. After that, the mixture was cooled to room temperature and condensed. The residue was diluted with water and extracted with ethyl acetate for three times. The combined organic phase was washed with brine and dried over Na$_2$SO$_4$, condensed and purified by flash column to get the methyl 6-methyl-2-naphthoate as a white solid (yield 85%). The solution of methyl 6-methyl-2-naphthoate (1 eq), NBS (1.05 eq) and AIBN (0.05 eq) in CCl$_4$ was heated to reflux for 6h with the nitrogen protected. Then the mixture was cooled to room temperature, condensed and purified by flash column to get the methyl 6-(bromomethyl)-2-naphthoate as a white solid (yield 83%). The solution of methyl 6-(bromomethyl)-2-naphthoate (1 eq) and potassium cyanide (3 eq) in methanil was heated to reflux until the starting material gone. The mixture was cooled to room temperature and condensed, water was added, and extracted with DCM three times. The organic layer was dried with Na$_2$SO$_4$, condensed, and purified by flash column to get the methyl 6-(cyanomethyl)-2-naphthoate as a white solid (yield 40%). The solution of methyl 6-(cyanomethyl)-2-naphthoate (1 eq), lithium hydroxide monohydrate (1.1 eq) in THF and water (1:1) was stirred at room temperature for 4h, condensed, and dissolved in water. The solution was acidified with 1M HCl to pH=2. The solution was filtered and the filter cake was collected and washed with water until the pH to 7. The filter cake was dried to get the 6-(cyanomethyl)-2-naphthoic acid as a brown solid (yield 94%) and used without further purification; The solution of 6-(cyanomethyl)-2-naphthoic acid (1 eq), SOCl$_2$ (3 eq), DMF (0.015 eq) in DCM was heated to reflux for 4 h with the nitrogen protected. After that the mixture was cooled to room temperature and condensed. Then toluene was added and condensed again to get the 6-(cyanomethyl)-2-naphthoyl chloride and used without further purification. The solution of 6-(cyanomethyl)-2-naphthoyl chloride (1 eq), dimethylamine (1.2 eq), TEA (3 eq) in DCM was stirred at room temperature for 1h, condensed, diluted with water, extracted with ethyl acetate, dried by $Na_2SO_4$, and purified by flash column to get the 6-(cyanomethyl)-N,N-dimethyl-2-naphthamide as yellow oil (yield 78%). To a solution of 6-(cyanomethyl)-N,N-dimethyl-2-naphthamide (1 eq), raney Ni (0.15 eq) in methanol, the same volume of 25% $NH_4OH$ (31 eq) aqueous solution was added. The mixture was degassed and then exchanged with hydrogen. The mixture was stirred at r.t. for overnight. After that, the mixture was filtered to remove the catalyst, then washed with ethanol, condensed, dried and used for the next step without further purification (yield 71%). ESI-MS m/z: 243 ([M+H]$^+$).

Scheme 8 Synthesis of 6-(2-((6-cyanoquinolin-4-yl)amino)ethyl)-N,N-dimethyl-2-naphthamide (SCCP ID: 6219)

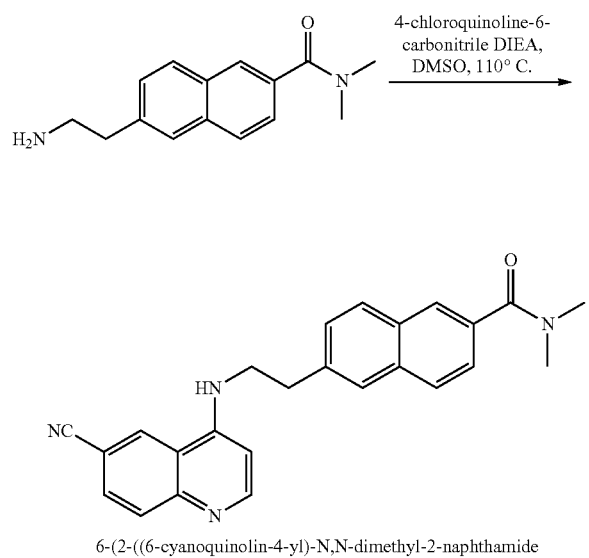 [SMILES: CN(C)C(=O)c1ccc2cc(CCN)ccc2c1 ; CN(C)C(=O)c1ccc2cc(CCNc3ccnc4ccc(C#N)cc34)ccc2c1]

6-(2-((6-cyanoquinolin-4-yl)-N,N-dimethyl-2-naphthamide

The solution of 6-(2-aminoethyl)-N,N-dimethyl-2-naphthamide (1 eq), 4-chloroquinoline-6-carbonitrile (1 eq), DIEA (3 eq) in DMSO was stirred overnight at 110° C. The mixture was cooled to room temperature and diluted with water. Then the mixture was extracted with DCM for three times, the organic layer was combined and dried over anhydrous sodium sulfate and concentrated in vacuum. The residue was purified by flash column chromatography to get the 6-(2-((6-cyanoquinolin-4-yl)amino)ethyl)-N,N-dimethyl-2-naphthamide (yield 77%). ESI-MS m/z: 395 ([M+H]$^+$); $^1$H NMR (300 MHz, $CD_3OD$): δ 8.60 (d, J=1.4 Hz, 1H), 8.45 (d, J=5.9 Hz, 1H), 7.91-7.80 (m, 6H), 7.53 (dd, J=8.2, 1.8 Hz, 1H), 7.48 (dd, J=8.2, 1.8 Hz, 1H), 7.74 (dd, J=8.6, 1.8 Hz, 1H), 6.71 (d, J=5.9 Hz, 1H), 3.76 (t, J=7.1 Hz, 2H), 3.24 (t, J=7.1 Hz, 2H), 3.15 (s, 3H), 3.05 (s, 3H).

Scheme 9 Synthesis of 4-(1,4-diazepan-1-yl)-N,N-dimethylbenzamide and 2-(4-(1,4-diazepan-1-yl)phenyl)-N,N-dimethylacetamide

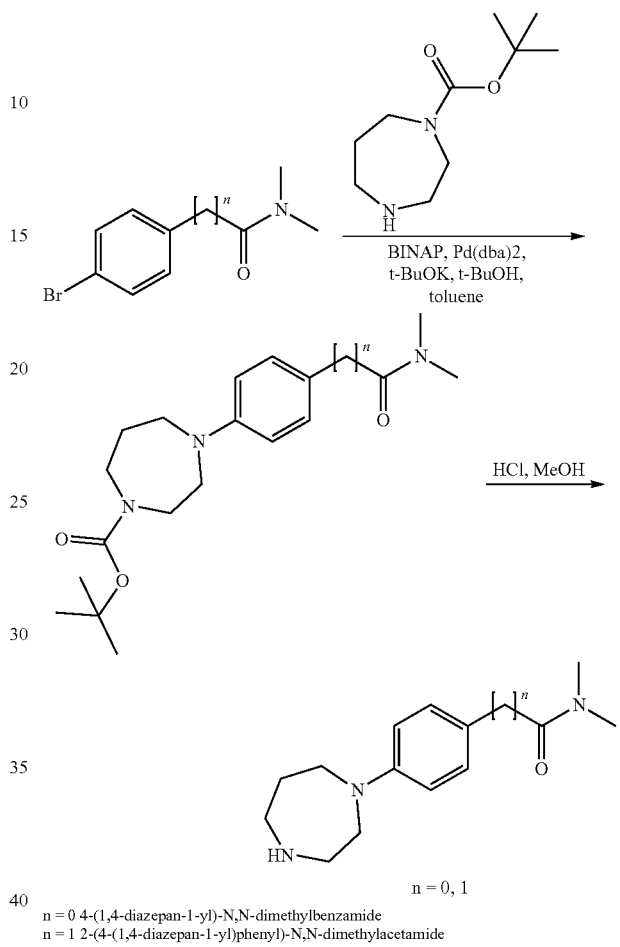

n = 0, 1
n = 0 4-(1,4-diazepan-1-yl)-N,N-dimethylbenzamide
n = 1 2-(4-(1,4-diazepan-1-yl)phenyl)-N,N-dimethylacetamide Synthesis of 4-(1,4-diazepan-1-yl)-N,N-dimethylbenzamide The solution of 4-bromo-N,N-dimethylbenzamide (1 eq), tert-butyl 1,4-diazepane-1-carboxylate (1.2 eq), t-BuOK (1.5 eq), Tris(dibenzylideneacetone)dipalladium(0) (0.05 eq), and davephos (0.15 eq) in t-BuOH and 1,4-dioxane (1:2) was refluxed for 2h. After that, the mixture was cooled to room temperature and condensed. The residue was diluted with water and extracted with ethyl acetate three times. The combined organic phase was washed with brine and dried over $Na_2SO_4$, condensed, and purified by flash column to get the tert-butyl 4-(4-(dimethylcarbamoyl)phenyl)-1,4-diazepane-1-carboxylate (yield 42%). The solution of tert-butyl 4-(4-(dimethylcarbamoyl)phenyl)-1,4-diazepane-1-carboxylate (1 eq) in methanol and the same volume of 1N HCl in dioxane was added. The mixture was stirred at room temperature for 2h. The mixture was neutralized by 1N NaOH aqueous solution and then extracted with DCM. The original layer was washed with brine, dried, condensed and purified by flash column to get the 4-(1,4-diazepan-1-yl)-N,N-dimethylbenzamide as white solid (yield 60%). ESI-MS m/z: 248 ([M+H]$^+$).

4-(4-(6-cyanoquinolin-4-yl)-1,4-diazepan-1-yl)-N,N-dimethylbenzamide (5j) (SCCP ID: 6168)

5j was prepared by the methods described above from 4a and 4-(1,4-diazepan-1-yl)-N,N-dimethylbenzamide to prepare a white solid (yield 43%). ¹H NMR (300 MHz, CDCl3): 8.74 (d, J=5.3 Hz, 1H), 8.41 (d, J=1.6 Hz, 1H), 8.11 (d, J=8.7 Hz, 1H), 7.79 (dd, J=8.7, 1.6 Hz, 1H), 7.40 (d, J=8.7 Hz, 2H), 6.94 (d, J=5.3 Hz, 1H), 6.75 (d, J=8.7 Hz, 2H), 3.87 (t, J=4.8 Hz, 2H), 3.77 (t, J=6.1 Hz, 2H), 3.62 (t, J=5.0 Hz, 2H), 3.44 (t, J=5.0 Hz, 2H), 3.07 (s, 6H), 2.31 (m, 2H). ESI-MS m/z: 400 ([M+H]⁺).

Synthesis of 2-(4-(1,4-diazepan-1-yl)phenyl)-N,N-dimethylacetamide

The synthesis method is the same as 4-(1,4-diazepan-1-yl)-N,N-dimethylbenzamide, replacing 4-bromo-N,N-dimethylbenzamide with 2-(4-Bromophenyl)-N,N-dimethylacetamide. As a white solid (yield 54%). ESI-MS m/z: 262 ([M+H]⁺).

2-(4-(4-(6-cyanoquinolin-4-yl)-1,4-diazepan-1-yl)phenyl)-N,N-dimethylacetamide (5k) (SCCP ID: 6160)

5k was prepared by the methods described above from 4a and 2-(4-(1,4-diazepan-1-yl)phenyl)-N,N-dimethylacetamide to prepare a white solid (yield 49%). ¹H NMR (300 MHz, CDCl₃): 8.73 (d, J=5.2 Hz, 1H), 8.40 (d, J=1.4 Hz, 1H), 8.08 (d, J=8.7 Hz, 1H), 7.77 (dd, J=8.7, 1.4 Hz, 1H), 7.14 (d, J=8.6 Hz, 2H), 6.92 (d, J=5.2 Hz, 1H), 6.74 (d, J=8.6 Hz, 2H), 3.82 (t, J=5.2 Hz, 2H), 3.70 (t, J=6.5 Hz, 2H), 3.62 (s, 2H), 3.60 (t, J=4.8 Hz, 2H), 3.44 (t, J=5.6 Hz, 2H), 3.01 (s, 3H), 2.96 (s, 3H), 2.29 (m, 2H). ESI-MS m/z: 414 ([M+H]⁺).

Synthesis of 4-((2-(6-substituted-naphthalen-2-yl)ethyl)amino)quinoline-6-carbonitrile Derivatives 4-((2-(6-substituted-naphthalen-2-yl)ethyl)amino)quinoline-6-carbonitrile derivatives were prepared according to Schemes 10 and 11.

Scheme 10. Synthesis of 6-substituted-N-phenethylquinolin-4-amine Derivatives Reagents and Conditions: (a) triethoxymethane, 100° C.; (b) p-substituted aniline, DCM, r.t.; (c) phenoxybenzene, 220° C.; (d) POCl₃, 1,4-dioxane, 90° C.

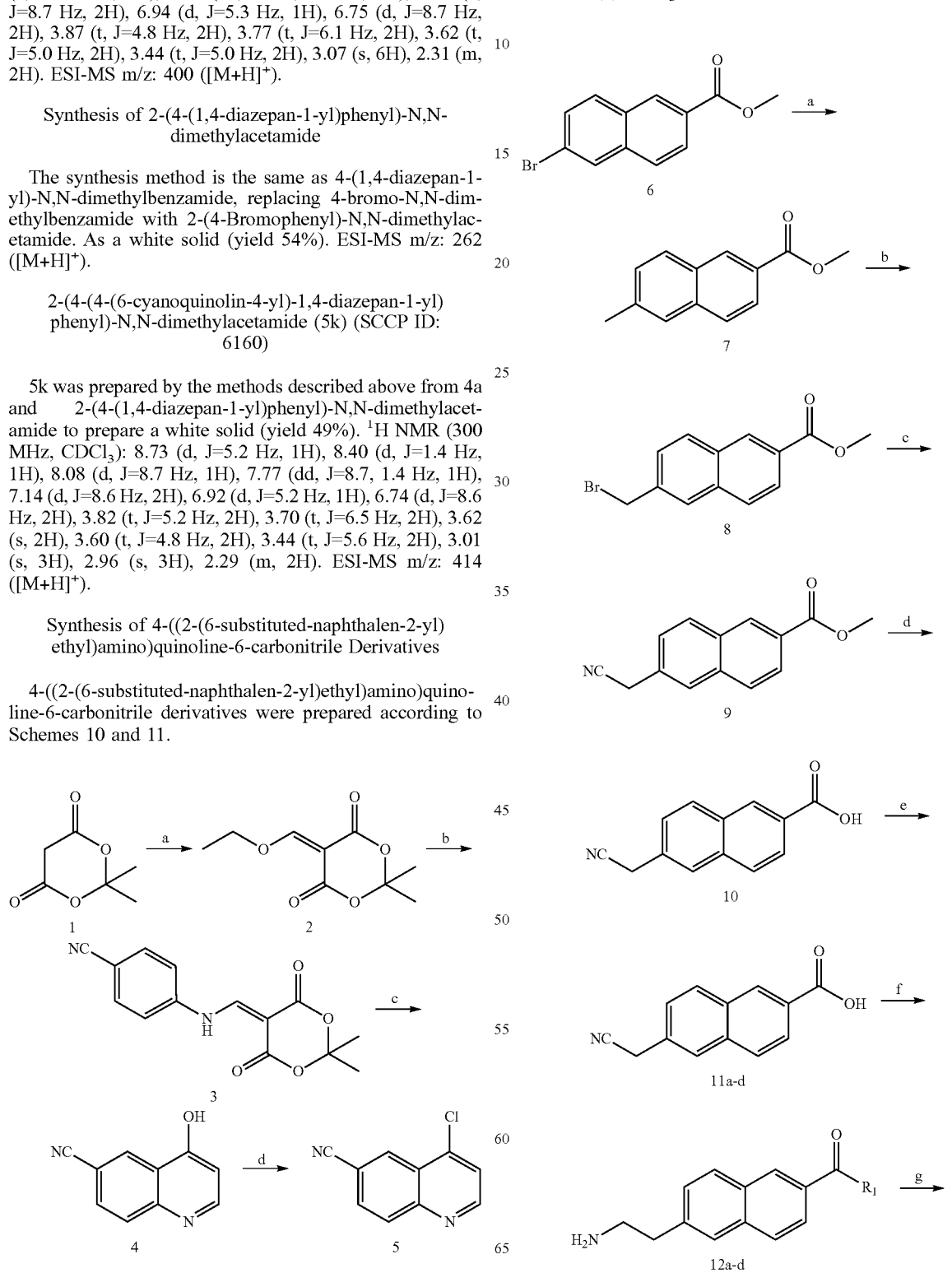

-continued

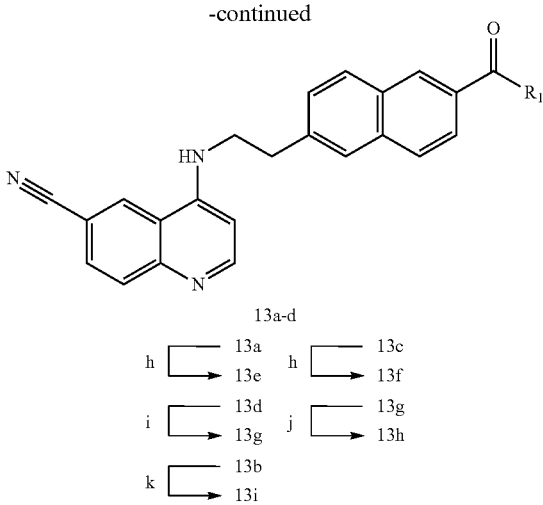

13a-d h [ 13a → 13e ]   h [ 13c → 13f ]
i [ 13d → 13g ]   j [ 13g → 13h ]
k [ 13b → 13i ]

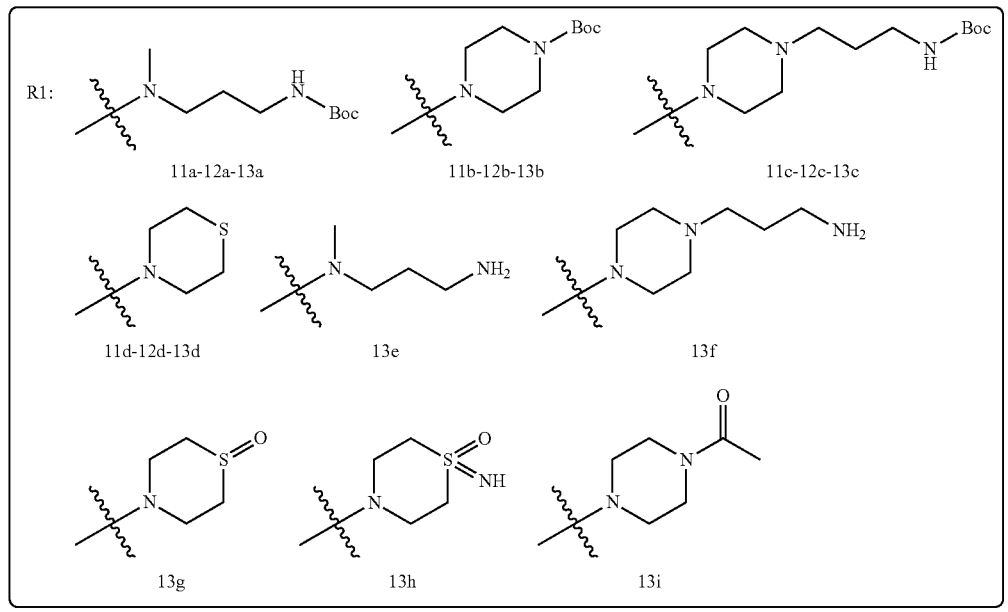

Scheme 11. Synthesis of 4-((2-(6-substituted-naphthalen-2-yl)ethyl)amino)quinoline-6-carbonitrile Derivatives Reagents and conditions: (a) Pd(PPh$_3$)$_4$, K$_2$CO$_3$, toluene, water, 80° C., 92%; (b) NBS, AIBN, CCl$_4$, reflux, 83% for 12; NCS, AIBN, DCE, 80° C., 40% for 13; (c) KCN, MeOH, reflux, 40%; (d) LiOH, THF, water, 93% for 15, 95%; (e) HATU, DIEA, DCM/DMF, r.t., 40-70%; (f) Raney Ni, MeOH/H$_2$O/NH$_4$OH, H2, r.t., 70-90%; (g) 4-chloroquinoline-6-carbonitrile, DIEA, DMSO, 120° C., 20-75%; (h) TFA, DCM, r.t., 85-95%; (i) NaIO$_4$, MeOH, H$_2$O, r.t., 73%; (j) Rhodium acetate dimer, iodozbenzene diacetate, 2,2,2-trifluoroacetamide, MgO, DCM, r.t, 53%; (k) TFA, DCM, r.t.; acetyl chloride, DIEA, DCM, 0° C. to r.t., 91%.

5-(ethoxymethylene)-2,2-dimethyl-1,3-dioxane-4,6-dione (2): To a 100 mL flask was added 2,2-dimethyl-1,3-dioxane-4,6-dione (34.7 mmol, 5 g), and 5-(ethoxymethylene)-2,2-dimethyl-1,3-dioxane-4,6-dione (35 mmol, 7 g). The mixture was stirred at 100° C. for 1.5h. Upon completion, the mixture was condensed via rotavap. The resulted light-yellow solid residue was 5-(ethoxymethylene)-2,2-dimethyl-1,3-dioxane-4,6-dione (6.5 g, 94% yield) and used for the next step without further purification.

4-[(2,2-dimethyl-4,6-dioxo-1,3-dioxan-5-ylidene)methylamino]benzonitrile (3): To a 100 mL round bottom flask was charged with a solution of 4-aminobenzonitrile (17.5 mmol, 2.07 g) in DCM (80 mL). This was followed by adding 5-(ethoxymethylene)-2,2-dimethyl-1,3-dioxane-4,6-dione (32.5 mmol, 6.5g) in DCM (20 mL). The resulting solution was at room temperature for 30 min. Upon completion, the resulting solid was filtered off and washed with hexane to give the target compound 4-[(2,2-dimethyl-4,6-dioxo-1,3-dioxan-5-ylidene)methylamino]benzonitrile as a white solid (3.7 g, 40% yield) and used without further purification. ESI-MS m/z: 273 ([M+H]$^{+}$).

4-hydroxyquinoline-6-carbonitrile (4): To a 250 mL round bottom flask was added with 4-[(2,2-dimethyl-4,6-dioxo-1,3-dioxan-5-ylidene)methylamino]benzonitrile (13.6 mmol, 3.7 g) and phenoxybenzene (40 mL). The resulting solution was at 220° C. for 40 min. Upon completion, the resulting solution was cooled to room temperature and hexane (100 mL) was added. The precipitate was collected by filtration and washed with hexane, the crude compound was purified via flash column chromatography using a gradient of 0-5% MeOH/DCM to give 4-hydroxyquinoline-6-carbonitrile as a brown solid (1.5 g, 65% yield). ESI-MS m/z: 273 ([M+H]$^{+}$).

4-chloroquinoline-6-carbonitrile (5): To a 100 mL round-bottom flask was placed a solution of 4-hydroxyquinoline-6-carbonitrile (5.88 mmol, 1 g) in dioxane (30 mL), and POCl$_3$ (29.4 mmol, 2.69 mL) was added. Reaction was stirred for 1.5 h at 90° C. Upon completion, solvent was removed under reduced pressure. The pH value of the solution was adjusted to 8 with saturated sodium carbonate solution. The resulting solution was extracted with three times (20 ml each) of ethyl acetate, organic layers were combined and dried over anhydrous sodium sulfate and concentrated in vacuum. The crude was purified using flash column chromatography using a gradient of 0-2% MeOH/DCM to give 4-chloroquinoline-6-carbonitrile as a white solid (0.48g, 44% yield). ESI-MS m/z: 189 ([M+H]$^+$). $^1$H-NMR (300 MHz, CD$_3$OD): δ 8.94 (d, J=4.8 Hz, 1H), 8.76 (d, J=1.5 Hz, 1H), 8.24 (d, J=8.8 Hz, 2H), 8.07 (dd, J=1.8, 8.9 Hz, 1H), 7.82 (d, J=5.0 Hz, 1H).

methyl 6-methylnaphthalene-2-carboxylate (7): To a 250 mL round-bottom flask was added a solution of methyl 6-bromonaphthalene-2-carboxylate (6.79 mmol, 1.8 g) and methylboronic acid (10.2 mmol, 610 mg) in acetonitrile (30 mL) and water (10 mL). Then Tetrakis(triphenylphosphine)palladium(0) (0.68 mmol, 785 mg) and potassium carbonate (20.4 mmol, 2.82 g) was added. Reaction was protected with nitrogen and stirred for overnight at 80° C. Upon completion, the mixture was cooled to room temperature and water was added, the mixture was extracted with ethyl acetate for three times, and the organic layers were collected and washed with brine and dried by Na$_2$SO$_4$. Condensed and purified by flash column chromatography using a gradient of 0-2% MeOH/DCM to give methyl 6-methylnaphthalene-2-carboxylate as a white solid (1.15 g, 85% yield). ESI-MS m/z: 201 ([M+H]$^+$).

methyl 6-(bromomethyl)naphthalene-2-carboxylate (8): To a 250 mL round-bottom flask was added a solution of methyl 6-methylnaphthalene-2-carboxylate (5.59 mmol, 1.12 g) in CCl$_4$ (20 mL). Then NBS (5.87 mmol, 1.05 g) and AIBN (0.28 mmol, 46 mg) were added and the mixture was protected with nitrogen and reflux for 4h. Upon completion, the mixture was cooled to room temperature and hexane (25 mL) was added, the mixture was stirred at room temperature for 2h. Filter the mixture and wash the residue with hexane. The filtrate were collected and condensed and purified by flash column chromatography using a gradient of 0-30% ethyl acetate/hexane to give methyl 6-(bromomethyl)naphthalene-2-carboxylate as a white solid (1.3 g, 83% yield). ESI-MS m/z: 280 ([M+H]$^+$). $^1$H-NMR (300 MHz, CDCl$_3$): 8.58 (d, J=1.8 Hz, 1H), 8.30 (dd, J=8.9, 1.8 Hz, 1H), 8.27 (d, J=8.6 Hz, 1H), 8.10 (d, J=8.9 Hz, 1H), 7.64 (d, J=8.6 Hz, 1H), 4.71 (s, 2H), 4.00 (s, 3H).

methyl 6-(cyanomethyl)naphthalene-2-carboxylate (9): To a 250 mL round-bottom flask was added a solution of methyl 6-(bromomethyl)naphthalene-2-carboxylate (1.79 mmol, 500 mg) in methanol (15 mL). Then KCN (5.37 mmol, 350 mg) was added and the mixture was protected with nitrogen and reflux for 8h. Upon completion, the mixture was cooled to room temperature and condensed, the residue was dissolved in DCM and water, then extracted with DCM three times, the organic layers were combined and washed with sat NaCl aq, dried by Na$_2$SO$_4$. After that, condensed and purified by flash column chromatography using a gradient of 0-5% MeOH/DCM to give methyl 6-(cyanomethyl)naphthalene-2-carboxylate as a white solid (160 mg, 40% yield). ESI-MS m/z: 226 ([M+H]$^+$). $^1$H-NMR (300 MHz, CDCl$_3$): 8.61 (s, 1H), 8.11 (dd, J=8.6, 1.9 Hz, 1H), 8.30 (dd, J=8.9, 1.8 Hz, 1H), 7.98 (d, J=8.6 Hz, 1H), 7.89 (d, J=5.5 Hz, 1H), 7.87 (s, 1H), 7.46 (dd, J=8.6, 1.9 Hz, 1H), 3.99 (s, 3H), 3.95 (s, 2H).

6-(cyanomethyl)naphthalene-2-carboxylic acid (10): To a 10 mL round-bottom flask was added a solution of methyl 6-(cyanomethyl)naphthalene-2-carboxylate (1.99 mmol, 448 mg) in THF (3 mL) and water (3 mL). Then LiOH—H$_2$O (2.2 mmol, 92 mg) was added and the mixture was stirred at room temperature for 4h. Upon completion, the mixture was condensed and dissolved in 2 mL water and acidified by 2N HCl to pH 2-3. The precipitation was collected and washed with water until pH=7 and dried to give 6-(cyanomethyl)naphthalene-2-carboxylic acid (396 mg, 94%) that used for the next step without further purification. ESI-MS m/z: 212 ([M+H]$^+$).

General method for 11a-d: To a round-bottom flask was added a solution of 6-(cyanomethyl)naphthalene-2-carboxylic acid (1 eq) in DMF (5 mL), then HATU (1.5 eq), DIPEA (3 eq) were added and stirred for 15 min. After that, piperazine derivatives (1 eq) was added and the mixture was stirred for 2h. Upon completion, the mixture was diluted with water, extracted with DCM, the organic layers were combined, dried by Na$_2$SO$_4$, condensed and purified by flash column chromatography using a gradient of 0-5% MeOH/DCM to give the target compound.

tert-butyl-(3-(6-(cyanomethyl)-N-methyl-2-naphthamido)propyl)carbamate (11a): A white solid (166 mg, yield 67%). ESI-MS m/z: 382 ([M+H]$^+$).

tert-butyl 4-[6-(cyanomethyl)naphthalene-2-carbonyl]piperazine-1-carboxylate (11b): A white solid (343 mg, 61%). ESI-MS m/z: 380 ([M+H]$^+$).

tert-butyl-(3-(4-(6-(cyanomethyl)-2-naphthoyl)piperazin-1-yl)propyl)carbamate (tic): A white solid (300 mg, 66%). ESI-MS m/z: 437 ([M+H]$^+$).

2-[6-(thiomorpholine-4-carbonyl)-2-naphthyl]acetonitrile (11d): 932 mg, 76%. ESI-MS m/z: 297 ([M+H]$^+$). $^1$H-NMR (300 MHz, CDCl$_3$): 7.88 (m, 4H), 7.50 (dd, J=8.5, 1.5 Hz, 1H), 7.45 (dd, J=8.5, 1.5 Hz, 1H), 4.05 (s, 2H), 3.94 (s, 2H), 3.74 (s, 2H), 2.72 (s, 2H), 2.63 (s, 2H).

General method for 12a-d: To a round-bottom flask was added a solution of 11a-d (1 eq) in MeOH (3 mL), water (3 mL), and NH$_4$OH (1 mL). Then raney Ni (0.2 eq) was added and the mixture was saturated with H$_2$ and stirred at room temperature for overnight. Upon completion, the mixture was diluted with hexane and filtered, the filtration was condensed to give target compounds.

tert-butyl-(3-(6-(2-aminoethyl)-N-methyl-2-naphthamido)propyl)carbamate (12a): A white solid (219 mg, yield 77%) and used for the next step without further purification. ESI-MS m/z: 386 ([M+H]$^+$).

tert-butyl 4-[6-(2-aminoethyl)naphthalene-2-carbonyl]piperazine-1-carboxylate (12b): A grey solid (290 mg, yield 96%). ESI-MS m/z: 384 ([M+H]$^+$).

tert-butyl-(3-(4-(6-(2-aminoethyl)-2-naphthoyl)piperazin-1-yl)propyl)carbamate (12c): A brown solid (215 mg, yield 88%) and used for the next step without further purification. ESI-MS m/z: 441 ([M+H]$^+$).

[6-(2-aminoethyl)-2-naphthyl]-thiomorpholino-methanone (12d): A yellow solid (399 mg, 42%). ESI-MS m/z: 301 ([M+H]$^+$). $^1$H-NMR (300 MHz, DMSO-d6): 7.97 (d, J=7.8 Hz, 2H), 7.96 (s, 1H), 7.93 (d, J=8.7 Hz, 1H), 7.84 (s, 1H), 7.49 (d, J=8.2, 2H), 3.89 (m, 2H), 3.51 (m, 2H), 3.11 (m, 4H), 2.66 (m, 4H).

General method for 13a-d: To a round-bottom flask was added a solution of 4-chloroquinoline-6-carbonitrile (1 eq) and 12a-d (1 eq) in DMSO. Then DIPEA (2 eq) was added. The mixture was stirred at 110° C. for overnight. Upon completion, the mixture was cooled to room temperature, water was added, extracted with DCM, the organic layers were combined and dried by Na$_2$SO$_4$, condensed, and purified by flash column chromatography via a gradient of 0-7% MeOH/DCM to give the target compounds.

tert-butyl-N-[3-[[6-[2-[(6-cyano-4-quinolyl)amino]ethyl]naphthalene-2-carbonyl]-methyl-amino]propyl]carbamate (13a): A white solid (360 mg, 59% yield). ESI-MS m/z: 538 ([M+H]$^+$). $^1$H-NMR (300 MHz, CD$_2$Cl$_2$): 8.55 (d, J=5.1 Hz, 1H), 8.22 (s, 1H), 7.94 (d, J=8.6 Hz, 1H), 7.83 (d, J=8.6 Hz, 2H), 7.79 (s, 1H), 7.72 (dd, J=8.6, 2.0 Hz, 1H), 7.67 (s, 1H), 7.47 (d, J=8.5 Hz, 1H), 7.41 (d, J=8.5 Hz, 1H), 6.59 (d, J=5.1

Hz, 1H), 5.83 (m, 1H), 5.47 (m, 1H), 3.66 (m, 4H), 3.20 (m, 4H), 2.94 (s, 3H), 1.82 (m, 2H), 1.43 (s, 9H).

tert-butyl 4-[6-[2-[(6-cyano-4-quinolyl)amino]ethyl]naphthalene-2-carbonyl]piperazine-1-carboxylate (13b): A light yellow solid (179 mg, yield 43%). ESI-MS m/z: 536 ([M+H]$^+$). $^1$H-NMR (300 MHz, DMSO-d6): 8.90 (s, 1H), 8.53 (d, J=5.9 Hz, 1H), 8.05 (m, 1H), 7.97-7.88 (m, 6H), 7.58 (dd, J=8.4, 1.3 Hz, 1H), 7.49 (dd, J=8.4, 1.3 Hz, 1H), 6.79 (d, J=5.9 Hz, 1H), 3.71 (m, 2H), 3.58 (m, 4H), 3.47 (m, 2H), 3.40 (m, 2H), 3.19 (m, 2H), 1.41 (s, 9H).

tert-butyl-(3-(4-(6-(2-((6-cyanoquinolin-4-yl)amino) ethyl)-2-naphthoyl)piperazin-1-yl)propyl)carbamate (13c): A white solid (110 mg, yield 46%). ESI-MS m/z: 593 ([M+H]$^+$). $^1$H-NMR (300 MHz, DMSO-d6): 8.87 (s, 1H), 8.52 (d, J=5.4 Hz, 1H), 7.92 (m, 6H), 7.80 (m, 1H), 7.57 (dd, J=8.4, 1.3 Hz, 1H), 7.47 (dd, J=8.4, 1.3 Hz, 1H), 6.81 (m, 1H), 6.73 (d, J=5.4 Hz, 1H), 3.66 (m, 4H), 3.17 (t, J=7.5 Hz, 2H), 2.93 (q, J=6.6 Hz, 2H), 2.41 (m, 4H), 2.33 (t, J=6.6 Hz, 2H), 1.54 (m, 2H), 1.24 (m, 2H).

4-[2-[6-(thiomorpholine-4-carbonyl)-2-naphthyl]ethylamino]quinoline-6-carbonitrile (13d): A white solid (297 mg, 41%). ESI-MS m/z: 453 ([M+H]$^+$). $^1$H-NMR (300 MHz, DMSO-d6): 8.86 (s, 1H), 8.52 (d, J=5.8 Hz, 1H), 7.96 (d, J=7.8 Hz, 1H), 7.94 (s, 1H), 7.90 (d, J=7.8 Hz, 1H), 7.88 (s, 2H), 7.69 (t, J=5.0 Hz, 1H), 7.57 (dd, J=8.6, 1.4 Hz, 1H), 7.47 (dd, J=8.2, 1.2 Hz, 1H), 3.88 (m, 2H), 3.67 (m, 2H), 3.65 (q, J=6.8 Hz, 2H), 3.17 (t, J=6.8 Hz, 2H), 2.66 (m, 4H).

N-(3-aminopropyl)-6-[2-[(6-cyano-4-quinolyl)amino] ethyl]-N-methyl-naphthalene-2-carboxamide (13e): To a 100 mL round-bottom flask was added a solution of tert-butyl N-[3-[[6-[2-[(6-cyano-4-quinolyl)amino]ethyl]naphthalene-2-carbonyl]-methyl-amino]propyl]carbamate (6.7 mmol, 763 mg) in DCM (5 mL). Then TFA (1 mL) was added and the mixture was stirred at room temperature for 4h. Upon completion, the mixture was condensed and purified by flash column in a gradient of 0-10% MeOH/DCM to give N-(3-aminopropyl)-6-[2-[(6-cyano-4-quinolyl)amino] ethyl]-N-methyl-naphthalene-2-carboxamide as a yellow solid (280 mg, 96%). ESI-MS m/z: 436 ([M+H]$^+$).

4-[2-[6-[4-(3-aminopropyl)piperazine-1-carbonyl]-2-naphthyl]ethylamino]quinoline-6-carbonitrile (13f): The same procedure as 13e; A light yellow solid (185 mg, 95% yield) and used for the next step without further purification. ESI-MS m/z: 607 ([M+H]$^+$). $^1$H-NMR (300 MHz, DMSO-d6): 9.66 (s, 1H), 9.11 (s, 1H), 8.63 (d, J=7.4 Hz, 1H), 8.28 (d, J=8.7 Hz, 1H), 8.04 (s, 1H), 8.03 (d, J=7.4 Hz, 1H), 7.94 (m, 4H), 7.62 (d, J=8.7 Hz, 2H), 7.56 (d, J=8.7 Hz, 1H), 7.11 (d, J=7.4 Hz, 1H), 3.94 (q, J=6.7 Hz, 2H), 3.45 (m, 2H), 3.21 (m, 8H), 2.88 (m, 2H), 1.96 (m, 2H), 1.24 (m, 2H).

4-[2-[6-(1-oxo-1,4-thiazinane-4-carbonyl)-2-naphthyl] ethylamino]quinoline-6-carbonitrile (13g): To a 50 mL round-bottom flask was added a solution of 4-[2-[6-(thiomorpholine-4-carbonyl)-2-naphthyl]ethylamino]quinoline-6-carbonitrile (0.57 mmol, 258 mg) in MeOH (8 mL) and cooled to −40° C. Then NaIO$_4$ (0.63 mmol, 134 mg) in water (2 mL) was added to the above solution slowly. The mixture was stirred at −40° C. for 30 min, then stirred at 0° C. for another 2h, and stirred at room temperature for overnight. Upon completion, water was added, extracted with DCM, the organic layers were combined and dried by Na$_2$SO$_4$, condensed, and purified by flash column chromatography via a gradient of 0-7% MeOH/DCM to give 4-[2-[6-(1-oxo-1,4-thiazinane-4-carbonyl)-2-naphthyl]ethylamino]quinoline-6-carbonitrile (194 mg, 73%). ESI-MS m/z: 469 ([M+H]$^+$). $^1$H-NMR (300 MHz, CDCl$_3$): 8.62 (d, J=5.3 Hz, 1H), 8.18 (s, 1H), 7.98 (d, J=8.8 Hz, 1H), 7.82 (t, J=7.9 Hz, 2H), 7.71 (d, J=8.8 Hz, 1H), 7.65 (s, 1H), 7.49 (d, J=8.8 Hz, 1H), 7.41 (d, J=8.8 Hz, 1H), 6.55 (d, J=5.3 Hz, 1H), 5.77 (m, 1H), 4.08 (m, 4H), 3.67 (q, J=6.1 Hz, 2H), 3.20 (t, J=6.9 Hz, 2H), 2.79 (m, 4H).

4-[2-[6-(1-imino-1-oxo-1,4-thiazinane-4-carbonyl)-2-naphthyl]ethylamino]quinoline-6-carbonitrile (13h): To a 25 mL round-bottom flask was added a solution of 4-[2-[6-(1-oxo-1,4-thiazinane-4-carbonyl)-2-naphthyl]ethylamino]quinoline-6-carbonitrile (0.36 mmol, 166 mg) in DCM (10 mL). Then iodobenzene diacetate (0.53 mmol, 171 mg), 2,2,2-trifluoroacetamide (0.71 mmol, 80 mg), rhodium(II) acetate dimer (0.0018 mmol, 8 mg), and MgO (1.42 mmol, 57 mg) were added, the mixture was stirred at room temperature for overnight. Upon completion, the mixture was filtered through celite, and washed the celite with DCM, the filtration was condensed and purified by flash column chromatography using a gradient of 0-7% MeOH/DCM to give the intermediate compound N-[4-[6-[2-[(6-cyano-4-quinolyl)amino]ethyl]naphthalene-2-carbonyl]-1-oxo-1,4-thiazinan-1-ylidene]-2,2,2-trifluoro-acetamide (100 mg). To a 100 mL round-bottom flask was added a solution of N-[4-[6-[2-[(6-cyano-4-quinolyl)amino]ethyl]naphthalene-2-carbonyl]-1-oxo-1,4-thiazinan-1-ylidene]-2,2,2-trifluoro-acetamide (0.17 mmol, 100 mg) and K$_2$CO$_3$ (0.86 mmol, 119 mg) in MeOH (7 mL). Then the mixture was stirred at room temperature for overnight. Upon completion, the mixture was filtered, and washed the residue with MeOH, the filtration was condensed and purified by flash column using a gradient of 0-7% MeOH/DCM to give 4-[2-[6-(1-imino-1-oxo-1,4-thiazinane-4-carbonyl)-2-naphthyl]ethylamino] quinoline-6-carbonitrile (50 mg, 60%). ESI-MS m/z: 484 ([M+H]$^+$). $^1$H-NMR (300 MHz, DMSO-d6): 8.86 (s, 1H), 8.52 (d, J=5.6 Hz, 1H), 8.05 (s, 1H), 7.96 (d, J=8.8 Hz, 1H), 7.91 (d, J=8.8 Hz, 1H), 7.88 (m, 3H), 7.70 (m, 1H), 7.57 (t, J=7.2 Hz, 2H), 6.71 (d, J=5.6 Hz, 1H), 3.90 (m, 2H), 3.73 (m, 2H), 3.65 (q, J=6.9 Hz, 2H), 3.17 (t, J=7.6 Hz, 2H), 3.14 (m, 4H).

4-[2-[6-(4-acetylpiperazine-1-carbonyl)-2-naphthyl]ethylamino]quinoline-6-carbonitrile (13i): To a 100 mL round-bottom flask was added a solution of tert-butyl 4-[6-[2-[(6-cyano-4-quinolyl)amino]ethyl]naphthalene-2-carbonyl] piperazine-1-carboxylate (1.42 mmol, 760 mg) in DCM (5 mL). Then TFA (1 mL) was added and the mixture was stirred at room temperature for 4h. Upon completion, the mixture was condensed to give 4-[2-[6-(piperazine-1-carbonyl)-2-naphthyl]ethylamino]quinoline-6-carbonitrile (610 mg, 99% yield) and used for the next step without further purification. To a 100 mL round-bottom flask was added a solution of 4-[2-[6-(piperazine-1-carbonyl)-2-naphthyl]ethylamino]quinoline-6-carbonitrile (0.15 mmol, 65 mg) and DIEA (0.3 mmol, 39 mg) in DCM (3 mL) and cooled to 0° C., then acetyl chloride (0.22 mmol, 18 mg) was added and the reaction was stirred at room temperature for 2h. Then water was added, extracted with DCM, the organic layers were combined, dried by Na$_2$SO$_4$, condensed, and purified by flash column chromatography using a gradient of 0-5% MeOH/DCM to give 4-[2-[6-(4-acetylpiperazine-1-carbonyl)-2-naphthyl]ethylamino]quinoline-6-carbonitrile (65 mg, 91% yield). ESI-MS m/z: 478 ([M+H]$^+$). $^1$H-NMR (300 MHz, CD$_3$OD): 8.68 (s, 1H), 8.40 (d, J=5.9 Hz, 1H), 7.94 (s, 1H), 7.96-7.85 (m, 4H), 7.80 (s, 1H), 7.54 (dd, J=8.4, 1.6 Hz, 1H), 7.49 (dd, J=8.4, 1.6 Hz, 1H), 6.80 (d, J=5.9 Hz, 1H), 3.86 (t, J=7.0 Hz, 2H), 3.72 (m, 4H), 3.26 (t, J=7.0 Hz, 2H), 3.22 (m, 4H), 2.13 (s, 3H).

Senexin C is a Highly Selective Inhibitor of CDK8/19.

FIG. 1 and Table 1 show the results of kinome profiling of Senexin C (6148 (GJ-2331/2335), carried out by DiscoverX (now Eurofins) on the scanMAX panel using the KINO- MEscan™ assay that uses an active site-directed competition binding assay to quantitatively measure interactions between test compounds and 468 human kinases and disease relevant mutant variants. Senexin C was tested at 2,000 nM concentration. All the kinases inhibited >65% by this concentration of the compound are represented in FIG. 1 as circles in the evolutionary dendrogram. The overall kinome selectivity of 2,000 nM Senexin C in the form of S-scores, where S(#)=(number of non-mutant kinases with % Ctrl (or POC)<#)/(number of non-mutant kinases tested) was as follows: S(35)=0.012, S(10)=0.002. The strongest inhibition was found for CDK8 (1.3 POC) and CDK19 (designated by DiscoverX as CDK11) (13 POC). In contrast, none of the other members of the CDK family in the scanMAX panel, including CDK2, CDK3, CDK4, CDK5, CDK7, CDK9, CDK11A (designated by DiscoverX as CDCl$_2$L2), CDK11B (designated by DiscoverX as CDCl$_2$L2), CDK13 (designated by DiscoverX as CDCl$_2$L5), CDK14 (designated by DiscoverX as PFTK1), CDK15 (designated by DiscoverX as PFTAIRE2), CDK16 (designated by DiscoverX as PCTK1), CDK17 (designated by DiscoverX as PCTK2), CDK18 (designated by DiscoverX as PCTK3), CDKL1, CDKL3, and CDKL5 were inhibited to less than 64 POC.

TABLE 1

ScanMAX panel of Senexin C at 2000 nM.

| DiscoveRx Gene Symbol | Entrez Gene Symbol | Percent Control |
|---|---|---|
| AAK1 | AAK1 | 84 |
| ABL1(E255K)-phosphorylated | ABL1 | 93 |
| ABL1(F317I)-nonphosphorylated | ABL1 | 88 |
| ABL1(F317I)-phosphorylated | ABL1 | 89 |
| ABL1(F317L)-nonphosphorylated | ABL1 | 93 |
| ABL1(F317L)-phosphorylated | ABL1 | 74 |
| ABL1(H396P)-nonphosphorylated | ABL1 | 73 |
| ABL1(H396P)-phosphorylated | ABL1 | 81 |
| ABL1(M351T)-phosphorylated | ABL1 | 80 |
| ABL1(Q252H)-nonphosphorylated | ABL1 | 73 |
| ABL1(Q252H)-phosphorylated | ABL1 | 89 |
| ABL1(T315I)-nonphosphorylated | ABL1 | 90 |
| ABL1(T315I)-phosphorylated | ABL1 | 76 |
| ABL1(Y253F)-phosphorylated | ABL1 | 74 |
| ABL1-nonphosphorylated | ABL1 | 71 |
| ABL1-phosphorylated | ABL1 | 67 |
| ABL2 | ABL2 | 93 |
| ACVR1 | ACVR1 | 92 |
| ACVR1B | ACVR1B | 92 |
| ACVR2A | ACVR2A | 89 |
| ACVR2B | ACVR2B | 90 |
| ACVRL1 | ACVRL1 | 93 |
| ADCK3 | CABC1 | 100 |
| ADCK4 | ADCK4 | 97 |
| AKT1 | AKT1 | 89 |
| AKT2 | AKT2 | 100 |
| AKT3 | AKT3 | 100 |
| ALK | ALK | 89 |
| ALK(C1156Y) | ALK | 83 |
| ALK(L1196M) | ALK | 92 |
| AMPK-alpha1 | PRKAA1 | 94 |

TABLE 1-continued

ScanMAX panel of Senexin C at 2000 nM.

| DiscoveRx Gene Symbol | Entrez Gene Symbol | Percent Control |
|---|---|---|
| AMPK-alpha2 | PRKAA2 | 42 |
| ANKK1 | ANKK1 | 69 |
| ARK5 | NUAK1 | 89 |
| ASK1 | MAP3K5 | 91 |
| ASK2 | MAP3K6 | 79 |
| AURKA | AURKA | 88 |
| AURKB | AURKB | 75 |
| AURKC | AURKC | 100 |
| AXL | AXL | 95 |
| BIKE | BMP2K | 97 |
| BLK | BLK | 100 |
| BMPR1A | BMPR1A | 95 |
| BMPR1B | BMPR1B | 70 |
| BMPR2 | BMPR2 | 66 |
| BMX | BMX | 100 |
| BRAF | BRAF | 84 |
| BRAF(V600E) | BRAF | 89 |
| BRK | PTK6 | 97 |
| BRSK1 | BRSK1 | 100 |
| BRSK2 | BRSK2 | 96 |
| BTK | BTK | 78 |
| BUB1 | BUB1 | 68 |
| CAMK1 | CAMK1 | 84 |
| CAMK1B | PNCK | 92 |
| CAMK1D | CAMK1D | 80 |
| CAMK1G | CAMK1G | 92 |
| CAMK2A | CAMK2A | 100 |
| CAMK2B | CAMK2B | 97 |
| CAMK2D | CAMK2D | 94 |
| CAMK2G | CAMK2G | 100 |
| CAMK4 | CAMK4 | 95 |
| CAMKK1 | CAMKK1 | 100 |
| CAMKK2 | CAMKK2 | 82 |
| CASK | CASK | 84 |
| CDC2L1 | CDK11B | 96 |
| CDC2L2 | CDC2L2 | 97 |
| CDC2L5 | CDK13 | 64 |
| CDK11 | CDK19 | 13 |
| CDK2 | CDK2 | 95 |
| CDK3 | CDK3 | 86 |
| CDK4 | CDK4 | 67 |
| CDK4-cyclinD1 | CDK4 | 83 |
| CDK4-cyclinD3 | CDK4 | 80 |
| CDK5 | CDK5 | 100 |
| CDK7 | CDK7 | 69 |
| CDK8 | CDK8 | 1.3 |
| CDK9 | CDK9 | 97 |
| CDKL1 | CDKL1 | 94 |
| CDKL2 | CDKL2 | 75 |
| CDKL3 | CDKL3 | 87 |
| CDKL5 | CDKL5 | 70 |
| CHEK1 | CHEK1 | 100 |
| CHEK2 | CHEK2 | 98 |
| CIT | CIT | 48 |
| CLK1 | CLK1 | 60 |
| CLK2 | CLK2 | 93 |
| CLK3 | CLK3 | 65 |
| CLK4 | CLK4 | 69 |
| CSF1R | CSF1R | 85 |
| CSF1R-autoinhibited | CSF1R | 91 |
| CSK | CSK | 85 |
| CSNK1A1 | CSNK1A1 | 76 |
| CSNK1A1L | CSNK1A1L | 88 |
| CSNK1D | CSNK1D | 87 |
| CSNK1E | CSNK1E | 81 |
| CSNK1G1 | CSNK1G1 | 100 |
| CSNK1G2 | CSNK1G2 | 89 |
| CSNK1G3 | CSNK1G3 | 76 |
| CSNK2A1 | CSNK2A1 | 56 |
| CSNK2A2 | CSNK2A2 | 64 |
| CTK | MATK | 56 |
| DAPK1 | DAPK1 | 100 |
| DAPK2 | DAPK2 | 100 |
| DAPK3 | DAPK3 | 95 |
| DCAMKL1 | DCLK1 | 63 |

TABLE 1-continued

ScanMAX panel of Senexin C at 2000 nM.

| DiscoveRx Gene Symbol | Entrez Gene Symbol | Percent Control |
|---|---|---|
| DCAMKL2 | DCLK2 | 94 |
| DCAMKL3 | DCLK3 | 96 |
| DDR1 | DDR1 | 100 |
| DDR2 | DDR2 | 64 |
| DLK | MAP3K12 | 68 |
| DMPK | DMPK | 98 |
| DMPK2 | CDC42BPG | 83 |
| DRAK1 | STK17A | 100 |
| DRAK2 | STK17B | 87 |
| DYRK1A | DYRK1A | 63 |
| DYRK1B | DYRK1B | 83 |
| DYRK2 | DYRK2 | 68 |
| EGFR | EGFR | 91 |
| EGFR(E746-A750del) | EGFR | 100 |
| EGFR(G719C) | EGFR | 93 |
| EGFR(G719S) | EGFR | 100 |
| EGFR(L747-E749del, A750P) | EGFR | 77 |
| EGFR(L747-S752del, P753S) | EGFR | 98 |
| EGFR(L747-T751del, Sins) | EGFR | 74 |
| EGFR(L858R) | EGFR | 93 |
| EGFR(L858R, T790M) | EGFR | 82 |
| EGFR(L861Q) | EGFR | 64 |
| EGFR(S752-1759del) | EGFR | 99 |
| EGFR(T790M) | EGFR | 93 |
| EIF2AK1 | EIF2AK1 | 84 |
| EPHA1 | EPHA1 | 93 |
| EPHA2 | EPHA2 | 100 |
| EPHA3 | EPHA3 | 100 |
| EPHA4 | EPHA4 | 93 |
| EPHA5 | EPHA5 | 97 |
| EPHA6 | EPHA6 | 79 |
| EPHA7 | EPHA7 | 91 |
| EPHA8 | EPHA8 | 91 |
| EPHB1 | EPHB1 | 92 |
| EPHB2 | EPHB2 | 86 |
| EPHB3 | EPHB3 | 81 |
| EPHB4 | EPHB4 | 89 |
| EPHB6 | EPHB6 | 86 |
| ERBB2 | ERBB2 | 73 |
| ERBB3 | ERBB3 | 76 |
| ERBB4 | ERBB4 | 95 |
| ERK1 | MAPK3 | 95 |
| ERK2 | MAPK1 | 93 |
| ERK3 | MAPK6 | 89 |
| ERK4 | MAPK4 | 87 |
| ERK5 | MAPK7 | 94 |
| ERK8 | MAPK15 | 76 |
| ERN1 | ERN1 | 58 |
| FAK | PTK2 | 89 |
| FER | FER | 91 |
| FES | FES | 81 |
| FGFR1 | FGFR1 | 85 |
| FGFR2 | FGFR2 | 98 |
| FGFR3 | FGFR3 | 100 |
| FGFR3(G697C) | FGFR3 | 93 |
| FGFR4 | FGFR4 | 96 |
| FGR | FGR | 90 |
| FLT1 | FLT1 | 99 |
| FLT3 | FLT3 | 89 |
| FLT3(D835H) | FLT3 | 88 |
| FLT3(D835V) | FLT3 | 67 |
| FLT3(D835Y) | FLT3 | 73 |
| FLT3(ITD) | FLT3 | 97 |
| FLT3(ITD, D835V) | FLT3 | 55 |
| FLT3(ITD, F691L) | FLT3 | 59 |
| FLT3(K663Q) | FLT3 | 87 |
| FLT3(N841I) | FLT3 | 100 |
| FLT3(R834Q) | FLT3 | 70 |
| FLT3-autoinhibited | FLT3 | 88 |
| FLT4 | FLT4 | 97 |
| FRK | FRK | 92 |
| FYN | FYN | 89 |
| GAK | GAK | 100 |
| GCN2(Kin.Dom.2, S808G) | EIF2AK4 | 93 |
| GRK1 | GRK1 | 63 |
| GRK2 | ADRBK1 | 63 |
| GRK3 | ADRBK2 | 73 |
| GRK4 | GRK4 | 100 |
| GRK7 | GRK7 | 87 |
| GSK3A | GSK3A | 94 |
| GSK3B | GSK3B | 67 |
| HASPIN | GSG2 | 29 |
| HCK | HCK | 96 |
| HIPK1 | HIPK1 | 73 |
| HIPK2 | HIPK2 | 67 |
| HIPK3 | HIPK3 | 52 |
| HIPK4 | HIPK4 | 75 |
| HPK1 | MAP4K1 | 94 |
| HUNK | HUNK | 74 |
| ICK | ICK | 54 |
| IGF1R | IGF1R | 94 |
| IKK-alpha | CHUK | 76 |
| IKK-beta | IKBKB | 76 |
| IKK-epsilon | IKBKE | 91 |
| INSR | INSR | 93 |
| INSRR | INSRR | 88 |
| IRAK1 | IRAK1 | 45 |
| IRAK3 | IRAK3 | 94 |
| IRAK4 | IRAK4 | 67 |
| ITK | ITK | 93 |
| JAK1(JH1domain-catalytic) | JAK1 | 94 |
| JAK1(JH2domain-pseudokinase) | JAK1 | 58 |
| JAK2(JH1domain-catalytic) | JAK2 | 56 |
| JAK3(JH1domain-catalytic) | JAK3 | 65 |
| JNK1 | MAPK8 | 54 |
| JNK2 | MAPK9 | 67 |
| JNK3 | MAPK10 | 61 |
| KIT | KIT | 95 |
| KIT(A829P) | KIT | 82 |
| KIT(D816H) | KIT | 57 |
| KIT(D816V) | KIT | 100 |
| KIT(L576P) | KIT | 100 |
| KIT(V559D) | KIT | 95 |
| KIT(V559D, T670I) | KIT | 90 |
| KIT(V559D, V654A) | KIT | 89 |
| KIT-autoinhibited | KIT | 88 |
| LATS1 | LATS1 | 76 |
| LATS2 | LATS2 | 88 |
| LCK | LCK | 92 |
| LIMK1 | LIMK1 | 95 |
| LIMK2 | LIMK2 | 93 |
| LKB1 | STK11 | 87 |
| LOK | STK10 | 94 |
| LRRK2 | LRRK2 | 85 |
| LRRK2(G2019S) | LRRK2 | 56 |
| LTK | LTK | 93 |
| LYN | LYN | 88 |
| LZK | MAP3K13 | 46 |
| MAK | MAK | 100 |
| MAP3K1 | MAP3K1 | 78 |
| MAP3K15 | MAP3K15 | 83 |
| MAP3K2 | MAP3K2 | 68 |
| MAP3K3 | MAP3K3 | 83 |
| MAP3K4 | MAP3K4 | 81 |
| MAP4K2 | MAP4K2 | 29 |
| MAP4K3 | MAP4K3 | 100 |
| MAP4K4 | MAP4K4 | 93 |
| MAP4K5 | MAP4K5 | 95 |
| MAPKAPK2 | MAPKAPK2 | 91 |
| MAPKAPK5 | MAPKAPK5 | 62 |
| MARK1 | MARK1 | 81 |
| MARK2 | MARK2 | 100 |
| MARK3 | MARK3 | 94 |

TABLE 1-continued

ScanMAX panel of Senexin C at 2000 nM.

| DiscoveRx Gene Symbol | Entrez Gene Symbol | Percent Control |
|---|---|---|
| MARK4 | MARK4 | 78 |
| MAST1 | MAST1 | 96 |
| MEK1 | MAP2K1 | 59 |
| MEK2 | MAP2K2 | 64 |
| MEK3 | MAP2K3 | 87 |
| MEK4 | MAP2K4 | 58 |
| MEK5 | MAP2K5 | 63 |
| MEK6 | MAP2K6 | 80 |
| MELK | MELK | 97 |
| MERTK | MERTK | 89 |
| MET | MET | 90 |
| MET(M1250T) | MET | 88 |
| MET(Y1235D) | MET | 78 |
| MINK | MINK1 | 56 |
| MKK7 | MAP2K7 | 75 |
| MKNK1 | MKNK1 | 72 |
| MKNK2 | MKNK2 | 71 |
| MLCK | MYLK3 | 100 |
| MLK1 | MAP3K9 | 87 |
| MLK2 | MAP3K10 | 79 |
| MLK3 | MAP3K11 | 99 |
| MRCKA | CDC42BPA | 98 |
| MRCKB | CDC42BPB | 100 |
| MST1 | STK4 | 95 |
| MST1R | MST1R | 100 |
| MST2 | STK3 | 100 |
| MST3 | STK24 | 100 |
| MST4 | MST4 | 68 |
| MTOR | MTOR | 79 |
| MUSK | MUSK | 90 |
| MYLK | MYLK | 83 |
| MYLK2 | MYLK2 | 91 |
| MYLK4 | MYLK4 | 98 |
| MYO3A | MYO3A | 100 |
| MYO3B | MYO3B | 31 |
| NDR1 | STK38 | 79 |
| NDR2 | STK38L | 96 |
| NEK1 | NEK1 | 84 |
| NEK10 | NEK10 | 41 |
| NEK11 | NEK11 | 60 |
| NEK2 | NEK2 | 100 |
| NEK3 | NEK3 | 60 |
| NEK4 | NEK4 | 60 |
| NEK5 | NEK5 | 97 |
| NEK6 | NEK6 | 93 |
| NEK7 | NEK7 | 94 |
| NEK9 | NEK9 | 97 |
| NIK | MAP3K14 | 88 |
| NIM1 | MGC42105 | 67 |
| NLK | NLK | 90 |
| OSR1 | OXSR1 | 51 |
| p38-alpha | MAPK14 | 84 |
| p38-beta | MAPK11 | 80 |
| p38-delta | MAPK13 | 97 |
| p38-gamma | MAPK12 | 100 |
| PAK1 | PAK1 | 92 |
| PAK2 | PAK2 | 84 |
| PAK3 | PAK3 | 98 |
| PAK4 | PAK4 | 97 |
| PAK6 | PAK6 | 90 |
| PAK7 | PAK7 | 100 |
| PCTK1 | CDK16 | 68 |
| PCTK2 | CDK17 | 98 |
| PCTK3 | CDK18 | 97 |
| PDGFRA | PDGFRA | 97 |
| PDGFRB | PDGFRB | 94 |
| PDPK1 | PDPK1 | 86 |
| PFCDPK1(*P.falciparum*) | CDPK1 | 83 |
| PFPK5(*P.falciparum*) | MAL13P1.279 | 70 |
| PFTAIRE2 | CDK15 | 100 |
| PFTK1 | CDK14 | 98 |
| PHKG1 | PHKG1 | 95 |
| PHKG2 | PHKG2 | 100 |
| PIK3C2B | PIK3C2B | 80 |
| PIK3C2G | PIK3C2G | 57 |
| PIK3CA | PIK3CA | 90 |
| PIK3CA(C420R) | PIK3CA | 73 |
| PIK3CA(E542K) | PIK3CA | 55 |
| PIK3CA(E545A) | PIK3CA | 73 |
| PIK3CA(E545K) | PIK3CA | 55 |
| PIK3CA(H1047L) | PIK3CA | 84 |
| PIK3CA(H1047Y) | PIK3CA | 91 |
| PIK3CA(I800L) | PIK3CA | 72 |
| PIK3CA(M1043I) | PIK3CA | 80 |
| PIK3CA(Q546K) | PIK3CA | 70 |
| PIK3CB | PIK3CB | 64 |
| PIK3CD | PIK3CD | 61 |
| PIK3CG | PIK3CG | 76 |
| PIK4CB | PI4KB | 51 |
| PIKFYVE | PIKFYVE | 86 |
| PIM1 | PIM1 | 62 |
| PIM2 | PIM2 | 81 |
| PIM3 | PIM3 | 96 |
| PIP5K1A | PIP5K1A | 84 |
| PIP5K1C | PIP5K1C | 87 |
| PIP5K2B | PIP4K2B | 85 |
| PIP5K2C | PIP4K2C | 84 |
| PKAC-alpha | PRKACA | 93 |
| PKAC-beta | PRKACB | 100 |
| PKMYT1 | PKMYT1 | 100 |
| PKN1 | PKN1 | 100 |
| PKN2 | PKN2 | 89 |
| PKNB(*M.tuberculosis*) | pknB | 93 |
| PLK1 | PLK1 | 63 |
| PLK2 | PLK2 | 80 |
| PLK3 | PLK3 | 80 |
| PLK4 | PLK4 | 90 |
| PRKCD | PRKCD | 83 |
| PRKCE | PRKCE | 98 |
| PRKCH | PRKCH | 91 |
| PRKCI | PRKCI | 89 |
| PRKCQ | PRKCQ | 100 |
| PRKD1 | PRKD1 | 90 |
| PRKD2 | PRKD2 | 88 |
| PRKD3 | PRKD3 | 100 |
| PRKG1 | PRKG1 | 100 |
| PRKG2 | PRKG2 | 84 |
| PRKR | EIF2AK2 | 88 |
| PRKX | PRKX | 100 |
| PRP4 | PRPF4B | 71 |
| PYK2 | PTK2B | 92 |
| QSK | KIAA0999 | 55 |
| RAF1 | RAF1 | 98 |
| RET | RET | 100 |
| RET(M918T) | RET | 85 |
| RET(V804L) | RET | 88 |
| RET(V804M) | RET | 91 |
| RIOK1 | RIOK1 | 94 |
| RIOK2 | RIOK2 | 64 |
| RIOK3 | RIOK3 | 85 |
| RIPK1 | RIPK1 | 100 |
| RIPK2 | RIPK2 | 100 |
| RIPK4 | RIPK4 | 57 |
| RIPK5 | DSTYK | 69 |
| ROCK1 | ROCK1 | 52 |
| ROCK2 | ROCK2 | 71 |
| ROS1 | ROS1 | 91 |
| RPS6KA4(Kin.Dom.1-N-terminal) | RPS6KA4 | 100 |
| RPS6KA4(Kin.Dom.2-C-terminal) | RPS6KA4 | 62 |
| RPS6KA5(Kin.Dom.1-N-terminal) | RPS6KA5 | 86 |
| RPS6KA5(Kin.Dom.2-C-terminal) | RPS6KA5 | 100 |
| RSK1(Kin.Dom.1-N-terminal) | RPS6KA1 | 91 |
| RSK1(Kin.Dom.2-C-terminal) | RPS6KA1 | 97 |

TABLE 1-continued

ScanMAX panel of Senexin C at 2000 nM.

| DiscoveRx Gene Symbol | Entrez Gene Symbol | Percent Control |
|---|---|---|
| RSK2(Kin.Dom.1-N-terminal) | RPS6KA3 | 62 |
| RSK2(Kin.Dom.2-C-terminal) | RPS6KA3 | 65 |
| RSK3(Kin.Dom.1-N-terminal) | RPS6KA2 | 100 |
| RSK3(Kin.Dom.2-C-terminal) | RPS6KA2 | 91 |
| RSK4(Kin.Dom.1-N-terminal) | RPS6KA6 | 60 |
| RSK4(Kin.Dom.2-C-terminal) | RPS6KA6 | 96 |
| S6K1 | RPS6KB1 | 78 |
| SBK1 | SBK1 | 57 |
| SGK | SGK1 | 50 |
| SgK110 | SgK110 | 91 |
| SGK2 | SGK2 | 61 |
| SGK3 | SGK3 | 75 |
| SIK | SIK1 | 91 |
| SIK2 | SIK2 | 100 |
| SLK | SLK | 92 |
| SNARK | NUAK2 | 75 |
| SNRK | SNRK | 75 |
| SRC | SRC | 92 |
| SRMS | SRMS | 75 |
| SRPK1 | SRPK1 | 91 |
| SRPK2 | SRPK2 | 94 |
| SRPK3 | SRPK3 | 96 |
| STK16 | STK16 | 71 |
| STK33 | STK33 | 93 |
| STK35 | STK35 | 100 |
| STK36 | STK36 | 88 |
| STK39 | STK39 | 44 |
| SYK | SYK | 97 |
| TAK1 | MAP3K7 | 63 |
| TAOK1 | TAOK1 | 76 |
| TAOK2 | TAOK2 | 77 |
| TAOK3 | TAOK3 | 79 |
| TBK1 | TBK1 | 88 |
| TEC | TEC | 100 |
| TESK1 | TESK1 | 96 |
| TGFBR1 | TGFBR1 | 100 |
| TGFBR2 | TGFBR2 | 96 |
| TIE1 | TIE1 | 85 |
| TIE2 | TEK | 89 |
| TLK1 | TLK1 | 94 |
| TLK2 | TLK2 | 88 |
| TNIK | TNIK | 89 |
| TNK1 | TNK1 | 95 |
| TNK2 | TNK2 | 94 |
| TNNI3K | TNNI3K | 100 |
| TRKA | NTRK1 | 53 |
| TRKB | NTRK2 | 57 |
| TRKC | NTRK3 | 69 |
| TRPM6 | TRPM6 | 88 |
| TSSK1B | TSSK1B | 100 |
| TSSK3 | TSSK3 | 81 |
| TTK | TTK | 72 |
| TXK | TXK | 94 |
| TYK2(JH1domain-catalytic) | TYK2 | 62 |
| TYK2(JH2domain-pseudokinase) | TYK2 | 63 |
| TYRO3 | TYRO3 | 77 |
| ULK1 | ULK1 | 66 |
| ULK2 | ULK2 | 71 |
| ULK3 | ULK3 | 70 |
| VEGFR2 | KDR | 82 |
| VPS34 | PIK3C3 | 68 |
| VRK2 | VRK2 | 58 |
| WEE1 | WEE1 | 88 |
| WEE2 | WEE2 | 95 |
| WNK1 | WNK1 | 72 |
| WNK2 | WNK2 | 59 |
| WNK3 | WNK3 | 75 |
| WNK4 | WNK4 | 69 |
| YANK1 | STK32A | 76 |
| YANK2 | STK32B | 89 |
| YANK3 | STK32C | 100 |
| YES | YES1 | 100 |
| YSK1 | STK25 | 83 |
| YSK4 | MAP3K19 | 50 |
| ZAK | ZAK | 94 |
| ZAP70 | ZAP70 | 81 |

The effects on all the kinases that showed >65% inhibition by 2,000 nM Senexin C in this assay (CDK8, CDK19, HASPIN, MAP4K2, MYO3B) were then further investigated by measuring Kd values of Senexin C in the DiscoverX assay. The Kd assays were carried out in duplicates and the results for CDK8 and CDK19 are shown in FIGS. 2A-2D. The average Kd's from the duplicate measurements were as follows: CDK19, 44 nM; CDK8, 55 nM; HASPIN, 1,000 nM; MAP4K2, 940 nM; MYO3B, >30,000 nM. For comparison, the corresponding values determined for Senexin B (SNX2-1-165) were: CDK19, 23 nM; CDK8, 59 nM; HASPIN, 1,700 nM; MAP4K2, 570 nM (MYO3B was not inhibited). Hence, 6148 quinoline compound (Senexin C) is a highly selective inhibitor of CDK8/19.

Inhibition of CDK8/19 in Cell-Based Assays.

Figure 3B:
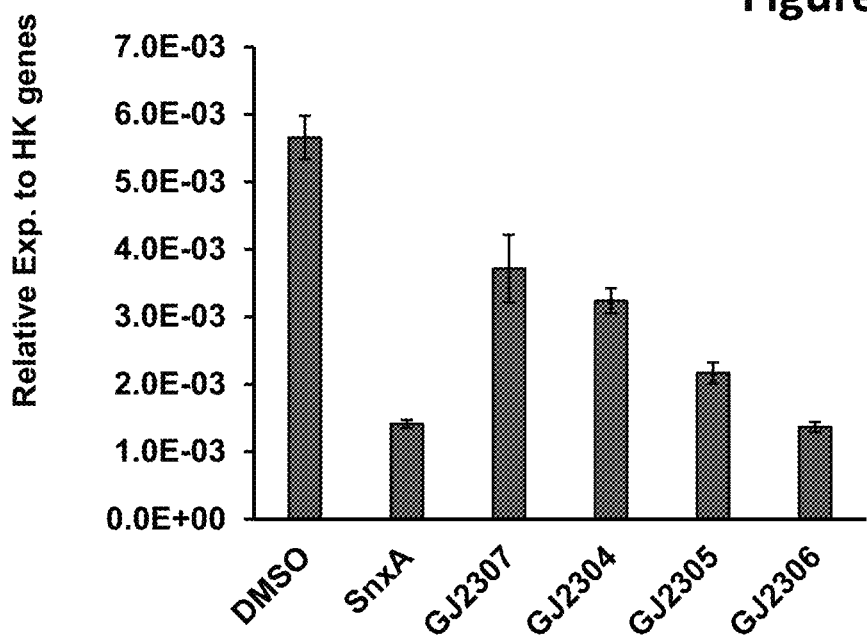
Figure 3C:
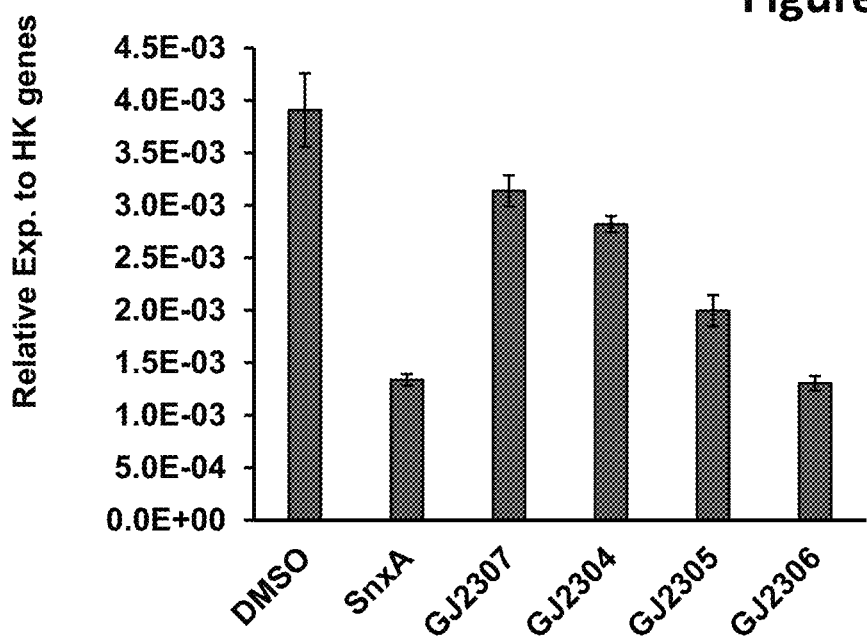

Two types of cell-based assays for CDK8/19 inhibition were used to test the efficacy of quinoline quinolone compounds described herein (FIG. 3A). The first cell-based assay, which measures the effects of CDK8/19 inhibitors on RNA levels of CDK8/19-regulated genes by quantitative reverse transcription-PCR (QPCR), is based on the ability of CDK8/19 inhibitors to suppress the induction of NFκB-inducible genes by TNFα and to inhibit basal expression of MYC in human embryonic kidney (HEK) 293 cells, as previously described. In this assay, 293 cells growing in DMEM (High-glucose) media supplemented with 10% FBS are pre-treated with the tested inhibitors or DMSO control for 1 hour and then treated with 10 ng/mL TNFα (an activator of NFκB) for 2 hours (in the presence or absence of the tested inhibitors), followed by RNA extraction and QPCR analysis of RNA expression of specific genes conducted as described (Chen et al., ibid), using housekeeping genes RPL13A and GAPDH as normalization standards. Table 2 and FIGS. 3B-3D show the extent of inhibition of MYC, CXCL1 and IL8 by 1 μM of Senexin A (SNX2-1-53), 6135 (GJ-2306) and quinoline compounds, 6138 (GJ-2305), 6136 (GJ-2307), and 6134 (GJ-2304). All the quinoline derivatives inhibited the expression of all three genes.

Figure 4B:
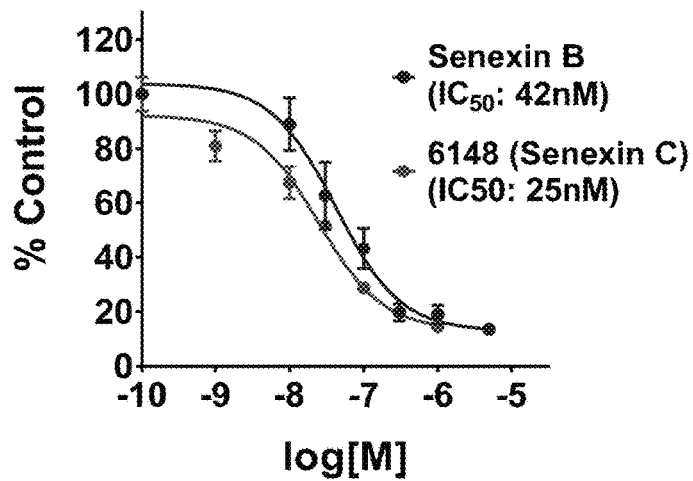
FIGS. 4B-4D compares the effect of different concentrations of 6148 (Senexin C) and Senexin B on MYC (FIG. 4B), CXCL1 (FIG. 4C), and CXCL8 (IL8) (FIG. 4D) gene expression in TNFα-treated 293 cells (QPCR analysis).
Figure 4C:
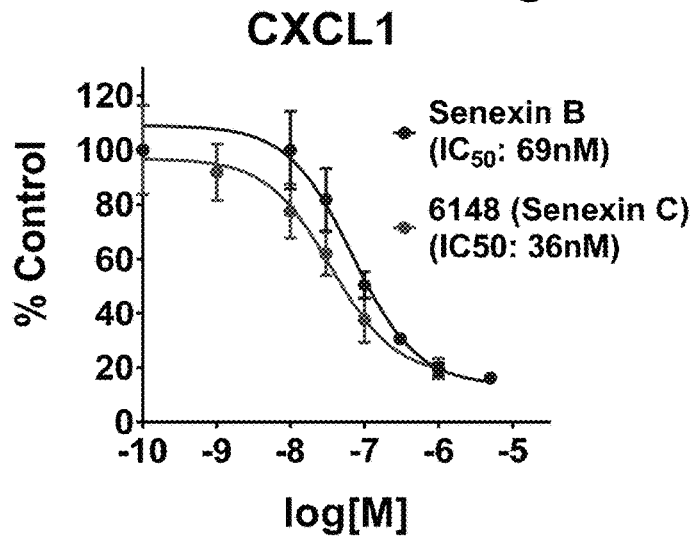
Figure 4D:
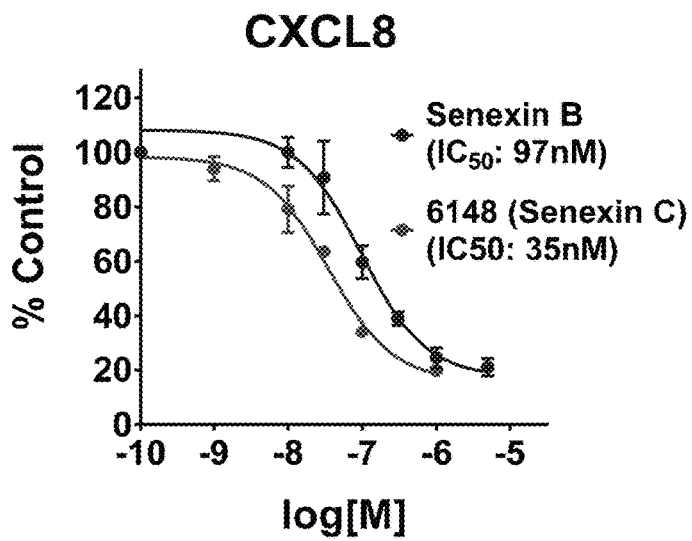

FIGS. 4B-4D compare the effects of different concentrations of 6148 (Senexin C) and Senexin B, as shown in FIG. 4A, in the same assay. Expression of all three genes was inhibited by Senexin C, with IC50 values from 25-35 nM.

TABLE 2

Inhibition of MYC and NFκB-inducible gene expression in HEK293 cells (QPCR).

| Compound | Inhibition at 1 μM (% Ctrl) | | |
|---|---|---|---|
| | MYC | CXCL1 | IL8 |
| Senexin A | 24.94% | 34.19% | 29.53% |
| 6136/GJ2307 | 65.64% | 80.30% | 74.10% |
| 6134/GJ2304 | 57.22% | 72.16% | 62.12% |
| 6138/GJ2305 | 38.30% | 51.07% | 45.05% |
| 6135/GJ2306 | 24.15% | 33.36% | 29.25% |

Figure 5A:
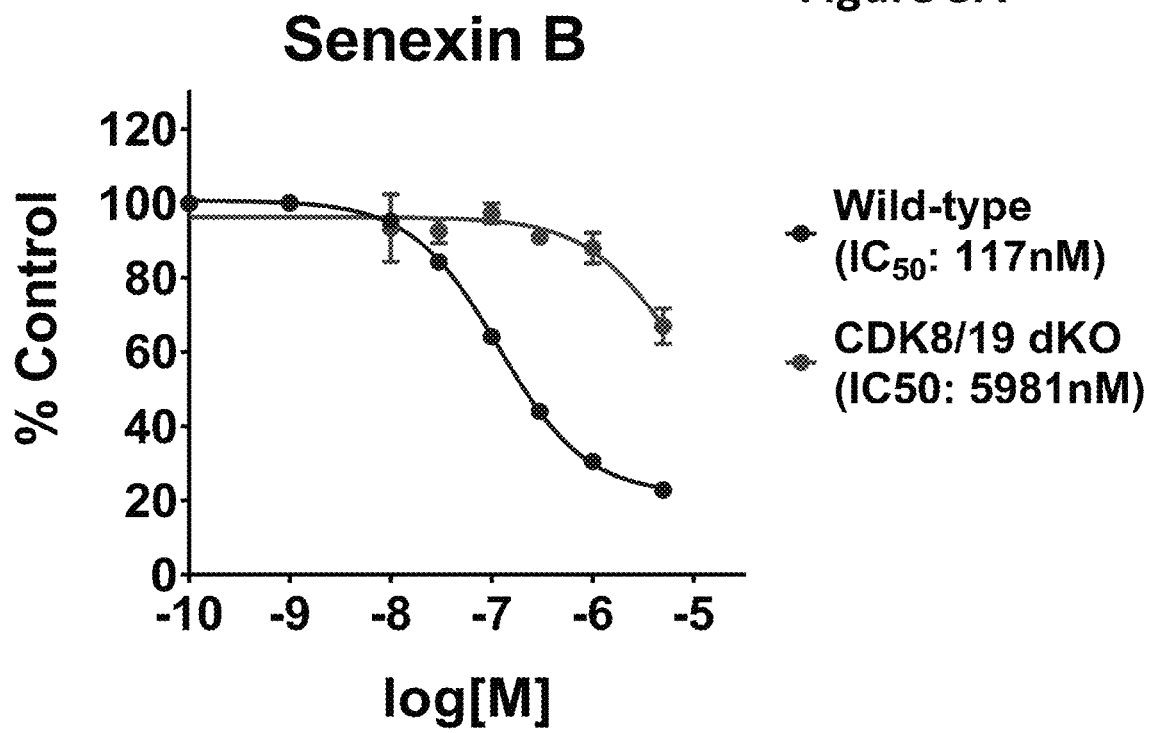
FIGS. 5A-5D show the concentration-dependent effect of Senexin B (FIG. 5A), Senexin C (FIG. 5B), TPCK (FIG. 5C), and dinaciclib (FIG. 5D) in parental (wild-type, blue lines) and CDK8/19 deficient (double-knockout, red lines) reporter cells.
Figure 5B:
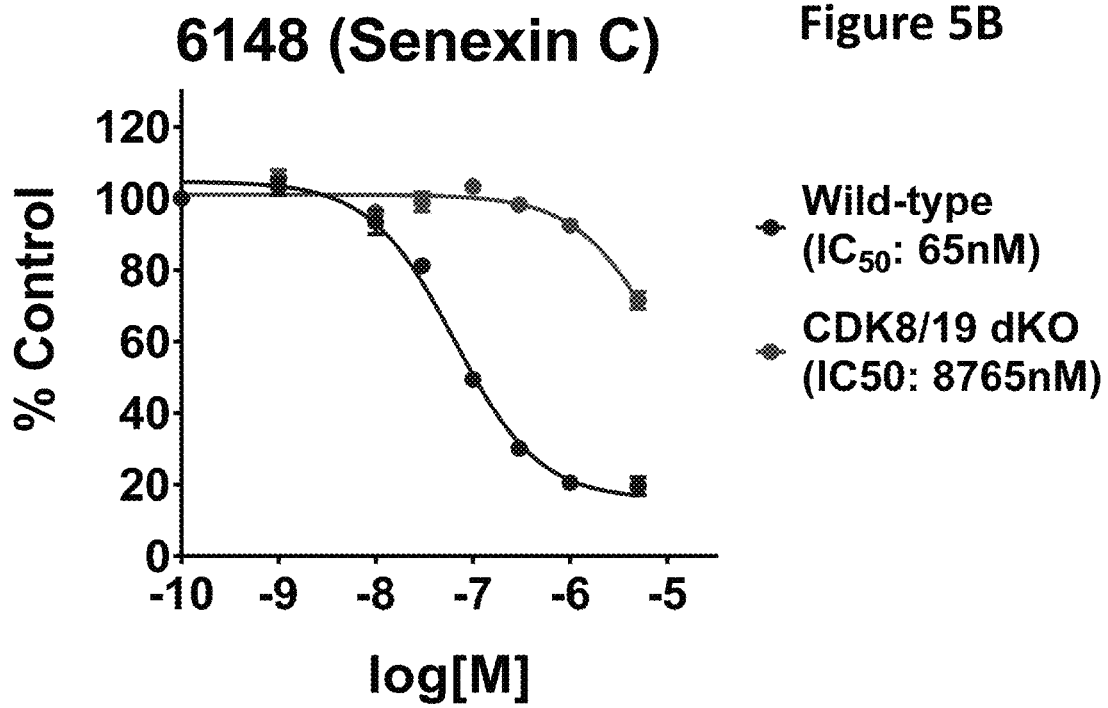
Figure 5C:
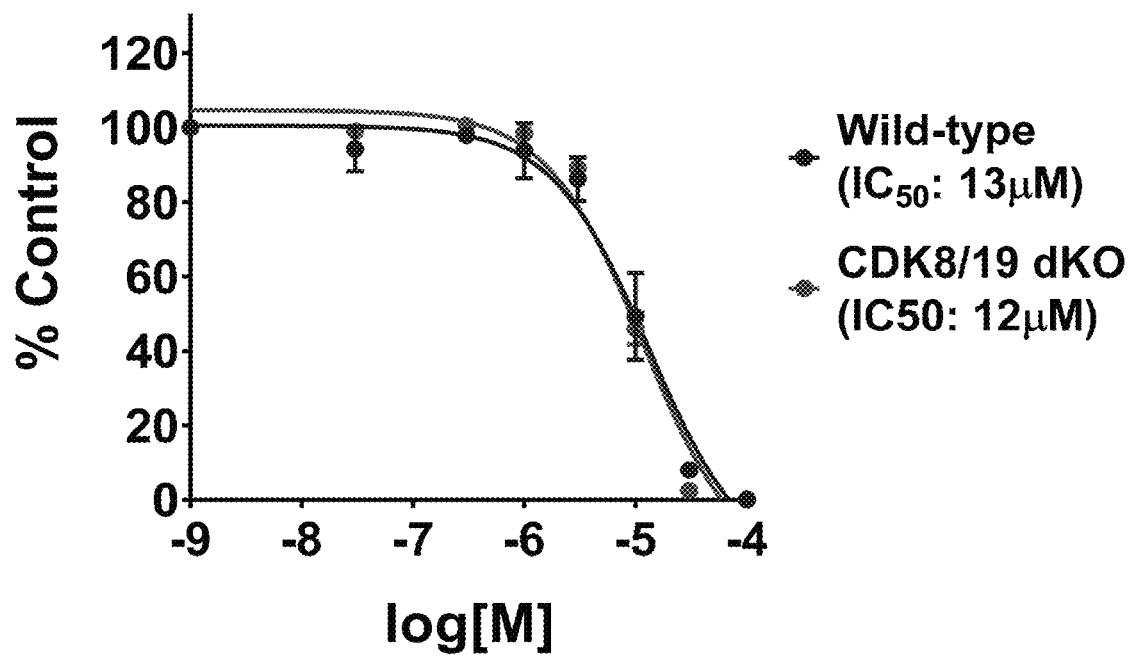
Figure 5D:
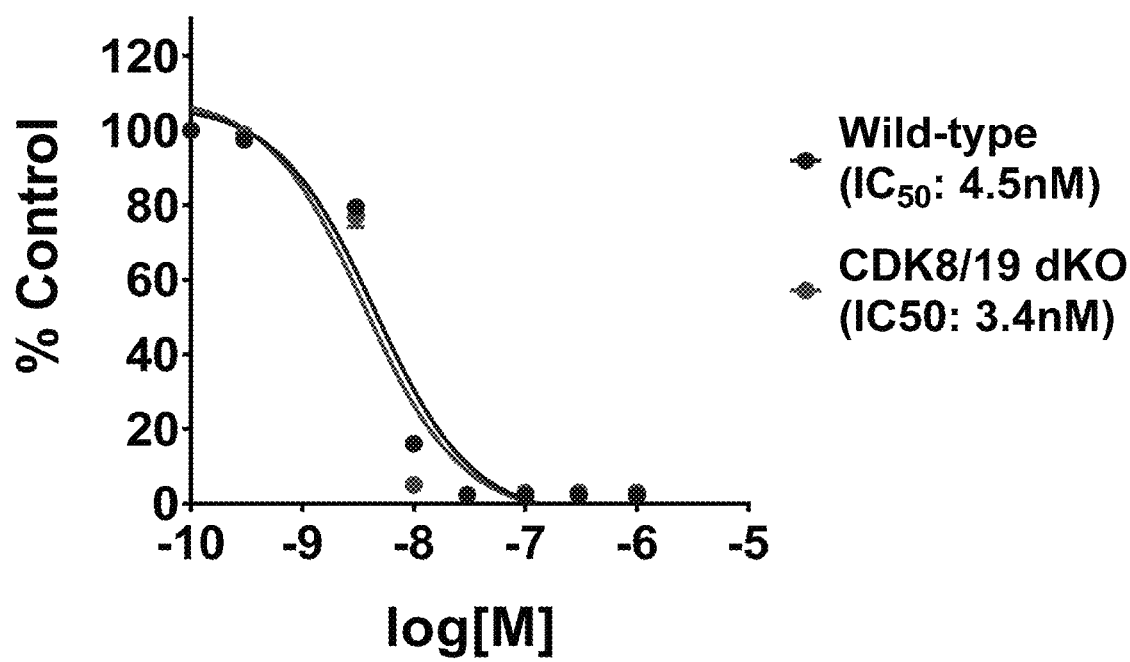

The second cell-based assay measures the effects of CDK8/19 on the expression of firefly luciferase reporter from a NFκB-dependent promoter in 293 cells. Lentiviral vector pHAGE-NFκB-TA-LUC-UBC-dTomato-W (Addgene #49335) was introduced into 293 cells and a clonal cell line showing the strongest induction of luciferase expression upon TNFα treatment was established and used as the reporter cell line. As a control for CDK8/19 dependence of NFκB inhibition, we have also introduced the same reporter construct into 293 cells with CRISPR/CAS9 knockout of both CDK8 and CDK19. FIGS. 5A-5B shows the effects of different concentrations of Senexin B (FIG. 5A) and 6148 (Senexin C) (FIG. 5B) in both parental (wild-type) and CDK8/19 deficient (double-knockout) reporter cells. The IC50 values in this assay were >50 times higher in CDK8/19-deficient cells, demonstrating that the inhibitory effects of both compounds depend on the presence of CDK8/19. In contrast, for the canonical NFκB inhibitor TPCK (FIG. 5C) and pan-CDK inhibitor Dinaciclib (FIG. 5D), the IC50 values are almost the same between wild-type and double-knockout cells.

The IC50 values for different compounds measured in the NFκB reporter assay in parental 293-derived reporter cell line are listed in Table 3. These results show that the quinoline derivatives are 1.6~1.8-fold more potent than the corresponding quinazoline compounds in the cell-based assay (IC50 117 nM for Senexin B vs 65 nM for 6148 (Senexin C) and 355 nM for Senexin A vs 217 nM for 6135) and that the $R^2$ group of 6160 provides a similar activity to the $R^2$ group of 6148. Substituting $R^1$ group of 6135 from carbonitrile to nitro retains the inhibitory activity (although at ~1.6-fold reduced level). However, when the carbonitrile group was replaced with Cl (6145/GJ-2328), Br (6146/GJ-2329), I (6147, wGJ-2330) or CF3 (6150/GJ-2338), <15% inhibition of NFκB reporter activity was detected at 1 μM concentrations, indicating that these substitutions are unfavorable for the inhibitory activity of 6136. The same bromo and iodo substitutions in the quinazoline context result in active compounds however.

TABLE 3

Exemplary Quinoline based CDK8 inhibitors.
Quinoline Core Structure

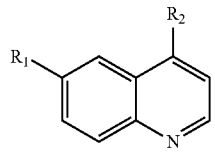

| ID | GK ID | R1 | R2 Name | R2 Structure | HEK293 NFKB CDK8 Reporter IC$_{50}$ |
|---|---|---|---|---|---|
| 6160 | GJ-2344 | Carbonitrile | 2-(4-(1,4-diazepan-1-yl)phenyl)-N,N-dimethylacetamino | | 82 nM |
| 6148 | GJ-2331/2335 | Carbonitrile | 2-[6-(4-Methyl-piperazine-1-carbonyl)-naphthalen-2-yl]-ethylamino} | | 65 nM |
| 6168 | GJ-2359 | Carbonitrile | 4-(1,4-diazepan-1-yl)-N,N-dimethylbenzamino | | 203 nM |
| 6138 | GJ-2309 | Carbonitrile | Benzylamino | | Not determined |

TABLE 3-continued

Exemplary Quinoline based CDK8 inhibitors.
Quinoline Core Structure

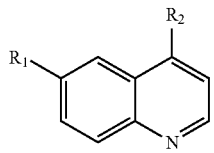

| ID | GK ID | R1 | R2 Name | R2 Structure | HEK293 NFKB CDK8 Reporter IC$_{50}$ |
|---|---|---|---|---|---|
| 6136 | GJ-2307 | Carbonitrile | Isopropylamino | | Not determined |
| 6134 | GJ-2304 | Carbonitrile | Propylamino | | Not determined |
| 6135 | GJ-2306/2353 | Carbonitrile | Phenethylamino | | 217 nM |
| 6145 | GJ-2328 | Chloro | Phenethylamino | | N.A. (8% inh. at 1 uM) |
| 6146 | GJ-2329 | Bromo | Phenethylamino | | N.A. (10% inh. at 1 uM) |
| 6147 | GJ-2330 | Iodo | Phenethylamino | | N.A. (8% inh. at 1 uM) |
| 6149 | GJ-2334/2354 | Nitro | Phenethylamino | | 346 nM |
| 6150 | GJ-2338 | Trifluoromethyl | Phenethylamino | | N.A. (10% inh. at 1 uM) |
| 6161 | GJ-2346 | Hydrogen | Phenethylamino | | No determined |
| 6164 | GJ-2356 | Amino | Phenethylamino | | N.A. (5% inh. at 5 uM) |
| 6204 | GW5146 | Carbonitrile | (2-(2-aminoethyl)quinolin-6-yl)(4-methylpiperazin-1-yl)methanone | | 195 nM |

TABLE 3-continued

Exemplary Quinoline based CDK8 inhibitors.
Quinoline Core Structure

| ID | GK ID | R1 | R2 Name | R2 Structure | HEK293 NFKB CDK8 Reporter IC$_{50}$ |
|---|---|---|---|---|---|
| 6205 | GW5149 | Formamide | Phenethylamino | | N.A. |
| 6206 | GW5151 | Acetamide | Phenethylamino | | N.A. |
| 6219 | HC1607 | Carbonitrile | 6-(2-aminoethyl)-N,N-dimethyl-2-naphthamide | | 103 nM |
| 6216 | HC1658 | Carbonitrile | (6-(2-aminoethyl)naphthalen-2-yl)(4-(3-hydroxypropyl)piperazin-1-yl)methanone | | 117 nM |
| 6283 | HI8625 | Carbonitrile | (6-(2-aminoethyl)naphthalen-2-yl)(piperazin-1-yl)methanone | | 449 nM |

Senexin C Shows Increased Stability of CDK8/19 Inhibition.

Figure 6A:
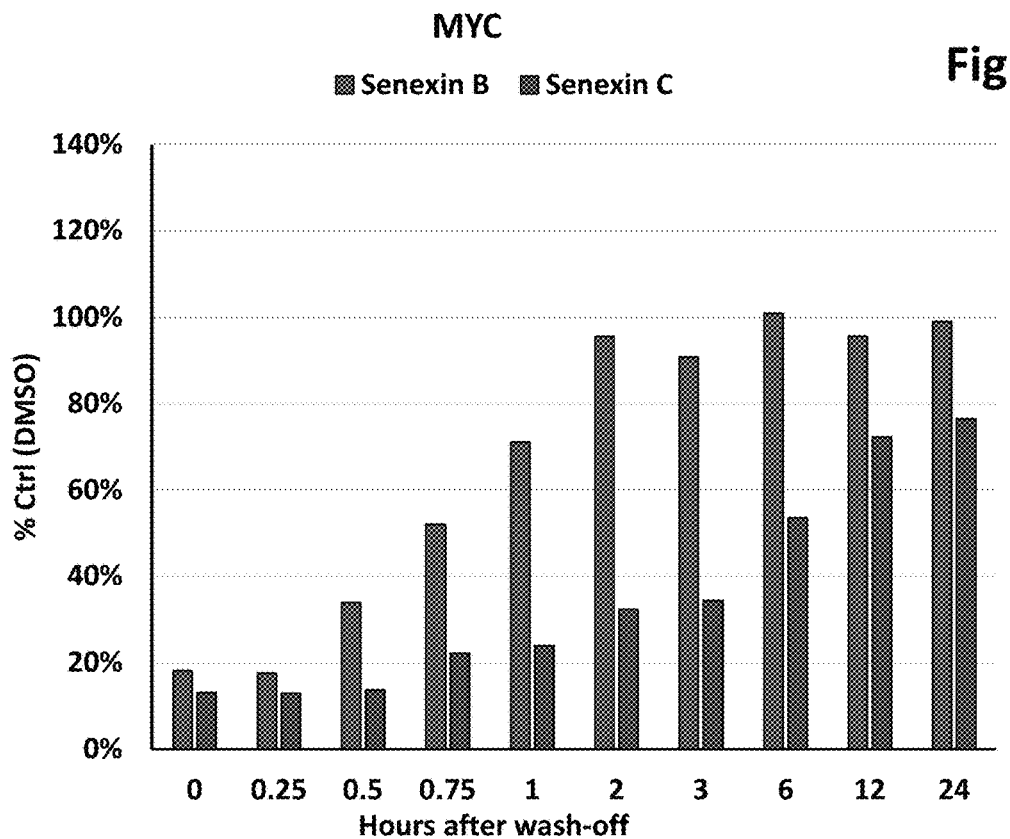
FIGS. 6A-6B shows the restoration of MYC (FIG. 6A) and JUN (FIG. 6B) expression in 293 cells treated with Senexin B and Senexin C, after the wash-off of the compounds.
Figure 6B:
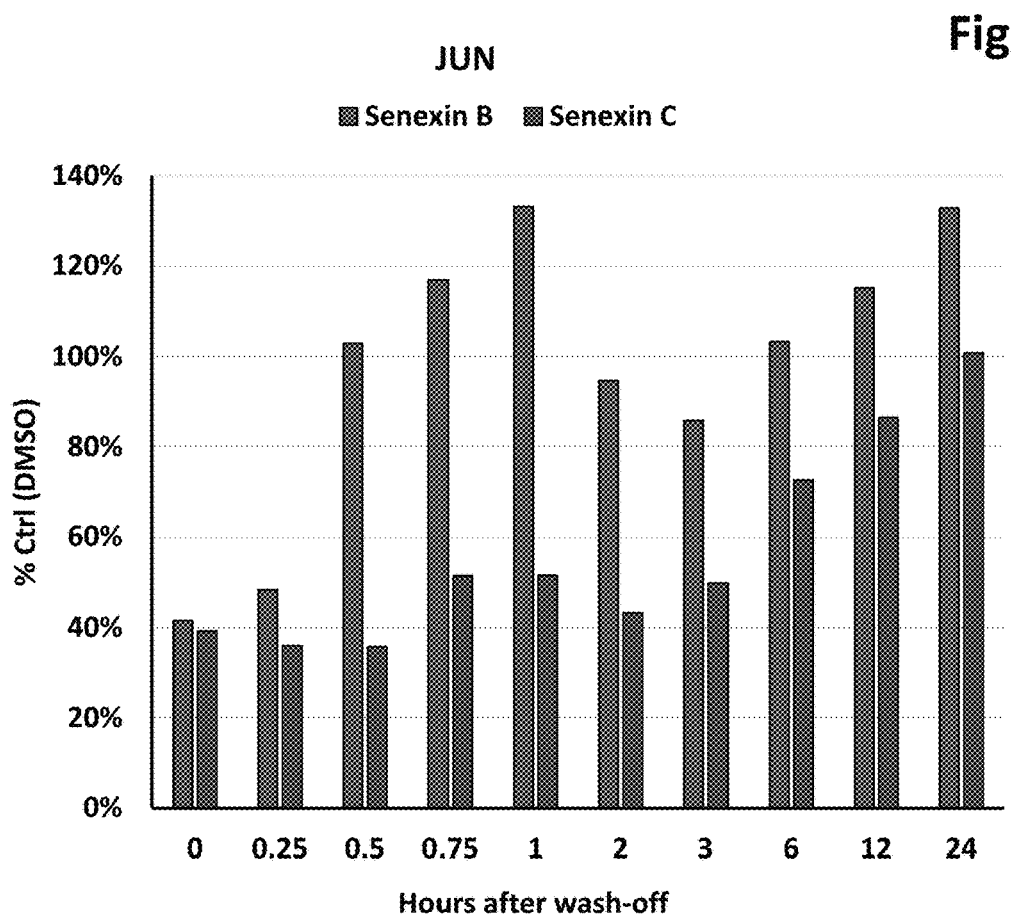

To compare the stability of CDK8/19 inhibition in mammalian cells by Senexin B and its quinoline derivative 6148 (Senexin C), we treated 293 cells with 1 µM of each inhibitor (or DMSO control) for 2 hours, at which time cells were washed twice with drug-free media and exposed to drug-free media. RNA was extracted at different time points after wash-off (up to 24 hrs) and expression of MYC and JUN genes that are CDK8/19-dependent in these cells was measured by QPCR. As shown in FIGS. 6A-6B, following Senexin B treatment and wash-off, JUN (FIG. 6B) expression was fully restored after 45 min and MYC (FIG. 6A) expression after 2 hrs. In contrast, after Senexin C treatment and wash-off, the effects of Senexin C were largely retained for at least 6 hrs after wash-off. Hence, 6148 (Senexin C) offers a greatly increased duration of CDK8/19 inhibition in cells relative to Senexin B.

Senexin C Shows Improved Stability in Human Hepatocytes.

Figure 7:
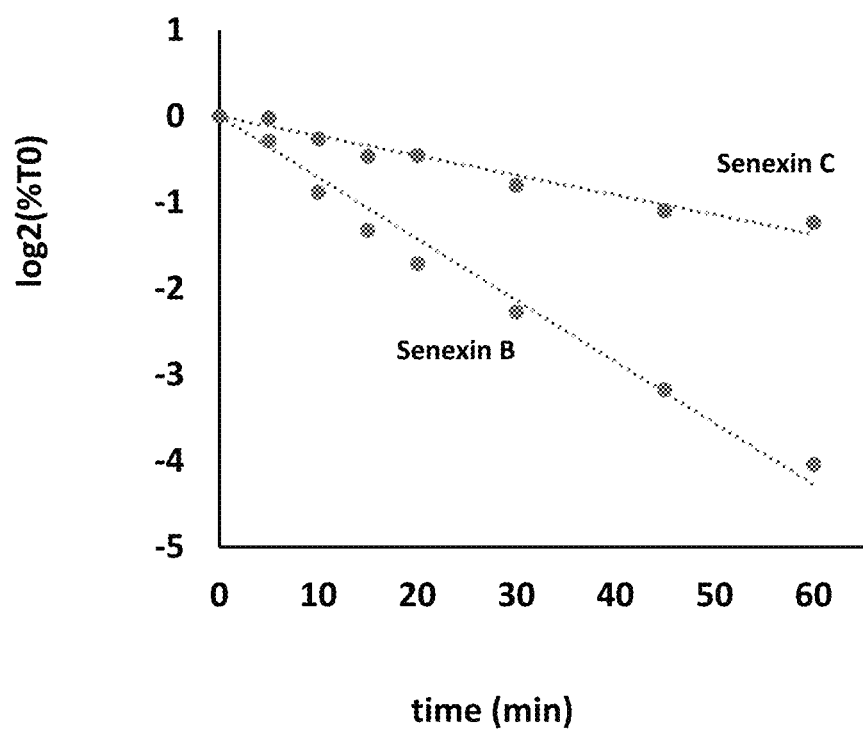
FIG. 7 shows the kinetics of metabolic conversion of Senexin B and Senexin C in hepatocyte cultures.

Metabolic stability of Senexin B and its quinoline derivative Senexin C was compared in human hepatocytes obtained from Xenotech (H1500.H15B_HC4-6). Senexin B and Senexin C were added to hepatocytes in hepatocyte incubation media (Xenotech) at 2 µM and incubated at 37° C. Hepatocyte suspension aliquots (30 uL) were collected at different time points and the concentrations of Senexin B and Senexin C were measured by LC/MS/MS using a series of standards prepared in hepatocyte incubation media. As shown in FIG. 7, the metabolic conversion rate of Senexin C in cultured hepatocytes was greatly decreased relative to Senexin B.

Senexin C Shows Increased Half-Life in Mice.

To measure mouse pharmacokinetics (PK), Senexin C dissolved in 5% Dextrose was administered intraperitoneally (i.p.) to female FVB mice at 19 mg/kg. Blood samples were collected at different time points (5 mice per time point) and Senexin C concentration in the serum was measured by LC/MS/MS. The resulting PK curve is shown in FIGS. 8Ai-8Aii. The results for Senexin C are compared with the data from a separate similar study with Senexin B, which was administered i.p. at 27 mg/kg to male Balb/c mice (FIGS. 8Bi-8Bii). The calculated PK parameters from both experiments are presented in Table 4.

TABLE 4

Comparison of i.p. pharmacokinetics parameters of Senexin B and Senexin C.

|  | Senexin B | Senexin C |
|---|---|---|
| Dose (mg/kg) | 27 | 19 |
| Cmax (ng/mL) | 4248 | 1161 |
| AUC (ng * hr/mL) | 1760.53 | 1573.33 |
| elimination rate k (hr−1) | 3.99 | 0.94 |
| t1/2 (hr) | 0.17 | 0.74 |
| bioavailability (F %) | 57% | 73% |

These results show that the quinoline derivative Senexin C has >4-fold higher half-life and lower elimination rate than Senexin B. The lower elimination rate together with a greatly increased stability of CDK8/19 inhibition at the cellular level indicate that replacing quinazoline with quinoline offers a major improvement to this class of CDK8/19 inhibitors.

Inhibition of CDK8/19 in Cell-Based Assays.

Figure 9A:
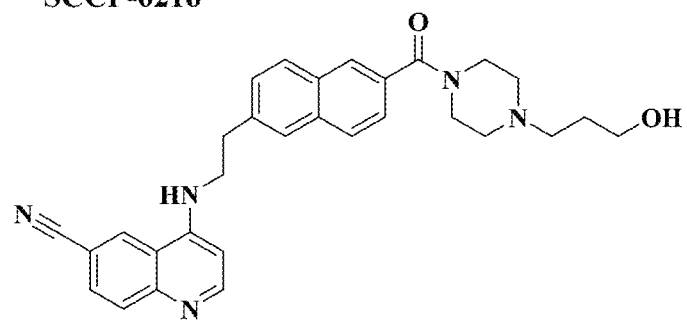
FIG. 9A shows several exemplary compounds of the invention.
Figure 9A:
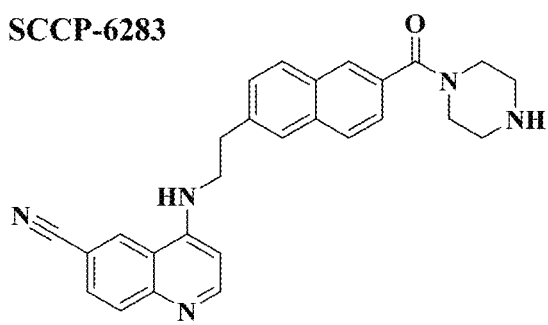
Figure 9A:
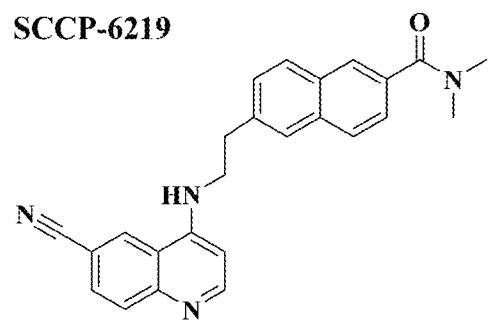
Figure 9B:
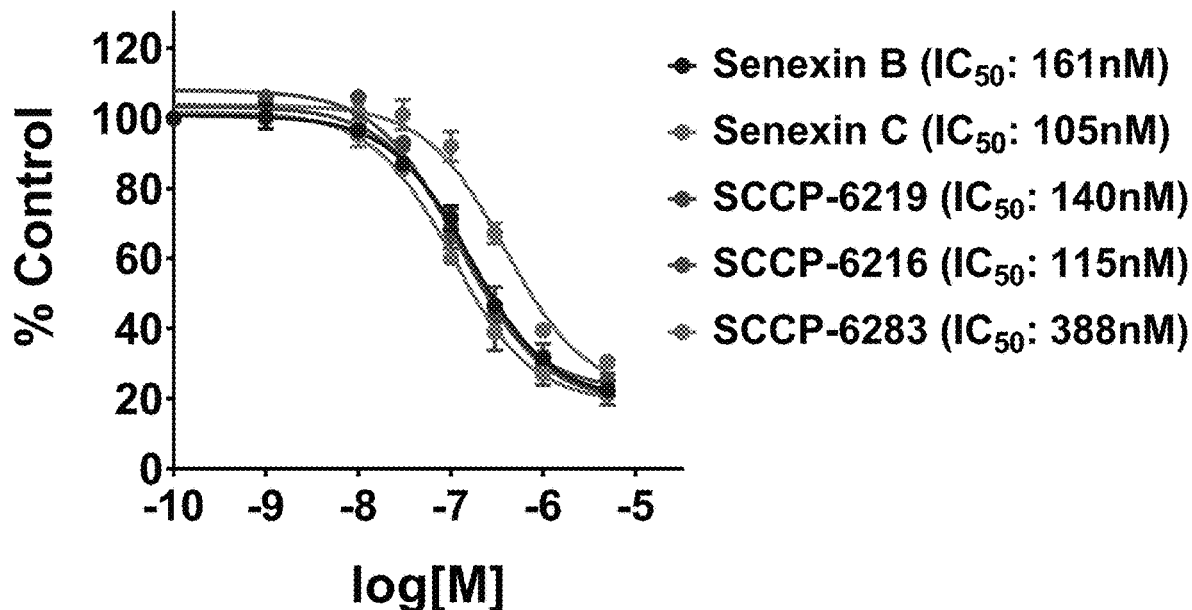
FIGS. 9B and 9C show inhibition of CDK8/19 in HEK293 (FIG. 9B) and LNCaP-C4-2 (FIG. 9C) cellular assays.

FIG. 9A shows the chemical structures of SCCP-6216, SCCP-6283, and SCCP-6219. FIG. 9B compares the IC50 values of these compounds in the NFκB-dependent reporter assay in human embryonic kidney (HEK) 293 cells. The $R^2$ groups of 6219 and 6216 provide similar activity to the $R^2$ group of 6148 (Senexin C) while the $R^2$ group of 6283 provides 2-3 fold less activity than the $R^2$ group of Senexin C.

Figure 9C:
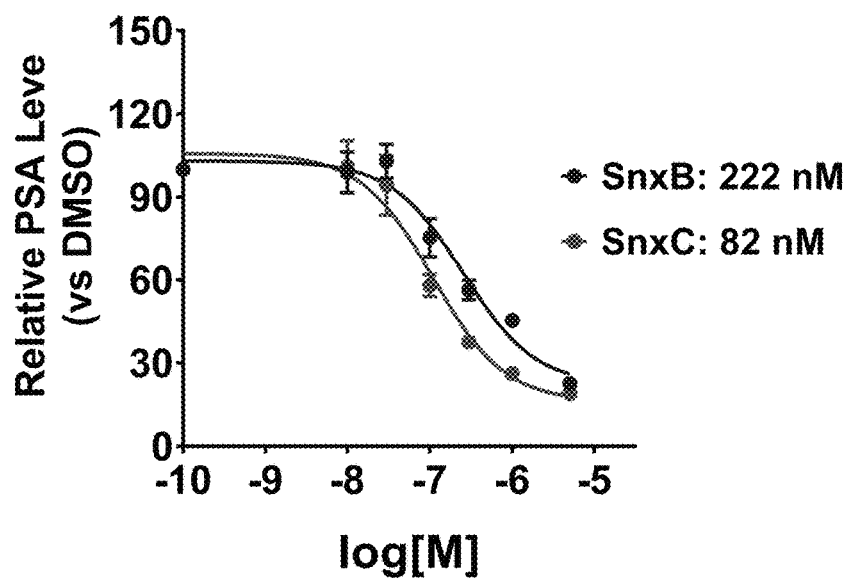

FIG. 9C compares the effects of different concentrations of Senexin C and Senexin B in another CDK8/19-dependent cell-based assay. Prostate cancer LNCaP-C4-2 cells were treated with different concentrations of the compounds for 4 days and the conditioned media were collected for quantification of prostate specific antigen (PSA) with an ELISA kit. The result shows that Senexin C is ~3-fold more potent than Senexin B in inhibition of PSA production in prostate cancer cells.

Pharmacokinetics of Senexin C

Figure 10A:
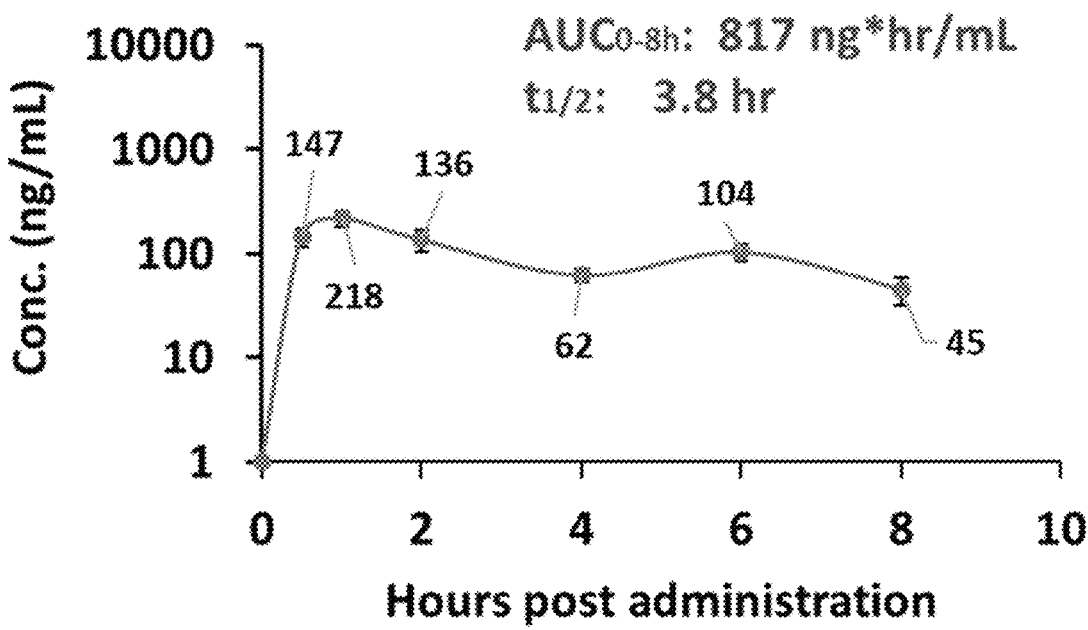
FIGS. 10A-10B show the pharmacokinetics of Senexin C with oral (FIG. 10A) and i.p.

To measure pharmacokinetics (PK), Senexin C dissolved in 5% Dextrose was administered orally (p.o.) to female FVB mice at 30 mg/kg. Blood samples were collected at different time points (5 mice per time point) and Senexin C concentration in the serum was measured by LC/MS/MS. The resulting PK curve is shown in FIG. 10A. The result shows that the oral administration of Senexin C increases half-time 4-5 times (3.8 hr vs 0.74 hr) when compared with previous i.p. PK curve (FIGS. 8Ai-8Aii).

Figure 10B:
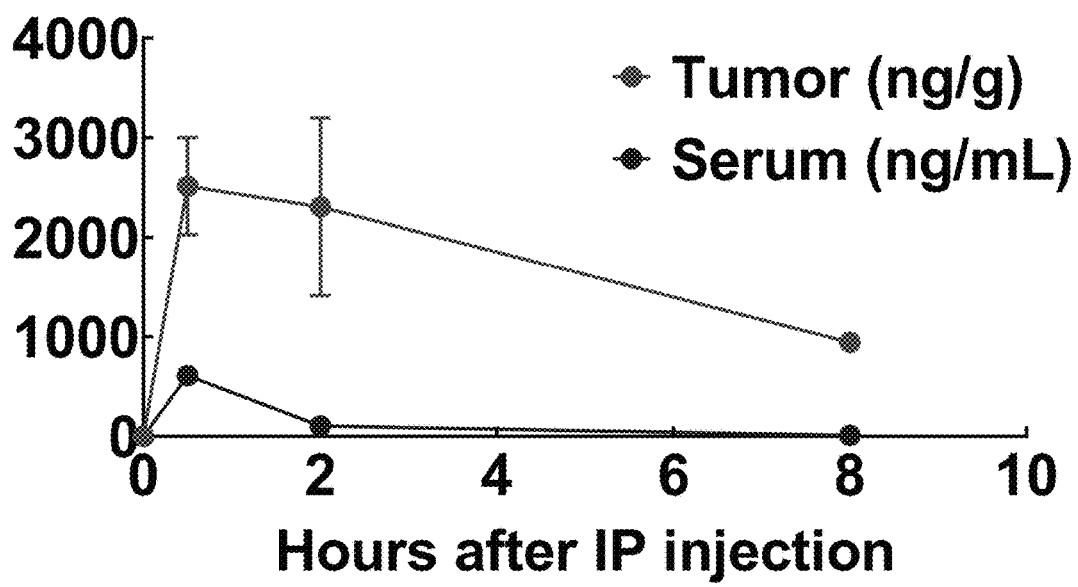

To evaluate the PK of Senexin C in tumor tissues, Senexin C dissolved in 5% Dextrose was administered i.p. to male NcrNU mice bearing 22rv1 xenograft tumors (300~500 mm^3) at 20 mg/kg. Both blood and tumor samples were collected at three different time points (3 mice per time point) after administration and Senexin C concentration in the serum and tumor tissue was measured by LC/MS/MS. As shown in FIG. 10B, the amount of Senexin C in tumor tissue is 5-10 times higher than the amount in blood with a much slower clearance rate.

In Vivo Effects of Senexin C in Castration-Refractory Prostate Cancer.

Figure 11A:
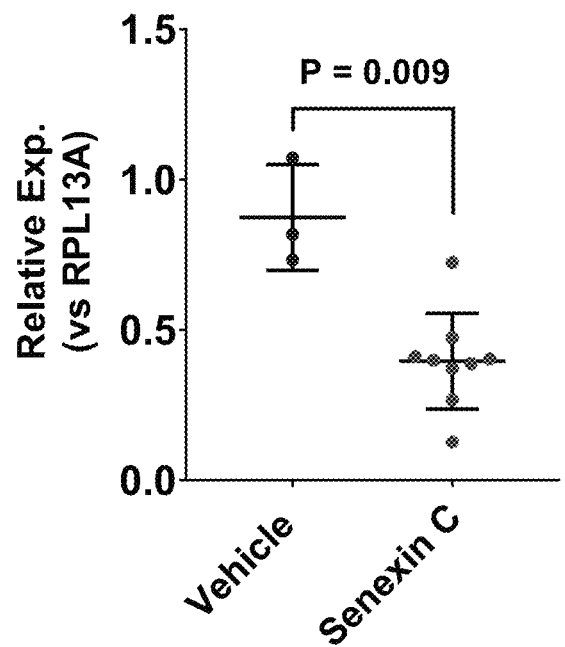
FIGS. 11A-11B shows the effect of Senexin C against castration-refractory prostate cancer on the PSA mRNA levels (FIG. 11A) and concentration of Senexin C in tumor tissues and serum (FIG. 11B).
Figure 11B:
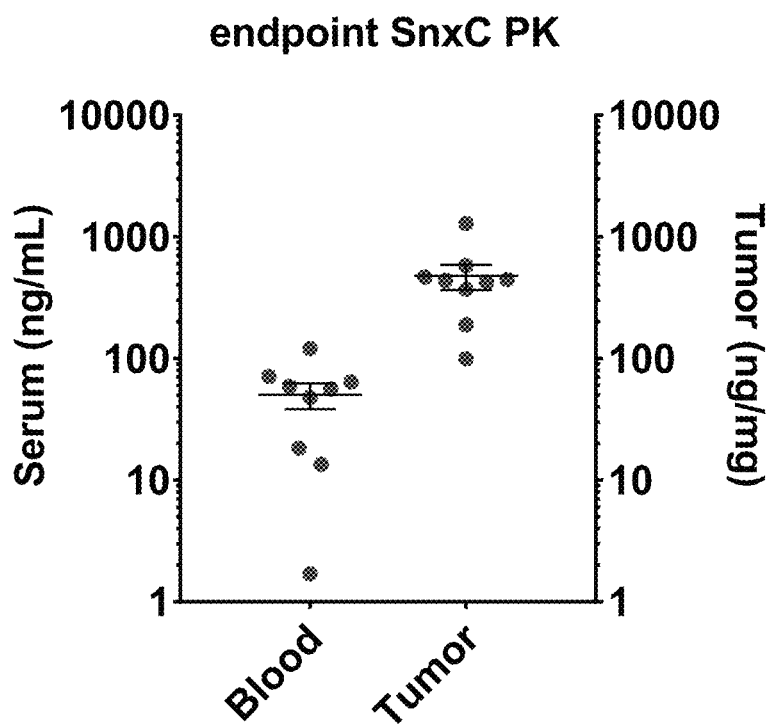

CDK8/19 inhibition decreases the expression of certain androgen-receptor (AR) inducible genes including PSA, the most common marker of prostate cancer, and the growth of castration-refractory prostate cancers (CRPC). The in vivo effects of Senexin C on PSA expression by C4-2 cells were analyzed after treatment of male NcrNU mice bearing C4-2 xenografts (grouped based on tumor sizes) for 4 days at 40 mg/kg administered orally daily. The PSA mRNA levels in the tumor were strongly decreased by treatment with Senexin C (FIG. 11A). Measurement of serum and tumor PK at the endpoint of the study (6-7 hours post last dose) shows higher Senexin C drug concentration in tumor tissues (FIG. 11B).

Effects of Senexin C on Breast Cancer Metastasis.

Figure 12A:
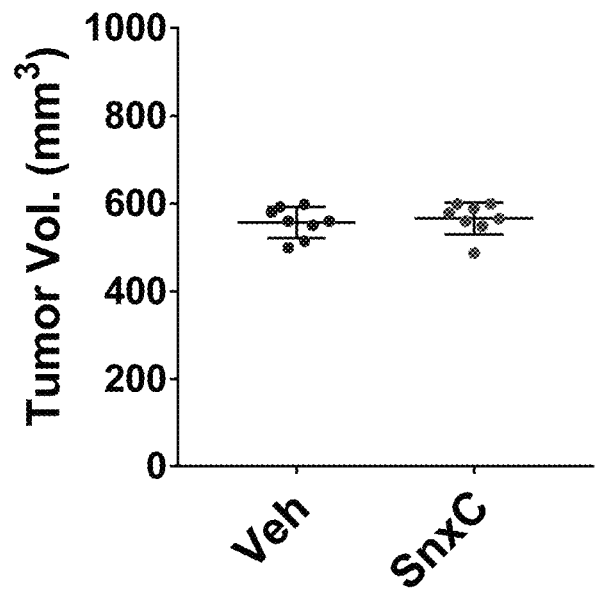
FIGS. 12A-12B show the effect of Senexin C against breast cancer metastasis.
Figure 12B:
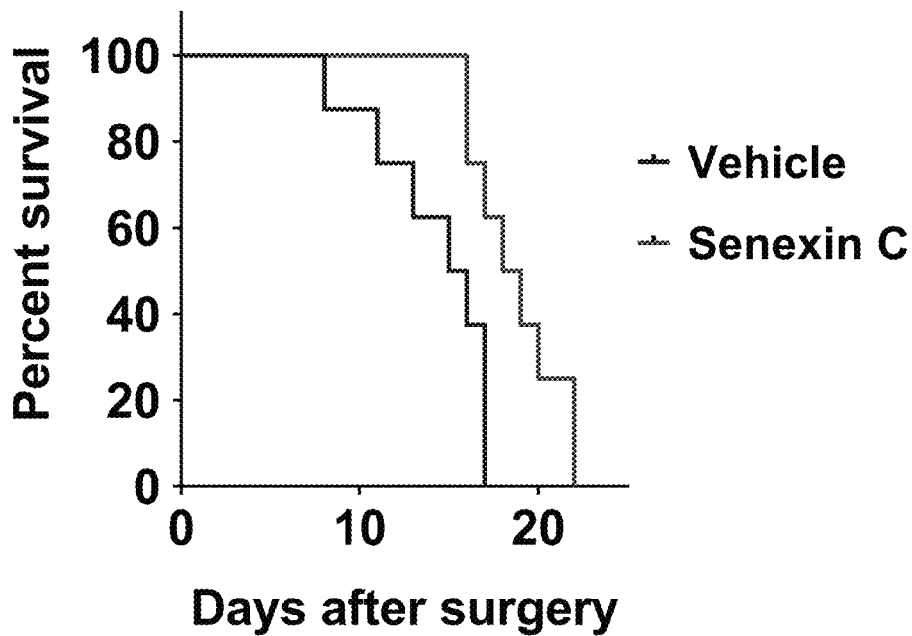

4T1 is a murine triple-negative breast cancer (TNBC) cell line, which is highly metastatic to the lungs. 4T1 cells were injected orthotopically in the mammary fat pad of female Balb/c mice and the primary tumors were surgically removed when tumor sizes reach 500-600 mm³. Mice were then separated into two groups (FIG. 12A, n=8), which were then treated with vehicle (5% dextrose) or Senexin C (40 mg/kg, oral, b.i.d.). Treatment with Senexin C significantly increased mouse survival of the metastatic disease (FIG. 12B), indicating the utility of quinolone inhibitors of CDK8/19 for the treatment of cancer metastasis linked to CDK8/19 activity.

Comparison of Activity

The CDK8/19 inhibiting and in vitro leukemia-suppressing activities of quinolone-based compounds are summarized in Table 5.

In vitro binding of the compounds to the ATP pocket of CDK8 in complex with Cyclin C was carried out by LanthaScreen® Eu Kinase Binding Assay based on the binding and displacement of a proprietary, Alexa Fluor® 647-labeled, ATP-competitive kinase inhibitor scaffold (kinase tracer) to the kinase of interest. The binding of the tracer to the kinase is detected using a europium-labeled anti-tag antibody, which binds to the kinase of interest. Simultaneous binding of both the tracer and antibody to the kinase results in a high degree of FRET (fluorescence resonance energy transfer) from the europium (Eu) donor fluorophore to the Alexa Fluor® 647 acceptor fluorophore on the kinase tracer. The binding of an inhibitor to the kinase competes for binding with the tracer, resulting in a loss of FRET.

The cell-based assay for the inhibition CDK8/19-mediated NFκB-driven transcription was carried out by measuring the effects of CDK8/19 on the expression of firefly luciferase reporter from a NFκB-dependent promoter in 293 cells. This assay measures the effects of CDK8/19 on the expression of firefly luciferase reporter from a NFκB-dependent promoter in 293 cells. Lentiviral vector pHAGE-NFκB-TA-LUC-UBC-dTomato-W (Addgene #49335) was introduced into 293 cells and a clonal cell line showing the strongest induction of luciferase expression upon TNFα treatment was established and used as the reporter cell line. Luciferase expression was stimulated by the addition of TNFα and the effects of different concentrations of the tested compounds on TNFα induced luciferase expression was measured as described by Li, J., Ji, H., Porter, D. C., Broude, E. V., Roninson, I. B., and Chen, M. (2019), Cells 8, 1208.

The anti-leukemic activity was evaluated with a MV4-11 assay. The population of MV4-11 cells, which depend on CDK8/19 for their proliferation, was made to express Luciferase and ZsGreen by lenvtiral infection with pHIV-Luc-ZsGreen, to enable leukemia growth analysis by bioluminescence imaging (BLI). The initial Luciferase-ZsGreen transduced cell population was sorted for ZsGreen positivity with fluorescence activated cell sorting. The MV4-11 assay was performed in 96-well plates by treating the MV4-11-Luc cells with testing compounds at different concentrations for 7 days, followed by BLI to quantify the effects of test articles on cell proliferation.

The anti-leukemic activity was also evaluated with a HL60 assay. The HL60 assay was performed by a similar procedure as MV4-11 assay. A derivative of the HL-60 leukemia cell line was generated to express Luciferase and ZsGreen by lentiviral infection with pHIV-Luc-ZsGreen, to enable leukemia growth analysis by bioluminescence imaging (BLI). The initial Luciferase-ZsGreen transduced cell population was sorted for ZsGreen positivity with fluorescence activated cell sorting and individual clones were tested for luciferase expression. The clonal HL60-Luc cell line was found to have the strongest and sustained luciferase expression and, in contrast to the parental HL60 population, this cell line was sensitive to all the tested CDK8/19 inhibitors. The HL-60 assay was performed in 96-well plates by treating the HL60-Luc cells with testing compounds at different concentrations for 7 days, followed by BLI to quantify the effects of test articles on cell proliferation.

The results of these assays, listed in Table 5, reveal the compounds that are potent in CDK8/19 inhibition in cell-free and different cell-based assays.

TABLE 5

Comparison of activity

| SCCP ID | Structure | Chemical formula | Mol. wt | IC50 (293-NFKB-Luc) | IC50 (MV4-11-Luc) | IC50 (HL60-Luc) | IC50 (LanthaScreen) |
|---|---|---|---|---|---|---|---|
| 6148 | 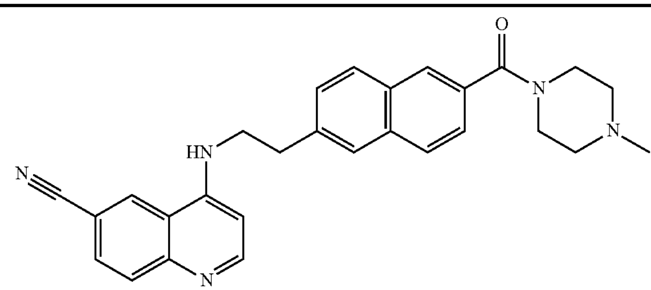 | C28H27N5O | 449.56 | 55 nM | 117 nM | 114 nM | 3.8 nM |
| 6219 | 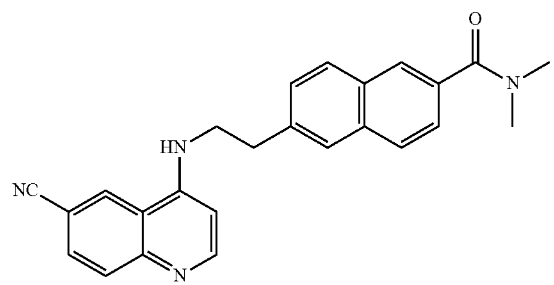 | C25H22N4O | 394.48 | 106 nM | 81 nM | 77 nM | 3.7 nM |
| 6216 | 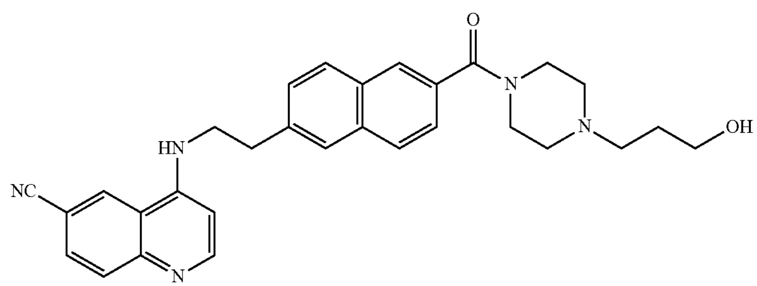 [SMILES: N#Cc1ccc2nccc(NCCc3ccc4cc(C(=O)N5CCN(CCCO)CC5)ccc4c3)c2c1] | C30H31N5O2 | 493.61 | 115 nM | 164 nM | 161 nM | 4.1 nM |

TABLE 5-continued

Comparison of activity

| SCCP ID | Structure | Chemical formula | Mol. wt | IC50 (293-NFKB-Luc) | IC50 (MV4-11-Luc) | IC50 (HL60-Luc) | IC50 (LanthaScreen) |
|---|---|---|---|---|---|---|---|
| 6440 | (structure: quinoline-CN with HN-CH2CH2-naphthalene-C(O)-piperazine-N-Boc) | C32H33N5O3 | 535.65 | 137 nM | 146 nM | 67 nM | 18.9 nM |
| 6283 | (structure: quinoline-CN with HN-CH2CH2-naphthalene-C(O)-piperazine-NH) | C27H25N5O | 435.5 | 334 nM | 219 nM | 756 nM | 5.8 nM |
| 6294 | (structure: quinoline-CN with HN-CH2CH2-naphthalene-C(O)-thiomorpholine) | C27H24N4OS | 452.58 | 107 nM | 92 nM | 73.4 nM | 9.7 nM |

TABLE 5-continued

Comparison of activity

| SCCP ID | Structure | Chemical formula | Mol. wt | IC50 (293-NFKB-Luc) | IC50 (MV4-11-Luc) | IC50 (HL60-Luc) | IC50 (LanthaScreen) |
|---|---|---|---|---|---|---|---|
| 6295 | 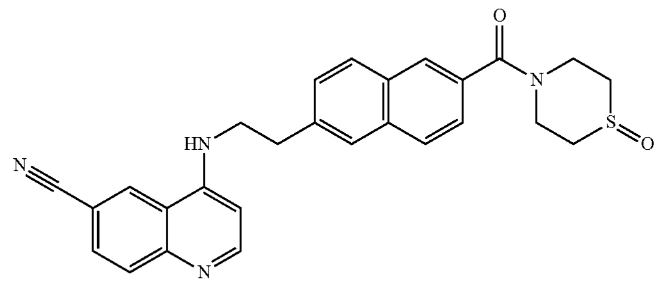 [SMILES: N#Cc1ccc2nccc(NCCc3ccc4cc(C(=O)N5CCS(=O)CC5)ccc4c3)c2c1] | C27H24N4O2S | 468.58 | 160 nM | 218 nM | 163 nM | 5.8 nM |
| 6299 | 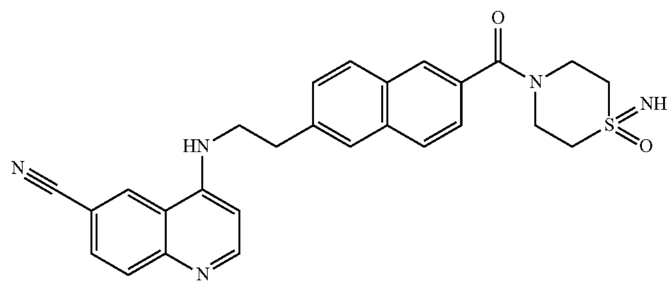 [SMILES: N#Cc1ccc2nccc(NCCc3ccc4cc(C(=O)N5CCS(=N)(=O)CC5)ccc4c3)c2c1] | C27H25N5O2S | 483.59 | 213 nM | 275 nM | 260 nM | 4.6 nM |
| 6326 | 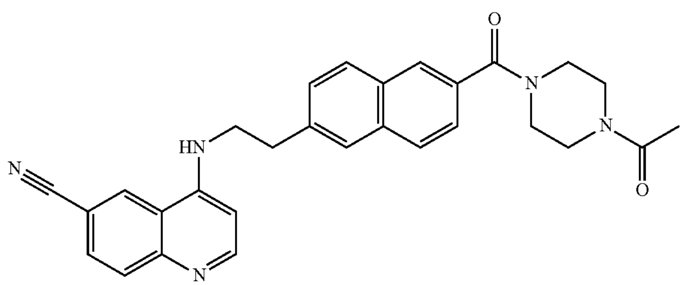 [SMILES: CC(=O)N1CCN(C(=O)c2ccc3cc(CCNc4ccnc5ccc(C#N)cc45)ccc3c2)CC1] | C29H27N5O2 | 477.57 | 178 nM | 295 nM | 162 nM | 11.7 nM |

TABLE 5-continued

Comparison of activity

| SCCP ID | Structure | Chemical formula | Mol. wt | IC50 (293-NFKB-Luc) | IC50 (MV4-11-Luc) | IC50 (HL60-Luc) | IC50 (LanthaScreen) |
|---|---|---|---|---|---|---|---|
| 6336 | 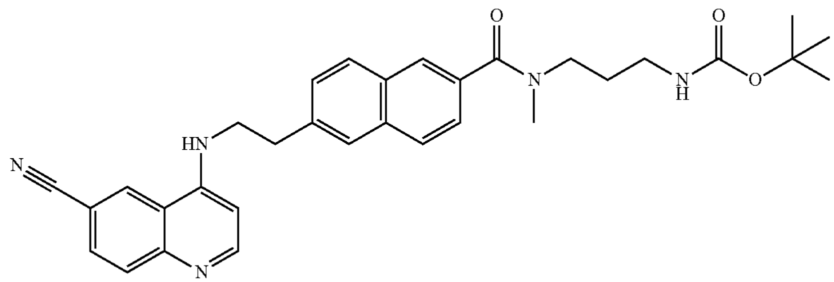 [SMILES: CN(CCCNC(=O)OC(C)(C)C)C(=O)c1ccc2cc(CCNc3ccnc4ccc(C#N)cc34)ccc2c1] | C32H35N5O3 | 537.27 | 208 nM | 181 nM | 154 nM | 9.3 nM |
| 6337 | 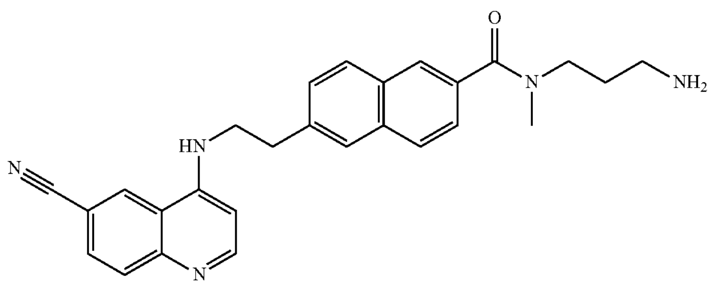 [SMILES: CN(CCCN)C(=O)c1ccc2cc(CCNc3ccnc4ccc(C#N)cc34)ccc2c1] | C27H27N5O | 437.22 | 113 nM | 297 nM | 255 nM | 9.2 nM |
| 6345 | 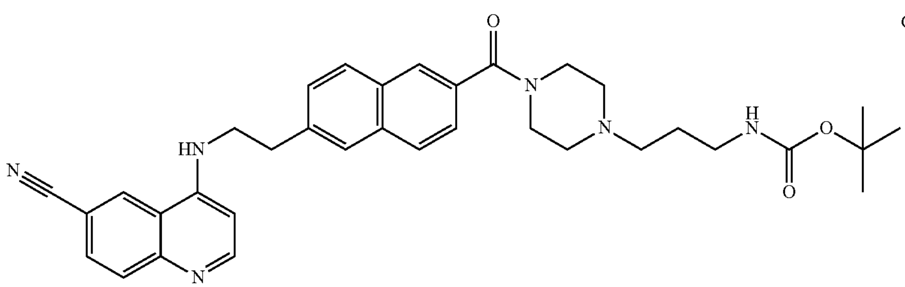 [SMILES: CC(C)(C)OC(=O)NCCCN1CCN(C(=O)c2ccc3cc(CCNc4ccnc5ccc(C#N)cc45)ccc3c2)CC1] | C35H40N6O3 | 592.32 | 85 nM | 122 nM | 61 nM | 8.1 nM |

TABLE 5-continued
Comparison of activity
| SCCP ID | Structure | Chemical formula | Mol. wt | IC50 (293-NFKB-Luc) | IC50 (MV4-11-Luc) | IC50 (HL60-Luc) | IC50 (LanthaScreen) |
|---|---|---|---|---|---|---|---|
| 6346 | 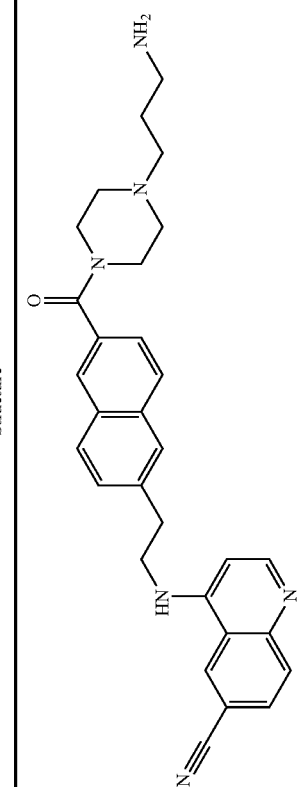 | C30H32N6O | 492.26 | 837 nM | 305 nM | 308 nM | 6.5 nM |

We claim:

1. A compound of Formula 1B (Formula IB)

[structure: quinoline with HN-R³ linker to naphthalene bearing R⁴, and R¹ substituent on quinoline]

wherein R¹ is —CN, NO₂, a halogen, an amino, or a halo-substituted alkyl;

wherein R³ is a substituted or unsubstituted, branched or unbranched C1-C6 alkylene; and wherein R⁴ is —C(O)NR$^A$R$^B$ where—
  R$^A$ and R$^B$ groups on the same nitrogen are taken together with their intervening atoms to form a substituted or unsubstituted 4-7 membered saturated, partially unsaturated, or heteroaryl ring having 0-3 heteroatoms, in addition to the nitrogen, independently selected from nitrogen, oxygen, or sulfur; or
  each R$^A$ and R$^B$ are independently selected from hydrogen, a substituted or unsubstituted alkyl, a substituted or unsubstituted cycloalkyl, a substituted or unsubstituted phenyl, a substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur.

2. The compound of claim 1, wherein R⁴ is

[structure: morpholine-like ring with N-C(=O)- linker and D substituent]

and
wherein—
  D is —N(R$^C$)— and R$^C$ is a substituted, branched or unbranched C1-C6 alkyl or
  D is —S(=O)(=NR$^D$)— and R$^D$ is hydrogen or a substituted or unsubstituted, branched or unbranched C1-C6 alkyl, —S—, or —S(O)—.

3. The compound of claim 2, wherein D is —N(R$^C$)— and R$^C$ is an oxo substituted C1-C6 alkyl.

4. The compound of claim 3, wherein R$^C$ is —C(O)CH₃ or —C(O)OC(CH₃)₃.

5. The compound of claim 2, wherein D is —N(R$^C$)— and R$^C$ is a hydroxyl substituted C1-C6 alkyl.

6. The compound of claim 5, wherein R$^C$ is —(CH₂)₃OH.

7. The compound of claim 2, wherein D is —N(R$^C$)— and R$^C$ is an amino substituted C1-C6 alkyl.

8. The compound of claim 5, wherein R$^C$ is —(CH₂)₃NH₂.

9. The compound of claim 2, wherein D is —S(=O)(=NR$^D$)— and R$^D$ is hydrogen or the substituted or unsubstituted, branched or unbranched C1-C6 alkyl, —S—, or —S(O)—.

10. The compound of claim 9, wherein D is —S(=O)(=NR$^D$)— and R$^D$ is hydrogen.

11. The compound of claim 1, wherein each R$^A$ and R$^B$ are independently selected from hydrogen, the substituted or unsubstituted alkyl, the substituted or unsubstituted cycloalkyl, the substituted or unsubstituted phenyl, the substituted or unsubstituted 4-7 membered saturated or partially unsaturated heterocyclic having 1-2 heteroatoms independently selected from nitrogen, oxygen, or sulfur, or a substituted or unsubstituted 5-6 membered heteroaryl ring having 1-4 heteroatoms independently selected from nitrogen, oxygen, or sulfur.

12. The compound of claim 11, wherein at least one of R$^A$ and R$^B$ is the substituted or unsubstituted alkyl.

13. The compound of claim 11, wherein the at least one substituted or unsubstituted alkyl is —CH₃, an amino substituted C1-C6 alkyl, or a —NHC(O)OC(CH₃)₃ substituted alkyl.

14. The compound of claim 11, wherein at each of R$^A$ and R$^B$ is the substituted or unsubstituted alkyl.

15. The compound of claim 14, wherein one or both of R$^A$ and R$^B$ are independently selected from is —CH₃, an amino substituted C1-C6 alkyl, of a —NHC(O)OC(CH₃)₃ substituted alkyl.

16. A method for the treatment of a subject having a breast cancer or a prostate cancer comprising administering a pharmaceutical composition comprising a therapeutically effective amount of the compound of claim 1.

17. The method of claim 16, wherein R⁴ is

[structure: morpholine-like ring with N-C(=O)- linker and D substituent]

and
wherein—
  D is —N(R$^C$)— and R$^C$ is a substituted, branched or unbranched C1-C6 alkyl or
  D is —S(=O)(=NR$^D$)— and R$^D$ is hydrogen or a substituted or unsubstituted, branched or unbranched C1-C6 alkyl, —S—, or —S(O)—.

18. The method of claim 16, wherein at least one of R$^A$ and R$^B$ is the substituted or unsubstituted alkyl.

19. A method for the inhibition of CDK8 or CDK19, the method comprising contacting CDK8 or CDK19 with an effective amount of the compound of claim 1.

* * * * *